United States Patent
Daon et al.

(10) Patent No.: US 12,070,365 B2
(45) Date of Patent: Aug. 27, 2024

(54) SYSTEM AND METHOD FOR DETERMINING THE THREE-DIMENSIONAL LOCATION AND ORIENTATION OF IDENTIFICATION MARKERS

(71) Applicant: Navigate Surgical Technologies, Inc., Vancouver (CA)

(72) Inventors: Ehud (Udi) Daon, North Vancouver (CA); Martin Gregory Beckett, Bowen Island (CA)

(73) Assignee: Navigate Surgical Technologies, Inc, Vancouver (CA)

( * ) Notice: Subject to any disclaimer, the term of this patent is extended or adjusted under 35 U.S.C. 154(b) by 224 days.

(21) Appl. No.: 17/692,437

(22) Filed: Mar. 11, 2022

(65) Prior Publication Data
US 2022/0265387 A1 Aug. 25, 2022

Related U.S. Application Data

(60) Division of application No. 16/409,835, filed on May 12, 2019, now Pat. No. 11,304,777, which is a
(Continued)

(51) Int. Cl.
*A61B 90/94* (2016.01)
*A61B 90/00* (2016.01)
*A61C 1/08* (2006.01)

(52) U.S. Cl.
CPC .............. *A61B 90/94* (2016.02); *A61B 90/39* (2016.02); *A61C 1/082* (2013.01);
(Continued)

(58) Field of Classification Search
CPC . A61B 10/0233; A61B 17/3211; A61B 19/54; A61B 1/00; A61B 1/24;
(Continued)

(56) References Cited

U.S. PATENT DOCUMENTS

| 5,230,623 A | 7/1993 | Guthrie |
| 5,438,991 A | 8/1995 | Yu et al. |

(Continued)

FOREIGN PATENT DOCUMENTS

| DE | 102004048067 A1 | 4/2006 |
| DE | 102004049258 A1 | 4/2006 |

(Continued)

OTHER PUBLICATIONS

European Patent Office, International Written Opinion, dated Sep. 29, 2014 (PCT/IB2014/060403).
(Continued)

*Primary Examiner* — Mark D Remaly
(74) *Attorney, Agent, or Firm* — Kevin R. Erdman; Brannon Sowers & Cracraft PC

(57) ABSTRACT

The present invention relates to a tool system comprising a handheld implement having a passive vectorized tracking marker permanently integrated with the implement at a predetermined location on the implement in a predetermined orientation with respect to the implement; and a database comprising geometric information describing the at least one of a rotationally asymmetric shape of the tracking marker and a rotationally asymmetric pattern disposed on the tracking marker. The system may further comprise: a tracker configured for obtaining image information about the tracking marker when the tracking marker is in a field of view of the tracker; and a controller having a processor and memory, the controller in communication with the database and the tracker, the processor programmable for receiving and processing image information from the tracker; accessing the database to retrieve the geometric information; and comparing the image information with the geometric information. The handheld implement may be three-dimensionally tracked by the tracker.

22 Claims, 29 Drawing Sheets

Related U.S. Application Data continuation-in-part of application No. 15/050,140, filed on Feb. 22, 2016, now abandoned, which is a continuation-in-part of application No. 14/598,484, filed on Jan. 16, 2015, now Pat. No. 9,566,123, which is a continuation-in-part of application No. 14/226,708, filed on Mar. 26, 2014, now abandoned, and a continuation of application No. 13/822,358, filed as application No. PCT/IL2012/000363 on Oct. 21, 2012, now abandoned, which is a continuation-in-part of application No. 13/571,284, filed on Aug. 9, 2012, now Pat. No. 8,938,282.

(60) Provisional application No. 61/803,040, filed on Mar. 18, 2013, provisional application No. 61/616,673, filed on Mar. 28, 2012.

(52) U.S. Cl.
CPC .............. *A61B 2090/3937* (2016.02); *A61B 2090/3983* (2016.02); *A61C 2204/005* (2013.01)

(58) Field of Classification Search
CPC .. A61B 2017/00477; A61B 2090/3925; A61B 2090/3954; A61B 2090/3966; A61B 2090/3983; A61B 2090/3991; A61B 34/20; A61B 5/055; A61B 5/06; A61B 5/062; A61B 5/064; A61B 5/72; A61B 6/032; A61B 6/12; A61B 6/14; A61B 6/145; A61B 6/52; A61B 8/0841; A61B 90/16; A61B 90/39; A61C 19/04; A61C 1/0007; A61C 1/082; A61C 3/02
See application file for complete search history.

(56) References Cited

U.S. PATENT DOCUMENTS

| | | | |
|---|---|---|---|
| 5,603,318 | A | 2/1997 | Heilbrun et al. |
| 5,828,770 | A | 10/1998 | Leis et al. |
| 5,967,777 | A | 10/1999 | Klein |
| 6,122,541 | A | 9/2000 | Cosman et al. |
| 6,414,746 | B1 | 7/2002 | Stettner |
| 6,468,265 | B1 | 10/2002 | Evans et al. |
| 6,529,765 | B1 | 3/2003 | Franck et al. |
| 7,653,455 | B2 | 1/2010 | Cinador |
| 7,720,521 | B2 | 5/2010 | Chang |
| 7,758,345 | B1 | 7/2010 | Christensen |
| 7,894,878 | B2 | 2/2011 | Noujeim |
| 7,899,512 | B2 | 3/2011 | Labadie |
| 8,014,575 | B2 | 9/2011 | Weiss et al. |
| 8,018,579 | B1 | 9/2011 | Krah |
| 8,172,573 | B2 | 5/2012 | Sonenfeld |
| 8,395,482 | B2 | 3/2013 | Sadr |
| 8,711,221 | B2 | 4/2014 | Eggert |
| 2004/0002642 | A1 | 1/2004 | Dekel et al. |
| 2004/0097952 | A1 | 5/2004 | Sarin et al. |
| 2004/0138556 | A1 | 7/2004 | Cowman |
| 2004/0152970 | A1 | 8/2004 | Hunter |
| 2005/0085719 | A1 | 4/2005 | Franklin et al. |
| 2005/0163342 | A1 | 7/2005 | Persky |
| 2005/0182318 | A1 | 8/2005 | Kaji et al. |
| 2005/0182320 | A1 | 8/2005 | Stifter |
| 2005/0281465 | A1 | 12/2005 | Marquart |
| 2006/0025677 | A1 | 2/2006 | Verard |
| 2006/0058616 | A1 | 3/2006 | Marquart et al. |
| 2006/0084867 | A1 | 4/2006 | Tremblay |
| 2006/0142657 | A1 | 6/2006 | Quaid et al. |
| 2006/0165310 | A1 | 7/2006 | Mack |
| 2006/0190011 | A1 | 8/2006 | Riles |
| 2006/0200025 | A1 | 9/2006 | Elliott |
| 2006/0212044 | A1 | 9/2006 | Bova et al. |
| 2006/0247517 | A1 | 11/2006 | Labadie et al. |
| 2006/0281991 | A1 | 12/2006 | Fitzpatrick |
| 2007/0208252 | A1 | 9/2007 | Makower |
| 2007/0223910 | A1 | 9/2007 | Aoki |
| 2007/0253541 | A1 | 11/2007 | Sukovic et al. |
| 2008/0026338 | A1 | 1/2008 | Cinader |
| 2008/0068197 | A1 | 3/2008 | Neubauer et al. |
| 2008/0135733 | A1 | 6/2008 | Feilkas |
| 2008/0161682 | A1 | 7/2008 | Kendrick et al. |
| 2008/0171305 | A1 | 7/2008 | Sonenfeld et al. |
| 2008/0183071 | A1 | 7/2008 | Strommer |
| 2008/0193896 | A1 | 8/2008 | Yang |
| 2008/0200927 | A1 | 8/2008 | Hartmann et al. |
| 2008/0262345 | A1 | 10/2008 | Fichtinger |
| 2008/0319491 | A1 | 12/2008 | Schoenefeld |
| 2009/0012509 | A1 | 1/2009 | Csavoy |
| 2009/0171196 | A1 | 7/2009 | Olson et al. |
| 2009/0253095 | A1 | 10/2009 | Salcedo |
| 2010/0039506 | A1 | 2/2010 | Sarvestani et al. |
| 2010/0049195 | A1 | 2/2010 | Park et al. |
| 2010/0168562 | A1 | 7/2010 | Zhao et al. |
| 2010/0168763 | A1 | 7/2010 | Zhao et al. |
| 2010/0210939 | A1 | 8/2010 | Hartmann et al. |
| 2010/0217139 | A1 | 8/2010 | Pinter et al. |
| 2010/0298712 | A1 | 11/2010 | Pelissier et al. |
| 2011/0008751 | A1 | 1/2011 | Patterssen |
| 2011/0029913 | A1 | 2/2011 | Boillot et al. |
| 2011/0087332 | A1 | 4/2011 | Bojarski et al. |
| 2011/0217667 | A1 | 9/2011 | Groscruth |
| 2011/0257653 | A1 | 10/2011 | Hughes |
| 2012/0065496 | A1 | 3/2012 | Stratton |
| 2012/0115107 | A1 | 5/2012 | Adams |
| 2012/0229383 | A1 | 9/2012 | Hamilton et al. |
| 2012/0253186 | A1 | 10/2012 | Simpson et al. |
| 2012/0259204 | A1 | 10/2012 | Carrat et al. |
| 2012/0265051 | A1 | 10/2012 | Fischer et al. |
| 2012/0283637 | A1 | 11/2012 | Cohen |
| 2012/0323364 | A1 | 12/2012 | Birkenback et al. |
| 2013/0063558 | A1 | 3/2013 | Phipps |
| 2013/0122463 | A1 | 5/2013 | Csillag |
| 2013/0332271 | A1 | 5/2013 | Doron et al. |
| 2013/0218024 | A1 | 8/2013 | Boctor |
| 2013/0258353 | A1 | 10/2013 | Kosmecki et al. |
| 2014/0030669 | A1 | 1/2014 | Tey et al. |
| 2014/0049629 | A1 | 2/2014 | Siewerdsen et al. |
| 2014/0199650 | A1 | 7/2014 | Moffson |
| 2015/0150641 | A1 | 6/2015 | Daon et al. |
| 2015/0178992 | A1 | 6/2015 | Bhuruth |
| 2016/0038253 | A1 | 2/2016 | Piron et al. |

FOREIGN PATENT DOCUMENTS

| | | |
|---|---|---|
| DE | 10 2005 026654 | 12/2006 |
| DE | 102009009158 | 9/2010 |
| DE | 2010042540 | 4/2012 |
| EP | 1442715 | 8/2004 |
| EP | 1527417 | 9/2011 |
| FR | 2929794 | 8/2008 |
| FR | 2929794 | 10/2009 |
| GB | 2416949 | 8/2006 |
| JP | 2000046546 | 2/2000 |
| JP | 2007253748 | 10/2007 |
| JP | 2009172411 | 5/2009 |
| WO | 1999/27839 | 6/1999 |
| WO | 2002/076302 | 10/2002 |
| WO | 03096920 | 11/2003 |
| WO | 2004070577 A2 | 8/2004 |
| WO | 2005001679 A1 | 1/2005 |
| WO | 2008/009136 | 1/2008 |
| WO | 2010/086374 | 5/2010 |
| WO | 2010078016 A1 | 7/2010 |
| WO | 2011012460 | 2/2011 |
| WO | 2011012460 A2 | 2/2011 |
| WO | 2011085813 A1 | 7/2011 |
| WO | 2011085815 A1 | 7/2011 |
| WO | 2011/109041 | 9/2011 |
| WO | 2011113441 | 9/2011 |
| WO | 2012/068679 | 5/2012 |
| WO | 2012068679 | 5/2012 |
| WO | 2012095642 | 7/2012 |

(56) References Cited

FOREIGN PATENT DOCUMENTS

| WO | 2012149548 | 11/2012 |
| WO | 20120149548 | 11/2012 |
| WO | 2013010138 | 1/2013 |
| WO | 2013055707 | 4/2013 |
| WO | 2013096766 | 6/2013 |
| WO | 2011/109041 | 10/2013 |
| WO | 2013/144939 | 10/2013 |
| WO | 2013144208 | 10/2013 |
| WO | 2013144939 | 10/2013 |
| WO | 2014138916 A1 | 9/2014 |
| WO | 2014147601 | 9/2014 |
| WO | 2014201968 | 12/2014 |

OTHER PUBLICATIONS

European Patent Office, International Written Opinion, dated Oct. 17, 2014 (PCT/EP2014/067280).
European Patent Office, Written Opinion of the International Searching Authority, International Application No. PCT/EP2014/067280, dated Oct. 27, 2014.
United States Patent and Trademark Office, Prosecution of U.S. Appl. No. 13/713,165, First Office Action of Aug. 13, 2014 and Amendment of Aug. 14, 2014.
European Patent Office, International Written Opinion, dated Jul. 30, 2014 (PCT/EP2014/057656).
European Patent Office, International Written Opinion, dated Jul. 30, 2014 (PCT/EP2014/060018).
United States Patent and Trademark Office, Non-Final Office Action for U.S. Appl. No. 13/571,284, dated Aug. 15, 2013.
European Patent Office, International Search Report, dated Sep. 3, 2013 (PCT/IL2013/000032).
United States Patent and Trademark Office, Office Action, dated Sep. 30, 2015, U.S. Appl. No. 13/744,967.
United States Patent and Trademark Office, Non Final Office Action dated Jun. 23, 2016, U.S. Appl. No. 13/745,249.
European Patent Office, International Search Report, dated Sep. 16, 2013 (PCT/EP2013/056525).
United States Patent and Trademark Office, Office Action, Jul. 8, 2015, U.S. Appl. No. 13/745,763.
European Patent Office, International Search Report, mailed Sep. 17, 2013 (PCT/IL2013/000031).
Prosecution of U.S. Appl. No. 13/571,284, from First Office Action of Aug. 15, 2013 to Amendment with Request for Continued Examination of Feb. 26, 2014.
United States Patent and Trademark Office Office Action, Feb. 13, 2015, U.S. Appl. No. 13/822,358.
European Patent Office, International Search Written Opinion, mailed Mar. 4, 2013 (PCT/IL2012/000363).
European Patent Office, International Search Report and Written Opinion, dated Feb. 18, 2014 (PCT/EP2013/073416).
Arizona Center for Laser Dentistry, Root Canal Therapy, Dec. 19, 2010.

European Patent Office, International Written Opinion, dated Nov. 5, 2015 (PCT/EP2014/058406).
European Patent Office, Written Opinion of the International Searching Authority, International Application No. PCT/EP2013/073401, dated Mar. 19, 2014.
European Patent Office, International Search Report, International Application No. PCT/EP2014/057656, dated Aug. 11, 2014.
European Patent Office, Written Opinion of the International Searching Authority, International Application No. PCT/EP2014/051656, dated Aug. 11, 2014.
European Patent Office, Written Opinion of the International Searching Authority, International Application No. PCT/EP2014/060018, dated Aug. 11, 2014.
European Patent Office, Written Opinion of the International Searching Authority, International Application No. PCT/EP2014/067279, dated Nov. 7, 2014.
Japanese Patent Office (JPO) Notice of Preliminary Rejection, Japan Patent Application No. 2014-537811, Based upon PCT/IL2012/000363, Jan. 25, 2016, which claims priority to U.S. Appl. No. 13/571,284, now U.S. Pat. No. 8,938,282.
Japanese Patent Office (JPO) Notice of Preliminary Rejection, Japanese Patent Application No. 2015-541159, Based upon PCT/EP2013/0073401, Mar. 1, 2016, which claims priority to U.S. Appl. No. 14/562,691, now U.S. Pat. No. 8,908,918.
European Patent Office, International Search Report for PCT/EP2016/067258, Dec. 14, 2016.
European Patent Office, International Search Report for PCT/EP2016/054110, Dec. 5, 2016.
European Patent Office, International Search Report for PCT/EP2016/069185, Jan. 18, 2017.
European Patent Office, Written Opinion of the International Searching Authority, International Application No. PCT/IL2015/050400, Navigate Surgical Technologies, Inc., Jul. 16, 2015.
European Patent Office, International Search Report, International Application No. PCT/IL2015/050400, Navigate Surgical Technologies, Inc., Jul. 16, 2015.
United States Patent and Trademark Office, Non-Final Office Action for U.S. Appl. No. 13/744,967, dated Jun. 30, 2015.
United States Patent and Trademark Office, Response to Non-Final Office Action for U.S. Appl. No. 13/745,763, dated Mar. 25, 2015.
European Patent Office, International Search Report, dated Jul. 17, 2014 (PCT/EP2014/058406).
European Patent Office, International Written Opinion, dated Aug. 18, 2014 (PCT/EP2014/058406).
United States Patent and Trademark Office, Office Action in related U.S. Appl. No. 13/735,487 dated Nov. 14, 2014.
United States Patent and Trademark Office, Office Action in related U.S. Appl. No. 13/745,763 dated Dec. 29, 2014.
European Patent Office, International Search Report for PCT/EP2016/054110, Jun. 10, 2016.
European Patent Office, International Search Report for PCT/EP2016/072301, Dec. 5, 2016.
United States Patent and Trademark Office, Non Final Office Action in related U.S. Appl. No. 16/409,835 dated Aug. 19, 2021.

SYSTEM AND METHOD FOR DETERMINING THE THREE-DIMENSIONAL LOCATION AND ORIENTATION OF IDENTIFICATION MARKERS

CROSS-REFERENCE TO RELATED APPLICATIONS

The present application is a Divisional of U.S. patent application Ser. No. 16/409,835, filed May 12, 2019, which is a continuation-in-part of U.S. patent application Ser. No. 15/050,140, filed Feb. 22, 2016; which is a continuation-in-part of U.S. patent application Ser. No. 14/598,484, filed Jan. 16, 2015, now U.S. Pat. No. 9,566,123; which is a continuation-in-part of U.S. patent application Ser. No. 14/226,708, filed Mar. 26, 2014, which claims priority under 35 U.S.C. § 119(e) of U.S. Patent Provisional Application Ser. No. 61/803,040, filed Mar. 18, 2013. In addition, the present application is a continuation-in-part of U.S. patent application Ser. No. 13/822,358, filed Mar. 12, 2013, which is a national stage entry of PCT International Application Serial Number PCT/IL2012/000363, filed Oct. 21, 2012; and is a continuation-in-part of U.S. patent application Ser. No. 13/571,284, filed Aug. 9, 2012, now U.S. Pat. No. 8,938,282; both of which claim priority under 35 U.S.C. § 119(e) of U.S. Patent Provisional Application Ser. No. 61/616,673, filed on Mar. 28, 2012; the disclosures of all of which are incorporated by reference herein.

BACKGROUND OF THE INVENTION

Field of the Invention

The invention relates to location monitoring hardware and software systems. More specifically, the field of the invention is that of surgical equipment and software for monitoring surgical conditions.

Description of the Related Art

Visual and other sensory systems are known, with such systems being capable of both observing and monitoring surgical procedures. With such observation and monitoring systems, computer aided surgeries are now possible, and in fact are being routinely performed. In such procedures, the computer software interacts with both clinical images of the patient and observed surgical images from the current surgical procedure to provide guidance to the physician in conducting the surgery. For example, in one known system a carrier assembly bears at least one fiducial marker onto an attachment element in a precisely repeatable position with respect to a patient's jaw bone, employing the carrier assembly for providing registration between the fiducial marker and the patient's jaw bone and implanting the tooth implant by employing a tracking system which uses the registration to guide a drilling assembly. With this relatively new computer implemented technology, further improvements may further advance the effectiveness of surgical procedures.

SUMMARY OF THE INVENTION

The present invention, in an embodiment, involves an implement having a plurality of interchangeable portions each having a working tip; and an invariant portion bearing the tracking marker. The invariant portion of the implement may be a rigid positioning and orienting portion of the implement. The implement may further comprise: a contactlessly interrogatable microchip disposed on the invariant portion of the implement, the microchip comprising a memory; a database of geometric information stored in the memory of the microchip, the geometric information describing: the at least one of a rotationally asymmetric shape and a rotationally asymmetric pattern; and spatial relationships between the at least one of a rotationally asymmetric shape and a rotationally asymmetric pattern and the working tip of each of the plurality of interchangeable portions. The implement may be a drill; the rigid positioning and orienting portion comprising a handle and the interchangeable portion comprising a drill bit.

The contrasting pattern elements may have perimeters comprising mathematically describable curved sections. The mathematically describable curved sections may be conic sections. The contrasting pattern elements may include round dots. The rotationally asymmetric pattern is scribed, engraved, stamped, or embossed on the tracking marker.

The implement may further comprise: a contactlessly interrogatable microchip disposed on the handheld implement, the microchip comprising a memory; and a database of geometric information stored in the memory of the microchip, the geometric information describing the at least one of a rotationally asymmetric shape and a rotationally asymmetric pattern. The implement may have a working tip and the geometric information further may describe the spatial relationship between the working tip and the at least one of a rotationally asymmetric shape and a rotationally asymmetric pattern.

The rotationally asymmetric pattern may comprise contrasting pattern elements, the contrasting pattern elements having colors contrasting with a color of a background of the passive vectorized tracking marker and disposed at occupiable locations within a unit cell of the pattern, the occupiable locations within the pattern being previously stored in the database. The rotationally asymmetric pattern may comprise at least a first and a second rotationally asymmetric pattern. The second pattern may be displaced on the passive vectorized tracking marker from the first pattern by a distance different from a shortest distance between occupiable locations within the first pattern and different from a multiple of the shortest distance between occupiable locations within the first pattern.

In another aspect, a trackable tool system is provided comprising: a handheld implement having a three-dimensionally trackable location and three-dimensionally trackable orientation, the implement comprising a passive vectorized tracking marker permanently integrated with the implement at a predetermined location on the implement in a predetermined orientation with respect to the implement, the tracking marker having at least one of a rotationally asymmetric shape and a rotationally asymmetric pattern of contrasting elements disposed on the tracking marker; and a database comprising geometric information describing the at least one of a rotationally asymmetric shape and a rotationally asymmetric pattern disposed on the tracking marker. The system may further comprise: a tracker configured for obtaining image information about the tracking marker and having a field of view, the tracker disposable to have the tracking marker in the field of view of the tracker; and a controller having a processor and memory, the controller in communication with the database and the tracker, the processor having a plurality of instructions stored in the memory that when executed by the processor perform the actions of: receiving and processing the image information from the tracker; accessing the database to retrieve the geometric information; and comparing the image information with the geometric information. The tracker may be a non-stereo tracker. The tracking marker may be monolithically integrated with the implement or may be permanently attached to the implement and structurally distinct from the implement. The system may further comprise a contactlessly interrogatable microchip affixed to the handheld implement and wherein the database of geometric information is permanently stored in the microchip.

In a further aspect, a method is provided for tracking a handheld implement bearing a passive vectorized tracking marker permanently integrated with the implement, the marker having an identifiably unique rotationally asymmetric pattern of contrasting elements disposed on the marker, the method comprising: providing the handheld implement bearing a passive vectorized tracking marker permanently integrated with the implement; obtaining image information about the implement from a non-stereo optical tracker; obtaining from a database geometric information about the tracking marker; identifying the passive vectorized tracking marker on the basis of the unique pattern; determining within the image information the location of at least one pattern reference point of the passive vectorized tracking marker based on the geometric information, and determining within the image information the rotational orientation of the passive vectorized tracking marker based on the geometric information.

In this method, obtaining from a database geometric information may comprise obtaining information about the locations of contrasting pattern elements within the at least one pattern. The providing the handheld implement may comprise providing a handheld implement bearing a passive vectorized tracking marker monolithically integrated with the implement. The determining the location of the at least one pattern reference point of the passive vectorized tracking marker may comprise differentiating between different unit cells of rotationally asymmetric patterns in the image information and confirming one of the absence and the presence of contrasting pattern elements at occupiable locations within the unit cells. The confirming may comprise detecting a color contrast between the pattern elements and the at least one passive vectorized tracking marker on which they are disposed. The confirming may comprise calculating the occupiable locations on the passive vectorized tracking marker based on the geometric information from the database. The differentiating may be based on a center-to-center distance between two closest neighbor pattern elements within the at least one rotationally asymmetric pattern. The differentiating between different unit cells of rotationally asymmetric patterns may comprise differentiating between different unit cells of rotationally asymmetric patterns. The determining the location of the at least one pattern reference point may further comprise fitting a mathematical curve to a perimeter of at least one of the contrasting pattern elements.

In a further aspect, a method is provided for monitoring changes in a handheld surgical implement in three dimensions relative to a surgical site, the method comprising: attaching a single passive vectorized scan-visible fiducial reference at a fiducial location proximate the surgical site; obtaining scan data by performing a scan of the surgical site and the fiducial location with the fiducial reference attached; obtaining from the scan data a three-dimensional spatial relationship between the fiducial reference and the surgical site; disposing in a field of view of a tracker a first passive vectorized tracking marker in fixed spatial relation with the fiducial reference; disposing in the field of view of the tracker the surgical implement comprising an interchangeable portion and an invariant portion, the invariant portion bearing a second passive vectorized marker permanently integrated with the invariant portion; obtaining image information of the field of view from the tracker; determining from the image information a three-dimensional location and orientation of the first tracking marker relative to the surgical site; identifying the interchangeable portion of the surgical implement in the image information; and determining from the image information and from the three-dimensional location and orientation of the first tracking marker relative to the surgical site the three-dimensional location and orientation of a working tip of the interchangeable portion of the surgical implement relative to the surgical site.

In this method, the disposing in the field of view of the tracker the surgical implement may comprise disposing in the field of view of the tracker a surgical implement comprising an invariant portion bearing a second passive vectorized marker monolithically integrated with the invariant portion. The determining of the location and orientation of a working tip of the interchangeable portion relative to the surgical site may comprise determining from the image information the three-dimensional location and orientation of the second tracking marker attached to the invariant portion. Identifying the interchangeable portion of the surgical implement in the image information may be based on pre-surgical information in a database.

The identifying the interchangeable portion of the surgical implement in the image information may comprise determining the three dimensional location of the working tip of the interchangeable portion and determining the length of the interchangeable portion from the three-dimensional location of the working tip and the three-dimensional location and orientation of the second tracking marker. The determining the three dimensional location of a working tip of the interchangeable portion may comprise triangulating the three dimensional location of the working tip based on two separate perspectives of the interchangeable portion in the field of view of the tracker.

In a further aspect, a method is provided for making a three-dimensionally trackable apparatus having a working tip, the method comprising: permanently integrating a three-dimensional passive tracking marker with a rigid positioning and orienting portion of the apparatus, the rigid positioning and orienting portion having a predetermined spatial relationship with respect to the working tip; obtaining a first machine-vision image of the mutually integral tracking marker and at least one portion; vectorizing the tracking marker by establishing based on the first machine-vision image and the predetermined spatial relationship a rotationally asymmetric pattern on the tracking marker. The establishing a rotationally asymmetric pattern may comprise establishing a plurality of contrasting portions. The establishing a plurality of contrasting portions may comprise establishing at least one contrasting portion having a mathematically describable perimeter. The establishing a rotationally asymmetric pattern may comprise one of scribing, engraving, stamping, and embossing the contrasting portions. In this method, the permanently integrating may comprise monolithically forming a three-dimensional passive tracking marker integral with the rigid positioning and orienting portion of the apparatus.

The method may further comprise: associating a unique serial number with the rigid positioning and orienting portion; obtaining after the establishing a pattern a second machine vision image of the rigid positioning and orienting portion and the tracking marker comprising the rotationally asymmetric pattern; determining from the second machine-vision image an actual spatial relationship between the rotationally asymmetric pattern and the working tip; and recording the actual spatial relationship in association with the unique serial number. The recording may comprise: affixing a contactlessly interrogatable microchip to the rigid positioning and orienting portion; and programming the actual spatial relationship into the microchip.

BRIEF DESCRIPTION OF THE DRAWINGS

The above-mentioned and other features and objects of this invention, and the manner of attaining them, will become more apparent and the invention itself will be better understood by reference to the following description of embodiments of the invention taken in conjunction with the accompanying drawings, wherein.

Figure 1:
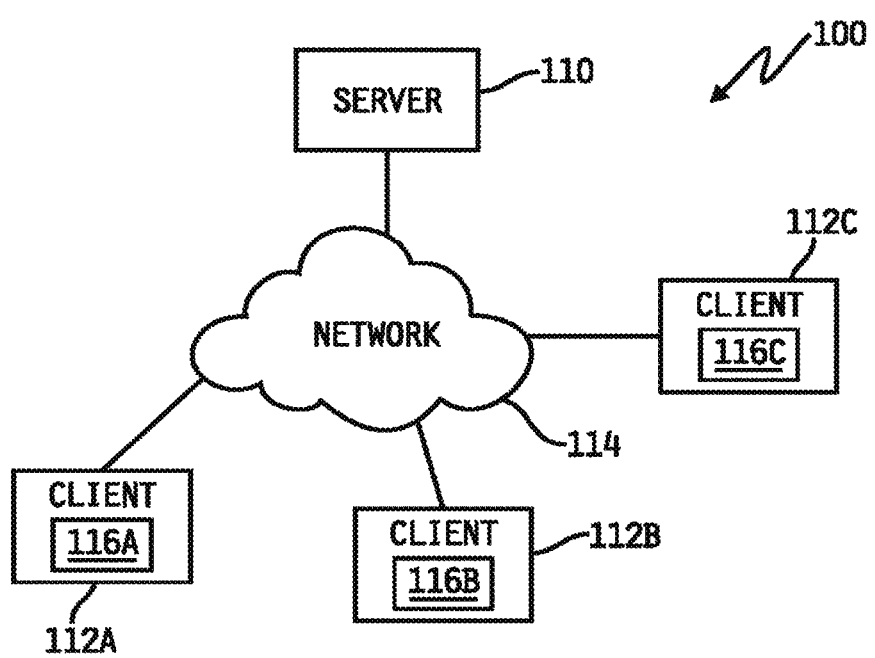
FIG. 1 is a schematic diagrammatic view of a network system in which embodiments of the present invention may be utilized.

Corresponding reference characters indicate corresponding parts throughout the several views. Although the drawings represent embodiments of the present invention, the drawings are not necessarily to scale and certain features may be exaggerated in order to better illustrate and explain the present invention. The flow charts and screen shots are also representative in nature, and actual embodiments of the invention may include further features or steps not shown in the drawings. The exemplification set out herein illustrates an embodiment of the invention, in one form, and such exemplifications are not to be construed as limiting the scope of the invention in any manner.

DESCRIPTION OF EMBODIMENTS OF THE PRESENT INVENTION

The embodiments disclosed below are not intended to be exhaustive or limit the invention to the precise form disclosed in the following detailed description. Rather, the embodiments are chosen and described so that others skilled in the art may utilize their teachings.

The detailed descriptions that follow are presented in part in terms of algorithms and symbolic representations of operations on data bits within a computer memory representing alphanumeric characters or other information. The hardware components are shown with particular shapes and relative orientations and sizes using particular scanning techniques, although in the general case one of ordinary skill recognizes that a variety of particular shapes and orientations and scanning methodologies may be used within the teaching of the present invention. A computer generally includes a processor for executing instructions and memory for storing instructions and data, including interfaces to obtain and process imaging data. When a general-purpose computer has a series of machine encoded instructions stored in its memory, the computer operating on such encoded instructions may become a specific type of machine, namely a computer particularly configured to perform the operations embodied by the series of instructions. Some of the instructions may be adapted to produce signals that control operation of other machines and thus may operate through those control signals to transform materials far removed from the computer itself. These descriptions and representations are the means used by those skilled in the art of data processing arts to most effectively convey the substance of their work to others skilled in the art.

An algorithm is here, and generally, conceived to be a self-consistent sequence of steps leading to a desired result. These steps are those requiring physical manipulations of physical quantities, observing and measuring scanned data representative of matter around the surgical site. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as bits, values, symbols, characters, display data, terms, numbers, or the like as a reference to the physical items or manifestations in which such signals are embodied or expressed to capture the underlying data of an image. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory, rather they represent specific electronic structural elements that impart or manifest a physical organization on the information stored in memory. More than mere abstraction, the data structures are specific electrical or magnetic structural elements in memory, which simultaneously represent complex data accurately, often data modeling physical characteristics of related items, and provide increased efficiency in computer operation.

Further, the manipulations performed are often referred to in terms, such as comparing or adding, commonly associated with mental operations performed by a human operator. No such capability of a human operator is necessary, or desirable in most cases, in any of the operations described herein that form part of the present invention; the operations are machine operations. Useful machines for performing the operations of the present invention include general-purpose digital computers or other similar devices. In all cases the distinction between the method operations in operating a computer and the method of computation itself should be recognized. The present invention relates to a method and apparatus for operating a computer in processing electrical or other (e.g., mechanical, chemical) physical signals to generate other desired physical manifestations or signals. The computer operates on software modules, which are collections of signals stored on a media that represents a series of machine instructions that enable the computer processor to perform the machine instructions that implement the algorithmic steps. Such machine instructions may be the actual computer code the processor interprets to implement the instructions, or alternatively may be a higher level coding of the instructions that is interpreted to obtain the actual computer code. The software module may also include a hardware component, wherein some aspects of the algorithm are performed by the circuitry itself rather as a result of an instruction.

The present invention also relates to an apparatus for performing these operations. This apparatus may be specifically constructed for the required purposes or it may comprise a general-purpose computer as selectively activated or reconfigured by a computer program stored in the computer. The algorithms presented herein are not inherently related to any particular computer or other apparatus unless explicitly indicated as requiring particular hardware. In some cases, the computer programs may communicate or relate to other programs or equipments through signals configured to particular protocols, which may or may not require specific hardware or programming to interact. In particular, various general-purpose machines may be used with programs written in accordance with the teachings herein, or it may prove more convenient to construct more specialized apparatus to perform the required method steps. The required structure for a variety of these machines will appear from the description below.

The present invention may deal with "object-oriented" software, and particularly with an "object-oriented" operating system. The "object-oriented" software is organized into "objects", each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects. Often, but not necessarily, a physical object has a corresponding software object that may collect and transmit observed data from the physical device to the software system. Such observed data may be accessed from the physical object and/or the software object merely as an item of convenience; therefore where "actual data" is used in the following description, such "actual data" may be from the instrument itself or from the corresponding software object or module.

Messages are sent and received between objects having certain functions and knowledge to carry out processes. Messages are generated in response to user instructions, for example, by a user activating an icon with a "mouse" pointer generating an event. Also, messages may be generated by an object in response to the receipt of a message. When one of the objects receives a message, the object carries out an operation (a message procedure) corresponding to the message and, if necessary, returns a result of the operation. Each object has a region where internal states (instance variables) of the object itself are stored and here the other objects are not allowed to access. One feature of the object-oriented system is inheritance. For example, an object for drawing a "circle" on a display may inherit functions and knowledge from another object for drawing a "shape" on a display.

A programmer "programs" in an object-oriented programming language by writing individual blocks of code each of which creates an object by defining its methods. A collection of such objects adapted to communicate with one another by means of messages comprises an object-oriented program. Object-oriented computer programming facilitates the modeling of interactive systems in that each component of the system may be modeled with an object, the behavior of each component being simulated by the methods of its corresponding object, and the interactions between components being simulated by messages transmitted between objects.

An operator may stimulate a collection of interrelated objects comprising an object-oriented program by sending a message to one of the objects. The receipt of the message may cause the object to respond by carrying out predetermined functions, which may include sending additional messages to one or more other objects. The other objects may in turn carry out additional functions in response to the messages they receive. Including sending still more messages. In this manner, sequences of message and response may continue indefinitely or may come to an end when all messages have been responded to and no new messages are being sent. When modeling systems utilizing an object-oriented language, a programmer need only think in terms of how each component of a modeled system responds to a stimulus and not in terms of the sequence of operations to be performed in response to some stimulus. Such sequence of operations naturally flows out of the interactions between the objects in response to the stimulus and need not be preordained by the programmer.

Although object-oriented programming makes simulation of systems of interrelated components more intuitive, the operation of an object-oriented program is often difficult to understand because the sequence of operations carried out by an object-oriented program is usually not immediately apparent from a software listing as in the case for sequentially organized programs. Nor is it easy to determine how an object-oriented program works through observation of the readily apparent manifestations of its operation. Most of the operations carried out by a computer in response to a program are "invisible" to an observer since only a relatively few steps in a program typically produce an observable computer output.

In the following description, several terms that are used frequently have specialized meanings in the present context. The term "object" relates to a set of computer instructions and associated data, which may be activated directly or indirectly by the user. The terms "windowing environment", "running in windows", and "object oriented operating system" are used to denote a computer user interface in which information is manipulated and displayed on a video display such as within bounded regions on a raster scanned video display. The terms "network", "local area network", "LAN", "wide area network", or "WAN" mean two or more computers that are connected in such a manner that messages may be transmitted between the computers. In such computer networks, typically one or more computers operate as a "server", a computer with large storage devices such as hard disk drives and communication hardware to operate peripheral devices such as printers or modems. Other computers, termed "workstations", provide a user interface so that users of computer networks may access the network resources, such as shared data files, common peripheral devices, and inter-workstation communication. Users activate computer programs or network resources to create "processes" which include both the general operation of the computer program along with specific operating characteristics determined by input variables and its environment. Similar to a process is an agent (sometimes called an intelligent agent), which is a process that gathers information or performs some other service without user intervention and on some regular schedule. Typically, an agent, using parameters typically provided by the user, searches locations either on the host machine or at some other point on a network, gathers the information relevant to the purpose of the agent, and presents it to the user on a periodic basis.

The term "desktop" means a specific user interface which presents a menu or display of objects with associated settings for the user associated with the desktop. When the desktop accesses a network resource, which typically requires an application program to execute on the remote server, the desktop calls an Application Program Interface, or "API", to allow the user to provide commands to the network resource and observe any output. The term "Browser" refers to a program which is not necessarily apparent to the user, but which is responsible for transmitting messages between the desktop and the network server and for displaying and interacting with the network user. Browsers are designed to utilize a communications protocol for transmission of text and graphic information over a worldwide network of computers, namely the "World Wide Web" or simply the "Web". Examples of Browsers compatible with the present invention include the Internet Explorer program sold by Microsoft Corporation (Internet Explorer is a trademark of Microsoft Corporation), the Opera Browser program created by Opera Software ASA, or the Firefox browser program distributed by the Mozilla Foundation (Firefox is a registered trademark of the Mozilla Foundation). Although the following description details such operations in terms of a graphic user interface of a Browser, the present invention may be practiced with text based interfaces, or even with voice or visually activated interfaces, that have many of the functions of a graphic based Browser.

Browsers display information, which is formatted in a Standard Generalized Markup Language ("SGML") or a HyperText Markup Language ("HTML"), both being scripting languages, which embed non-visual codes in a text document through the use of special ASCII text codes. Files in these formats may be easily transmitted across computer networks, including global information networks like the Internet, and allow the Browsers to display text, images, and play audio and video recordings. The Web utilizes these data file formats to conjunction with its communication protocol to transmit such information between servers and workstations. Browsers may also be programmed to display information provided in an eXtensible Markup Language ("XML") file, with XML files being capable of use with several Document Type Definitions ("DTD") and thus more general in nature than SGML or HTML. The XML file may be analogized to an object, as the data and the stylesheet formatting are separately contained (formatting may be thought of as methods of displaying information, thus an XML file has data and an associated method).

The terms "personal digital assistant" or "PDA", as defined above, means any handheld, mobile device that combines computing, telephone, fax, e-mail and networking features. The terms "wireless wide area network" or "WWAN" mean a wireless network that serves as the medium for the transmission of data between a handheld device and a computer. The term "synchronization" means the exchanging of information between a first device, e.g. a handheld device, and a second device, e.g. a desktop computer, either via wires or wirelessly. Synchronization ensures that the data on both devices are identical (at least at the time of synchronization).

In wireless wide area networks, communication primarily occurs through the transmission of radio signals over analog, digital cellular, or personal communications service ("PCS") networks. Signals may also be transmitted through microwaves and other electromagnetic waves. At the present time, most wireless data communication takes place across cellular systems using second generation technology such as code-division multiple access ("CDMA"), time division multiple access ("TDMA"), the Global System for Mobile Communications ("GSM"), Third Generation (wideband or "3G"), Fourth Generation (broadband or "4G"), personal digital cellular ("PDC"), or through packet-data technology over analog systems such as cellular digital packet data ("CDPD") used on the Advance Mobile Phone Service ("AMPS").

The terms "wireless application protocol" or "WAP" mean a universal specification to facilitate the delivery and presentation of web-based data on handheld and mobile devices with small user interfaces. "Mobile Software" refers to the software operating system, which allows for application programs to be implemented on a mobile device such as a mobile telephone or PDA. Examples of Mobile Software are Java and Java ME (Java and JavaME are trademarks of Sun Microsystems, Inc. of Santa Clara, California), BREW (BREW is a registered trademark of Qualcomm Incorporated of San Diego, California), Windows Mobile (Windows is a registered trademark of Microsoft Corporation of Redmond, Washington), Palm OS (Palm is a registered trademark of Palm, Inc. of Sunnyvale, California), Symbian OS (Symbian is a registered trademark of Symbian Software Limited Corporation of London, United Kingdom), ANDROID OS (ANDROID is a registered trademark of Google, Inc. of Mountain View, California), and iPhone OS (iPhone is a registered trademark of Apple, Inc. of Cupertino, California), and Windows Phone 7. "Mobile Apps" refers to software programs written for execution with Mobile Software.

The terms "scan, fiducial reference", "fiducial location", "marker," "tracker" and "image information" have particular meanings in the present disclosure. For purposes of the present disclosure, "scan" or derivatives thereof refer to x-ray, magnetic resonance imaging (MRI), computerized tomography (CT), sonography, cone beam computerized tomography (CBCT), or any system that produces a quantitative spatial representation of a patient and a "scanner" is the means by which such scans are obtained. The term "fiducial reference" or simply "fiducial" refers to an object or reference on the image of a scan that is uniquely identifiable as a fixed recognizable point. In the present specification the term "fiducial location" refers to a useful location to which a fiducial reference is attached. A "fiducial location" will typically be proximate a surgical site. The term "marker" or "tracking marker" refers to an object or reference that may be perceived by a sensor proximate to the location of the surgical or dental procedure, where the sensor may be an optical sensor, a radio frequency identifier (RFID), a sonic motion detector, an ultra-violet or infrared sensor. The term "tracker" refers to a device or system of devices able to determine the location of the markers and their orientation and movement continually in 'real time' during a procedure. As an example of a possible implementation, if the markers are composed of printed targets then the tracker may include a stereo camera pair. In some embodiments, the tracker may be a non-stereo optical tracker, for example a camera. The camera may, for example, operate in the visible or near-infrared range. The term "image information" is used in the present specification to describe information obtained by the tracker, whether optical or otherwise, about one or more tracking markers and usable for determining the location of the markers and their orientation and movement continually in 'real time' during a procedure. The term "vectorized" is used in this specification to describe fiducial keys and tracking markers that are at least one of shaped and marked so as to make their orientation in three dimensions uniquely determinable from their appearance in a scan or in image information. If their three-dimensional orientation is determinable, then their three-dimensional location is also known. The "vectorized" tracking markers and fiducial markers/fiducial keys in this disclosure shall all be understood to have at least one of a rotationally asymmetric shape and a rotationally asymmetric pattern disposed on the tracking marker or on the fiducial key.

All vectorized tracking markers employed in the present invention (for example 504, 507, 607 and 609 of FIG. 5 and FIG. 6, as well as markers 313, 322 and 332 of FIGS. 3K, 3L and 3M, and those shown or referred to below in FIGS. 7-13) may be passive. The term "passive" is used in the present specification to describe markers that do not rely on any own electronic, electrical, optoelectronic, optical, magnetic, wireless, inductive, or other active signaling function or on any incorporated electronic circuit, whether powered or unpowered, to be identified, located, or tracked. The term "own active signaling" is used in this specification to describe a signal that is temporally modulated by, on, or within the tracking marker. The tracking markers do not rely on motion, location, or orientation sensing devices, whether powered or unpowered, to be tracked. They cannot sense their own motion, location, or orientation, nor have they any ability to actively communicate. They bear distinctive markings and/or have distinctive shapes that allow them to be identified, located, and tracked in three dimensions by a separate tracker such as, for example, tracker 610 of FIG. 6, both in their location and in their orientation. In some embodiments, the tracker may be an optical tracker, more particularly, a non-stereo optical tracker. In other embodiments, the tracker may be a stereo tracker. Any one or more of identification, location, and tracking of the markers is solely on the basis of their distinctive markings and/or distinctive shapes. All fiducial references employed in the present invention may also be passive. This specifically includes fiducial references 502 and 602 of FIG. 5 and FIG. 6 respectively, and fiducial references 10, 10', 20, 20' and 20" in FIGS. 3A to 3N.

FIG. 1 is a high-level block diagram of a computing environment 100 according to one embodiment. FIG. 1 illustrates server 110 and three clients 112 connected by network 114. Only three clients 112 are shown in FIG. 1 in order to simplify and clarify the description. Embodiments of the computing environment 100 may have thousands or millions of clients 112 connected to network 114, for example the Internet. Users (not shown) may operate software 116 on one of clients 112 to both send and receive messages network 114 via server 110 and its associated communications equipment and software (not shown).

Figure 2:
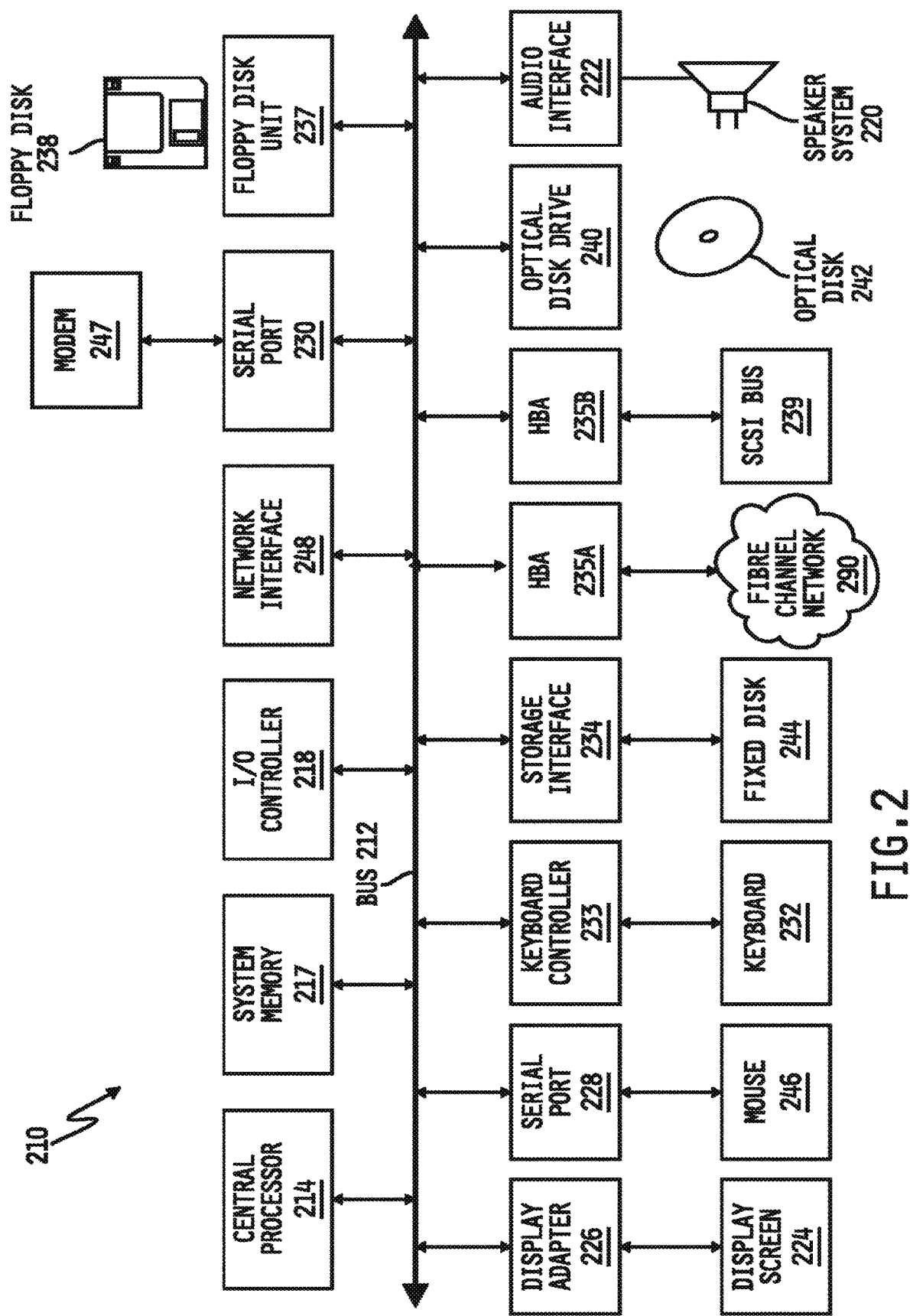
FIG. 2 is a block diagram of a computing system (either a server or client, or both, as appropriate), with optional input devices (e.g., keyboard, mouse, touch screen, etc.) and output devices, hardware, network connections, one or more processors, and memory/storage for data and modules, etc. which may be utilized as controller and display in conjunction with embodiments of the present invention.

FIG. 2 depicts a block diagram of computer system 210 suitable for implementing server 110 or client 112. Computer system 210 includes bus 212 which interconnects major subsystems of computer system 210, such as central processor 214, system memory 217 (typically RAM, but which may also include ROM, flash RAM, or the like), input/output controller 218, external audio device, such as speaker system 220 via audio output interface 222, external device, such as display screen 224 via display adapter 226, serial ports 228 and 230, keyboard 232 (interfaced with keyboard controller 233), storage interface 234, disk drive 237 operative to receive floppy disk 238 (or other suitable portable storage, e.g., a memory stick or card), host bus adapter (HBA) interface card 235A operative to connect with Fiber Channel network 290, host bus adapter (HBA) interface card 235B operative to connect to SCSI bus 239, and optical disk drive 240 operative to receive optical disk 242. Also included are mouse 246 (or other point-and-click device. coupled to bus 212 via serial port 228), modem 247 (coupled to bus 212 via serial port 230), and network interface 248 (coupled directly to bus 212).

Bus 212 allows data communication between central processor 214 and system memory 217, which may include read-only memory (ROM) or flash memory (neither shown), and random access memory (RAM) (not shown), as previously noted. RAM is generally the main memory into which operating system and application programs are loaded. ROM or flash memory may contain, among other software code, Basic Input-Output system (BIOS), which controls basic hardware operation such as interaction with peripheral components. Applications resident with computer system 210 are generally stored on and accessed via computer readable media, such as hard disk drives (e.g., fixed disk 244), optical drives (e.g., optical drive 240), floppy disk unit 237, or other storage medium. Additionally, applications may be in the form of electronic signals modulated in accordance with the application and data communication technology when accessed via network modem 247 or interface 248 or other telecommunications equipment (not shown).

Storage interface 234, as with other storage interfaces of computer system 210, may connect to standard computer readable media for storage and/or retrieval of information, such as fixed disk drive 244. Fixed disk drive 244 may be part of computer system 210 or may be separate and accessed through other interface systems. Modem 247 may provide direct connection to remote servers via telephone link or the Internet via an Internet service provider (ISP) (not shown). Network interface 248 may provide direct connection to remote servers via direct network link to the Internet via a POP (point of presence). Network interface 248 may provide such connection using wireless techniques, including digital cellular telephone connection, Cellular Digital Packet Data (CDPD) connection, digital satellite data connection or the like.

Figure 3A:
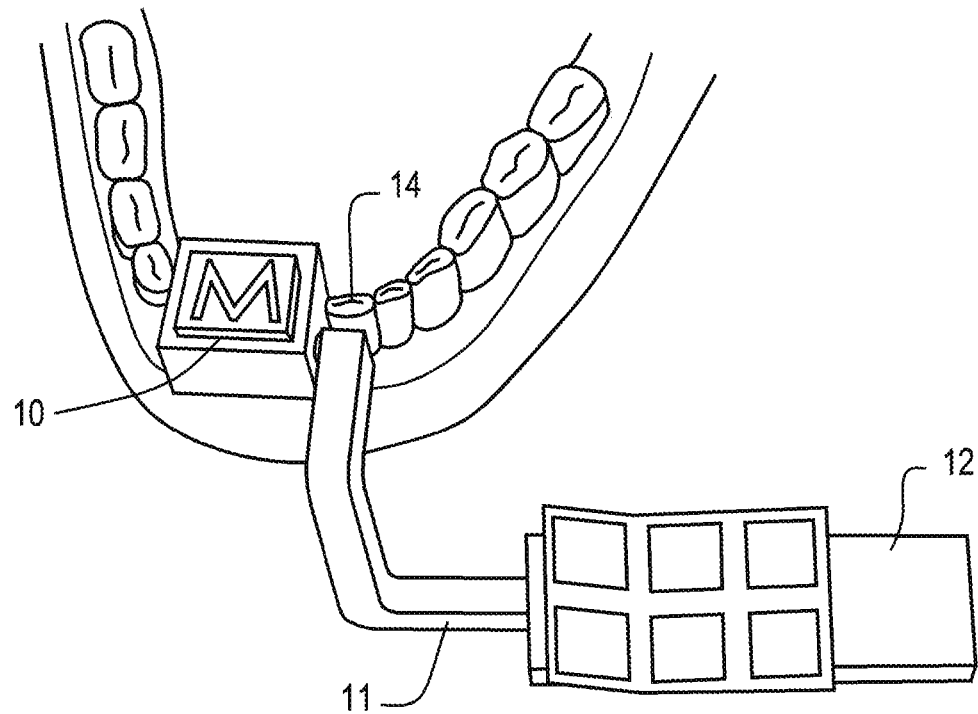
FIGS. 3A-R are drawings of hardware components of the surgical monitoring system and patterns of markings on the components according to embodiments of the invention.
Figure 3B:
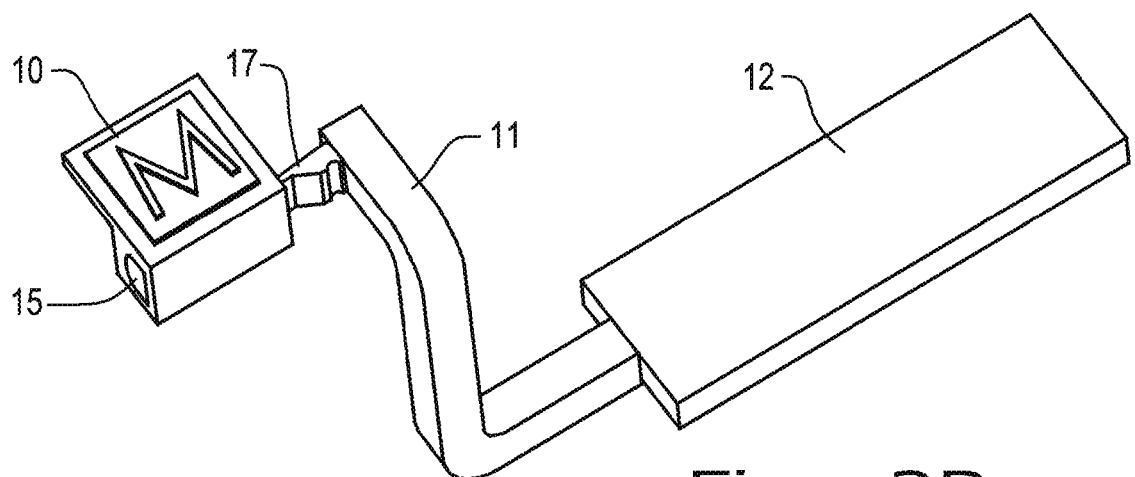
Figure 3C:
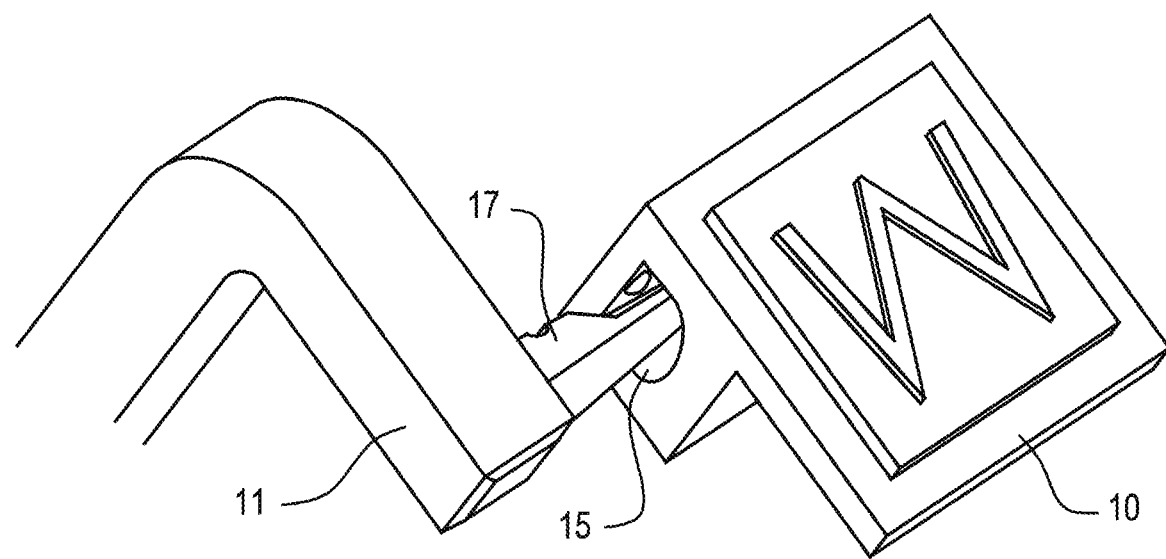
Figure 3D:
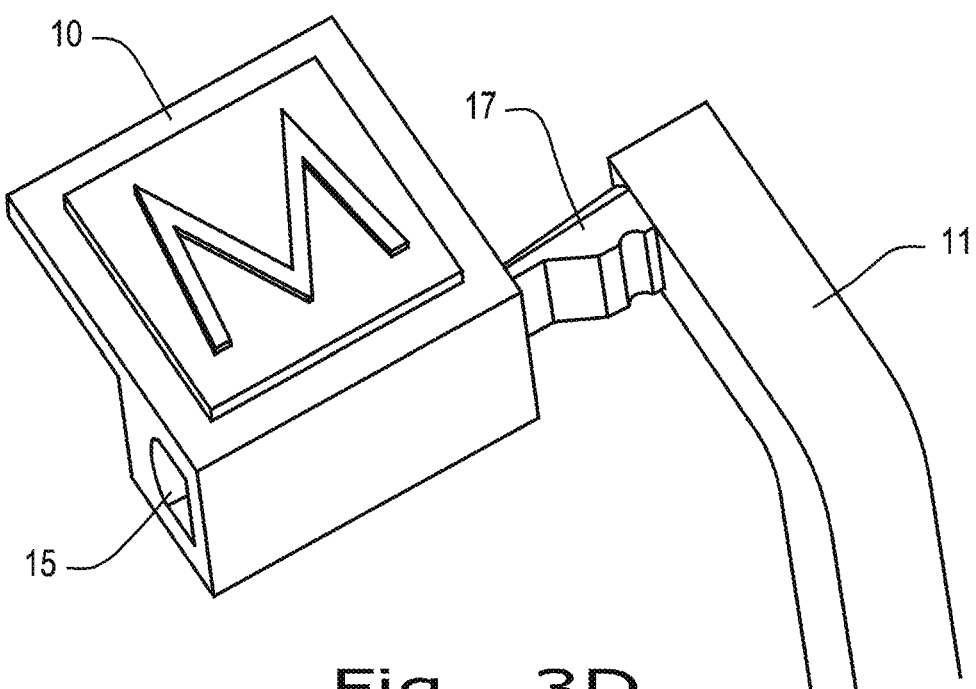
Figure 3E:
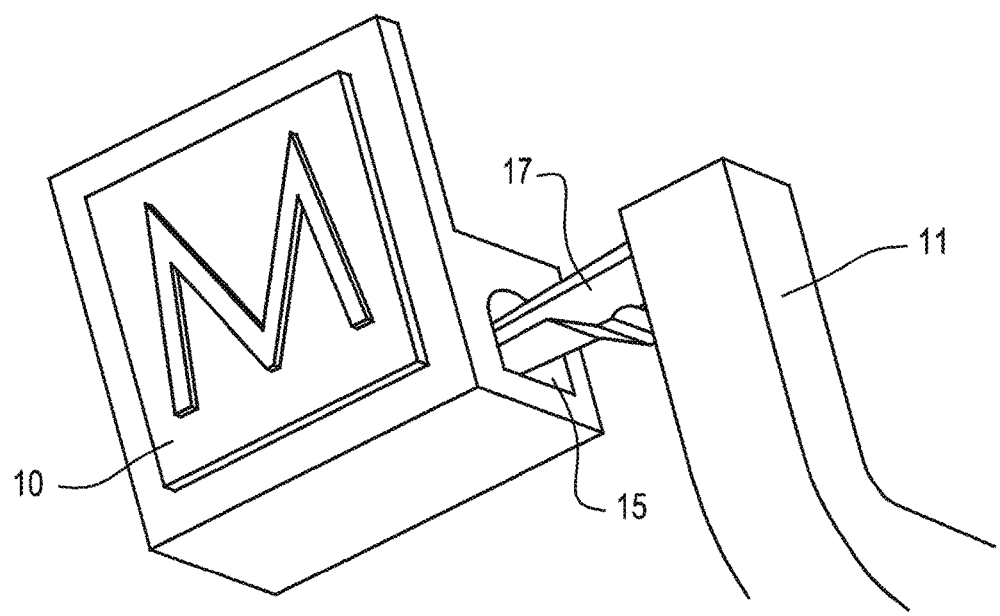
Figure 3F:
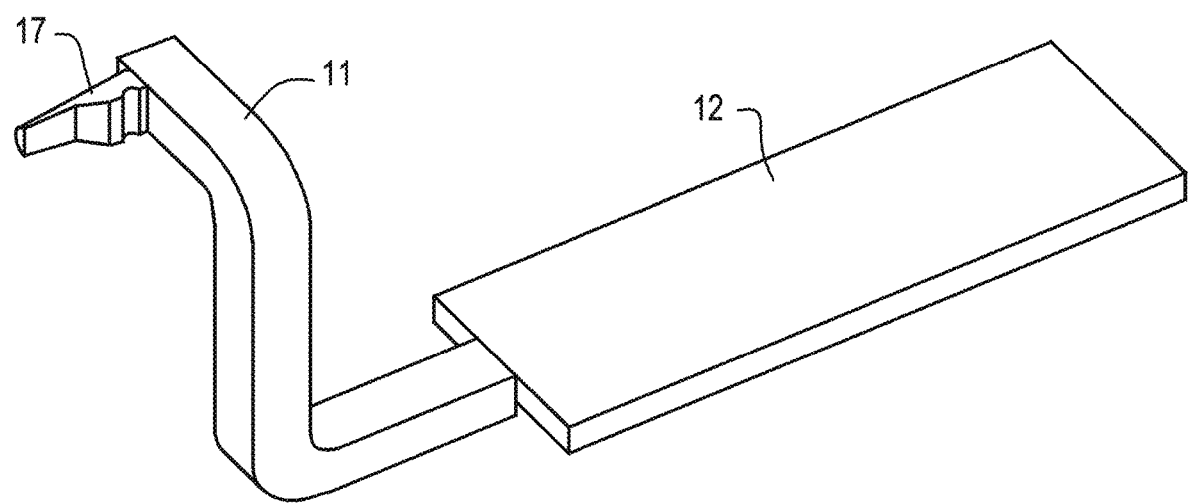
Figure 3G:
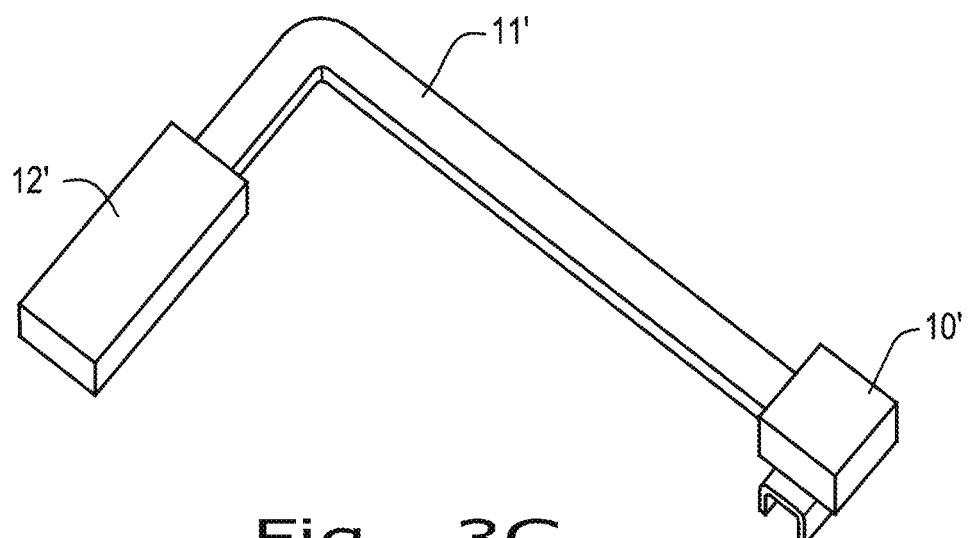
Figure 3H:
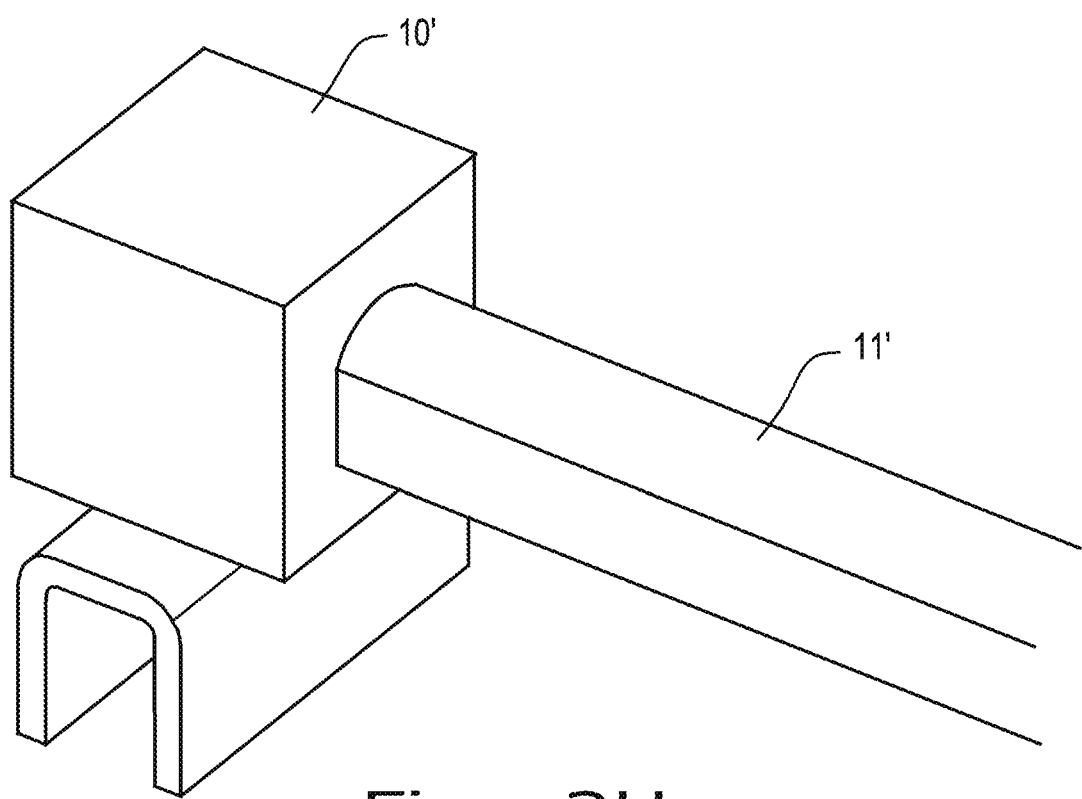
Figure 3I:
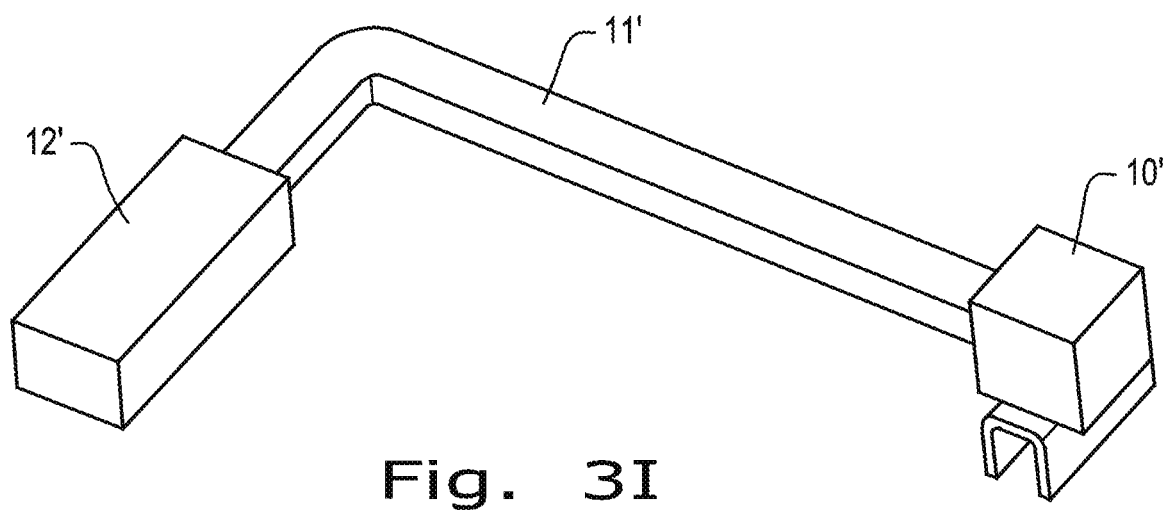
Figure 3J:
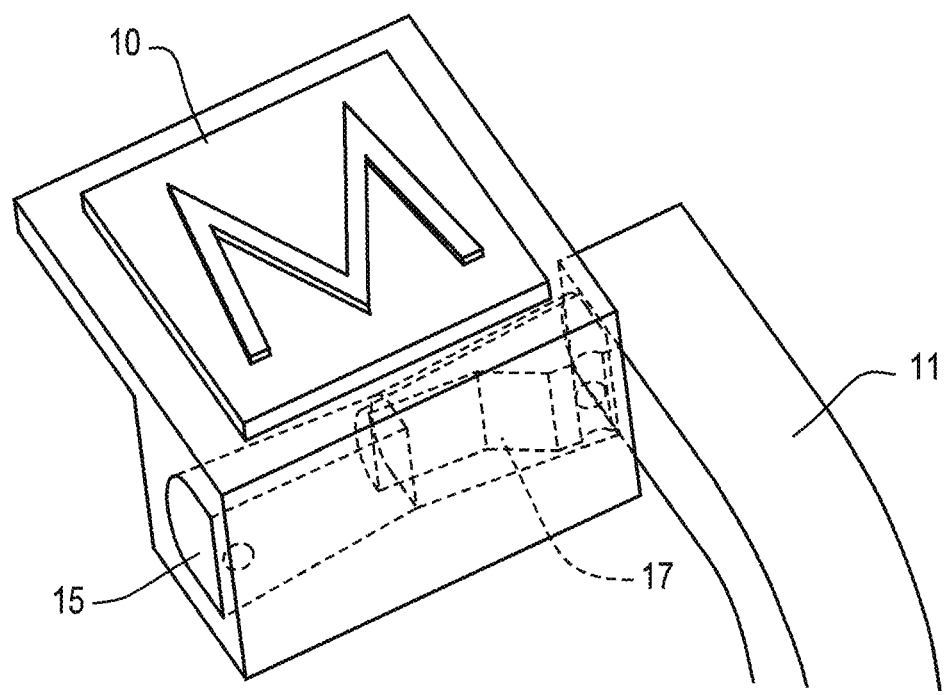
Figure 3K:
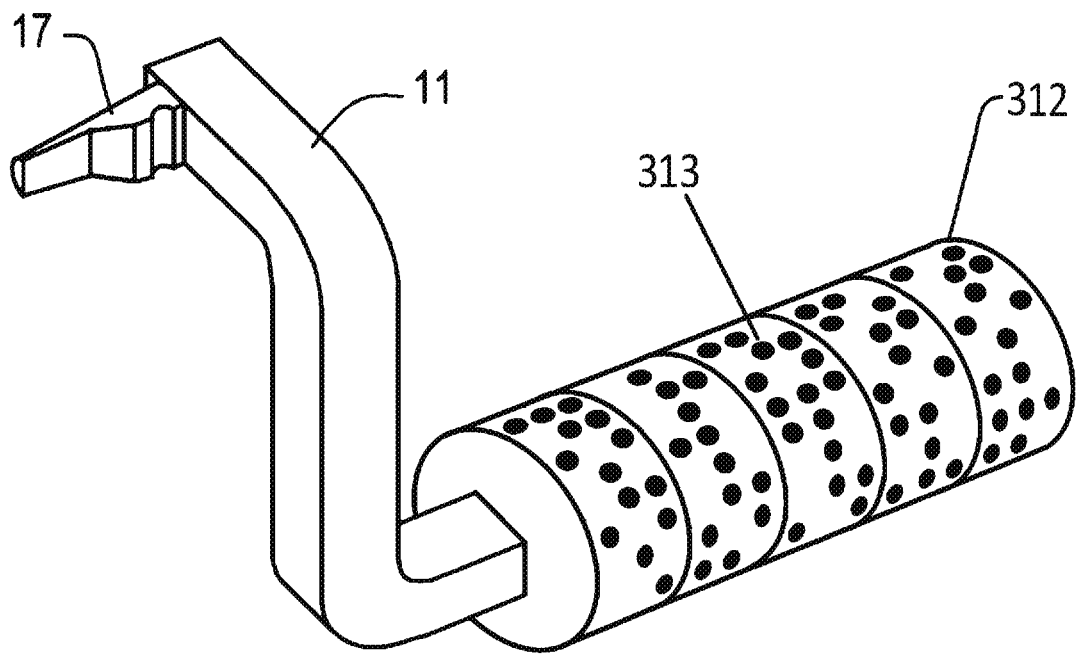
Figure 3L:
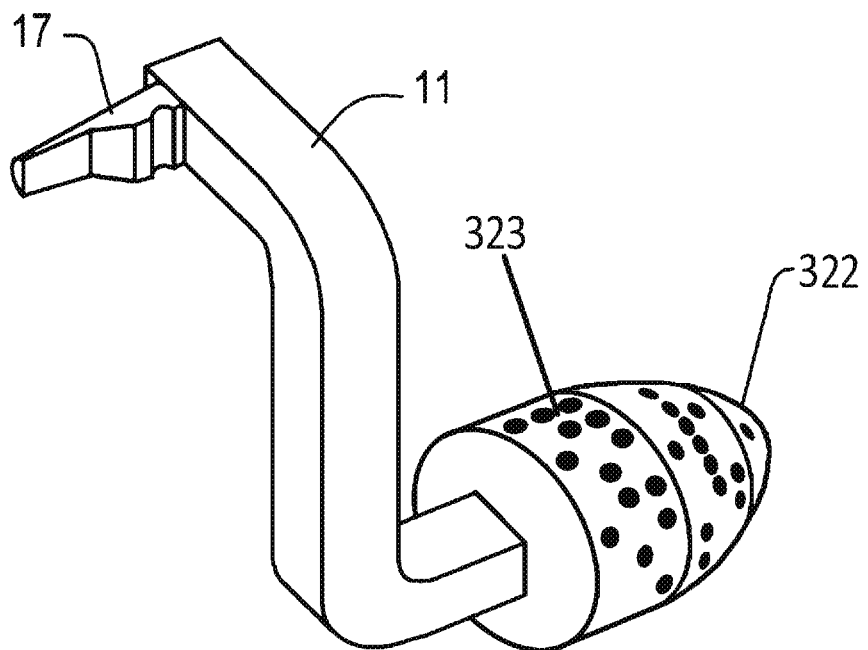
Figure 3M:
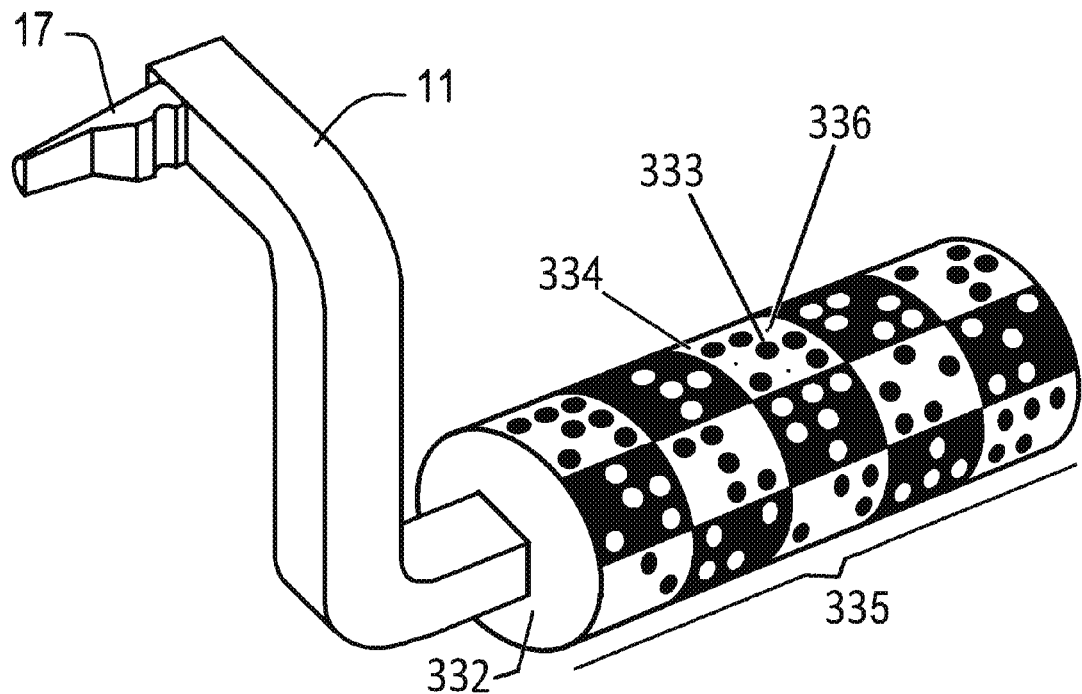
Figure 3N:
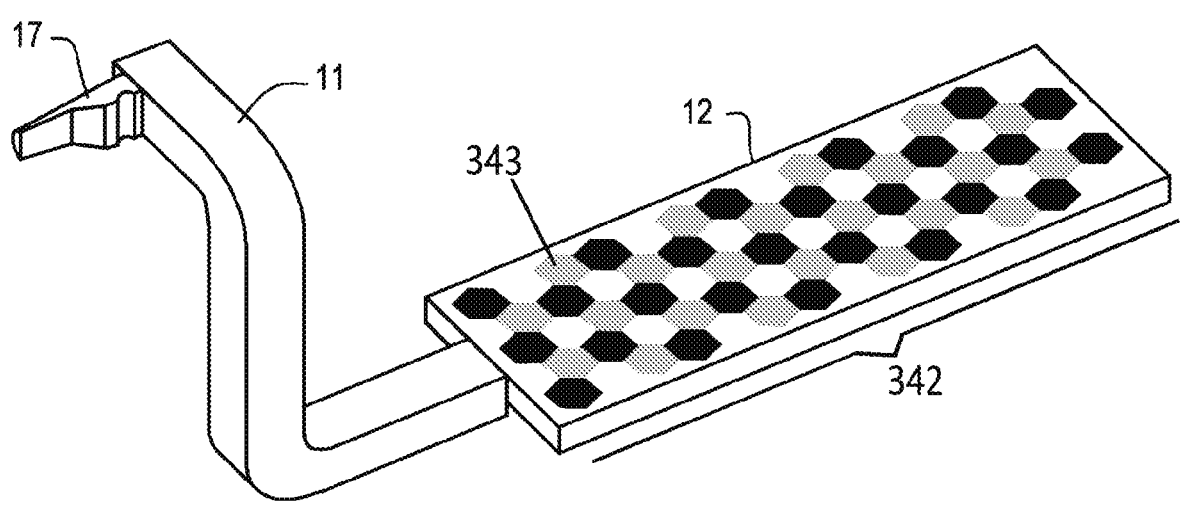

Many other devices or subsystems (not shown) may be connected in a similar manner (e. g., document scanners, digital cameras and so on), including the hardware components of FIGS. 3A-N, which alternatively may be in communication with associated computational resources through local, wide-area, or wireless networks or communications systems. Thus, while the disclosure may generally discuss an embodiment where the hardware components are directly connected to computing resources, one of ordinary skill in this area recognizes that such hardware may be remotely connected with computing resources. Conversely, all of the devices shown in FIG. 2 need not be present to practice the present disclosure. Devices and subsystems may be interconnected in different ways from that shown in FIG. 2. Operation of a computer system such as that shown in FIG. 2 is readily known in the art and is not discussed in detail in this application. Software source and/or object codes to implement the present disclosure may be stored in computer-readable storage media such as one or more of system memory 217, fixed disk 244, optical disk 242, or floppy disk 238. The operating system provided on computer system 210 may be a variety or version of either MS-DOS® (MS-DOS is a registered trademark of Microsoft Corporation of Redmond, Washington), WINDOWS® (WINDOWS is a registered trademark of Microsoft Corporation of Redmond, Washington), OS/2® (OS/2 is a registered trademark of International Business Machines Corporation of Armonk, New York), UN]X® (UNLX is a registered trademark of X/Open Company Limited of Reading, United Kingdom), Linux® (Linux is a registered trademark of Linus Torvalds of Portland, Oregon), or other known or developed operating system.

Moreover, regarding the signals described herein, those skilled in the art recognize that a signal may be directly transmitted from a first block to a second block, or a signal may be modified (e.g., amplified, attenuated, delayed, latched, buffered, inverted, filtered, or otherwise modified) between blocks. Although the signals of the above-described embodiments are characterized as transmitted from one block to the next, other embodiments of the present disclosure may include modified signals in place of such directly transmitted signals as long as the informational and/or functional aspect of the signal is transmitted between blocks. To some extent, a signal input at a second block may be conceptualized as a second signal derived from a first signal output from a first block due to physical limitations of the circuitry involved (e.g., there will inevitably be some attenuation and delay). Therefore, as used herein, a second signal derived from a first signal includes the first signal or any modification to the first signal, whether due to circuit limitations or due to passage through other circuit elements which do not change the informational and/or final functional aspect of the first signal.

The present invention relates to embodiments of surgical hardware and software monitoring systems and methods which allow for surgical planning while the patient is available for surgery, for example while the patient is being prepared for surgery so that the system may model the surgical site. The system uses a particularly configured piece of hardware, namely a vectorized fiducial reference, represented as fiducial key 10 in FIG. 3A, to orient vectorized tracking marker 12 of the monitoring system with regard to the critical area of the surgery. Single fiducial key 10 is attached to a location near the intended surgical area, in the exemplary embodiment of the dental surgical area of FIG. 3A, fiducial key 10 is attached to a dental splint 14. Vectorized tracking marker 12 may be connected to fiducial key 10 by tracking pole 11. In embodiments in which the fiducial reference is directly visible to a suitable tracker (see for example FIG. 5 and FIG. 6) that acquires image information about the surgical site, a tracking marker may be attached directly to the fiducial reference, being fiducial key 10 in the present embodiment. The tracker may be in some embodiments a non-stereo optical tracker. For example, in a dental surgery, dental tracking marker 14 may be used to securely locate fiducial 10 near the surgical area. Single fiducial key 10 may be used as a point of reference, or a fiducial, for the further image processing of data acquired from tracking marker 12 by the tracker. In this arrangement, the fiducial key or reference 10 is scanned not by the tracker, which may for example be an optical tracker, but by a suitable scanning means, which may for example be an X-ray system, CAT scan system, or MRI system as per the definition of "scan" above. In some applications, fiducial key 10 may be disposed in a location or in such orientation as to be at least in part non-visible to the tracker of the system.

In other embodiments additional vectorized tracking markers 12 may be attached to items independent of fiducial key 10 and any of its associated tracking poles 11 or tracking markers 12. This allows the independent items to be tracked by the tracker.

In a further embodiment at least one of the items or instruments near the surgical site may optionally have a tracker attached to function as tracker for the monitoring system of the invention and to thereby sense the orientation and the position of tracking marker 12 and of any other additional vectorized tracking markers relative to the scan data of the surgical area. By way of example, the tracker attached to an instrument may be a miniature digital camera and it may be attached, for example, to a dentist's drill. Any other vectorized markers to be tracked by the tracker attached to the item or instrument must be within the field of view of the tracker.

Using the dental surgery example, the patient is scanned to obtain an initial scan of the surgical site. The particular configuration of single fiducial key 10 allows computer software stored in memory and executed in a suitable controller, for example processor 214 and memory 217 of computer 210 of FIG. 2, to recognize its relative position within the surgical site from the scan data, so that further observations may be made with reference to both the location and orientation of fiducial key 10. In some embodiments, the fiducial reference includes a marking that is apparent as a recognizable identifying symbol when scanned. In other embodiments, the fiducial reference includes a shape that is distinct in the sense that the body apparent on the scan has an asymmetrical form allowing the front, rear, upper, and lower, and left/right defined surfaces that may be unambiguously determined from the analysis of the scan, thereby to allow the determination not only of the location of the fiducial reference, but also of its orientation. That is, the shape and/or markings of the fiducial reference render it vectorized. The marking and/or shape of fiducial key 10 allows it to be used as the single and only fiducial key employed in the surgical hardware and software monitoring system. By comparison, prior art systems typically rely on a plurality of fiducials. Hence, while the tracker may track several vectorized tracking markers within the monitoring system, only a single vectorized fiducial reference or key 10 of known shape or marking is required. By way of example, FIG. 5, later discussed in more detail, shows vectorized marker 504, as well as a vectorized marker 507 on implement 506, being tracked by tracker 508, but there is only one vectorized fiducial reference or key 502 in the system. FIG. 6 similarly shows vectorized marker 604, as well as vectorized markers 607 and 609 on implements 606 and 608 respectively being tracked by tracker 610, while there is only a single vectorized fiducial reference or key 602 in the system.

In addition, the computer software may create a coordinate system for organizing objects in the scan, such as teeth, jaw bone, skin and gum tissue, other surgical instruments, etc. The coordinate system relates the images on the scan to the space around the fiducial and locates the instruments bearing markers both by orientation and position. The model generated by the monitoring system may then be used to check boundary conditions, and in conjunction with the tracker display the arrangement in real time on a suitable display, for example display 224 of FIG. 2 or monitor 530 in FIGS. 5 and 6.

In one embodiment, the computer system has a predetermined knowledge of the physical configuration of single fiducial key 10 and examines slices/sections of the scan to locate fiducial key 10. Locating of fiducial key 10 may be on the basis of its distinct shape, or on the basis of distinctive identifying and orienting markings upon the fiducial key or on attachments to the fiducial key 10 such as tracking marker 12. Fiducial key 10 may be rendered distinctly visible in the scans through higher imaging contrast by the employ of radio-opaque materials or high-density materials in the construction of the fiducial key 10. In other embodiments the material of the distinctive identifying and orienting markings may be created using suitable high density or radio-opaque inks or materials. In the present specification, the term "scan-visible" is used to describe the characteristic of fiducial key 10 by which it is rendered visible in a scan, while not necessarily otherwise visible to the human eye or optical sensor.

Once fiducial key 10 is identified, the location and orientation of the fiducial key 10 is determined from the scan segments, and a point within fiducial key 10 is assigned as the center of the coordinate system. The point so chosen may be chosen arbitrarily, or the choice may be based on some useful criterion. A model is then derived in the form of a transformation matrix to relate the fiducial system, being fiducial key 10 in one particular embodiment, to the coordinate system of the surgical site. The resulting virtual construct may be used by surgical procedure planning software for virtual modeling of the contemplated procedure, and may alternatively be used by instrumentation software for the configuration of the instrument, for providing imaging assistance for surgical software, and/or for plotting trajectories for the conduct of the surgical procedure.

In some embodiments, the monitoring hardware includes a tracking attachment to the fiducial reference. In the embodiment pertaining to dental surgery the tracking attachment to fiducial key 10 is tracking marker 12, which is attached to fiducial key 10 via tracking pole 11. Tracking marker 12 may have a particular identifying pattern, described in more detail later at the hand of FIGS. 7-10. The trackable attachment, for example tracking marker 12, and even associated tracking pole 11 may have known configurations so that observational data from tracking pole 11 and/or tracking marker 12 may be precisely mapped to the coordinate system, and thus progress of the surgical procedure may be monitored and recorded. For example, as particularly shown in FIG. 3J, fiducial key 10 may have hole 15 in a predetermined location specially adapted for engagement with insert 17 of tracking pole 11. In such an arrangement, for example, tracking poles 11 may be attached with a low force push into hole 15 of fiducial key 10, and an audible haptic notification may thus be given upon successful completion of the attachment.

It is further possible to reorient the tracking pole during a surgical procedure. Such reorientation may be in order to change the location of the procedure, for example where a dental surgery deals with teeth on the opposite side of the mouth, where a surgeon switches hands, and/or where a second surgeon performs a portion of the procedure. For example, the movement of the tracking pole may trigger a re-registration of the tracking pole with relation to the coordinate system, so that the locations may be accordingly adjusted. Such a re-registration may be automatically initiated when, for example in the case of the dental surgery embodiment, tracking pole 11 With its attached tracking marker 12 are removed from hole 15 of fiducial key 10 and another tracking marker with its associated tracking pole is connected to an alternative hole on fiducial key 10. Additionally, boundary conditions may be implemented in the software so that the user is notified when observational data approaches and/or enters the boundary areas.

Trackers 508, 610 of the systems and methods disclosed herein may comprise a single optical imager obtaining a two-dimensional image of the site being monitored. The system and method described in the present specification allow three-dimensional locations and orientations of tracking markers to be obtained using non-stereo-pair two-dimensional imagery. In some embodiments more than one imager may be employed as tracker, but the image information required and employed is nevertheless two-dimensional. Therefore, the two imagers may merely be employed to secure different perspective views of the site, each imager rendering a two-dimensional image that is not part of a stereo pair. This does not exclude the employment of stereo-imagers in obtaining the image information about the site, but the system and method are not reliant on stereo imagery of the site in order to identify and track any of the passive vectorized tracking markers employed in the present invention. By virtue of their shapes or markings, the three-dimensional locations and orientations of the tracking markers may be completely determined from a single two-dimensional image of the field of view of the tracker.

In a further embodiment, the vectorized tracking markers may specifically have an identifiably unique three-dimensional shape. Suitable three-dimensional shapes may include, without limitation, a segment of an ellipsoid surface and a segment of a cylindrical surface. In general, suitable three-dimensional shapes are shapes that are mathematically describable by simple functions. One particular three-dimensional surface suitable for use as marker 312 in this embodiment is a cylindrical surface, as shown in FIG. 3K. A cylindrical surface is mathematically described by a simple function. Pattern 313 is rotationally asymmetric, so that rotating cylindrically shaped marker 312 never causes pattern 313 to repeat itself spatially. This allows the position and orientation of marker 312 to be uniquely determined, rendering marker 312 vectorized. Pattern 313 may be present over any useful segment of the surface of marker 312, and may extend around the full circular perimeter of marker 312, thereby allowing a suitable tracker (not shown) to always have a portion of pattern 313 in its view, irrespective of the orientation of position of marker 312. Marker 312 may engage with tracking pole 11 in exactly the same way as already described in the case of markers 12. In FIG. 3K, marker 312 is shown as comprising of five rings of patterns which, together, comprise pattern 313. In other embodiments marker 312 may comprise a single ring bearing a suitably rotationally asymmetric pattern 313 and marker 312 may thereby be simple ring bearing pattern 313.

Further embodiments of suitable vectorized tracking markers bearing rotationally asymmetric patterns are described later at the hand of FIGS. 7-10. The contrast aspects discussed below at the hand of FIGS. 7-10 also apply to pattern 313 in FIG. 3K in that the contrasting portions of pattern 313 may have perimeters comprising a mathematically describable curved sections to provide suitable pattern tags. More detail in this regard is provided below.

In another embodiment, a suitable segment of a three-dimensional surface for use as a pattern bearing surface for a marker is an ellipsoid surface. Ellipsoids are describable by simple mathematical functions, of which a spherical surface is the most simple. FIG. 3L shows vectorized tracking marker 322 having ellipsoid surface bearing pattern 323. Marker 322 may be used in the same fashion as marker 312, or the markers of FIGS. 7-10.

In both FIG. 3K and FIG. 3L patterns 313 and 323 respectively are shown as black circular areas on a white background. In other embodiments, the circular contrast areas may be white and the background color may be black.

Yet a further embodiment is shown in FIG. 3M, based on the design of FIG. 3K. Vectorized tracking marker 332 has close-packed tiled background 335, which in this embodiment is a square checkerboard background. Within square checkerboard background 335 of FIG. 3M, any given tile has a first color, and the immediate neighbor tile sharing a border with the given tile has a second color, the entire square checkerboard background comprising the two colors. By way of example in FIG. 3M, if a given tile 334 comprises contrasting black pattern elements 333 on a white background unit cell, then all of its border-sharing neighbors of tile 334 comprise white contrasting pattern elements on a black background. The arrangement of contrasting pattern elements 333 is specifically rotationally asymmetric.

The square checkerboard background of FIG. 3M is one specific example of a more general class of close-packed tiled backgrounds that may be employed. In a more general embodiment, the background may be a more general close-packed tiled background based on close-packing tiles. Examples of suitable close-packing tiles include, without limitation, squares, rectangles, parallelograms, hexagons, and slanted hexagons. To the extent that combinations of suitably rotated triangles may be used to form squares, rectangles, parallelograms and hexagons, triangles may also be employed as tiles or unit cells in these general embodiments. The term "tile" refers to a portion of a surface with borders, generally in a geometric shape. The term "close-packed" does not require that the tiles do not overlap or have no gaps therebetween, rather the term close-packed indicates arrangements which allow the tiles to generally cover a marker with a predetermined geometric configuration. By way of example, FIG. 3N shows marker 12 bearing hexagonal close-packed tiled background 342 based on hexagon unit cells 343 and uses three mutually contrasting tile colors, as applied to marker 12 of FIG. 3F. Yet further suitably contrasting colors may be employed for the contrasting pattern elements to be borne by the background. All the mutually contrasting colors are chosen to be discernible from one another by the tracker, which may be a non-stereo optical tracker. For the sake of clarity, no contrasting pattern elements are shown in FIG. 3N. In other embodiments, the tiles in the close-packed tiled background may be of differing shapes.

In the case of hexagonal unit cells 343, shown in hexagonal close-packed tiled background 342 of FIG. 3N, each given unit cell has six nearest neighbors sharing a border. In the case of such a hexagon-based implementation, a suitably close-packed tiled background may be obtained by assigning three differing colors to the background cells such that each background cell of a first color has three border-sharing nearest neighbor cells of a second contrasting color and three border-sharing nearest neighbor cells of a third contrasting color. There is only one close-packed tiled background of hexagonal unit cells 343 complying with these conditions, and it is shown in FIG. 3N, employing three mutually contrasting colors. Any arrangement of contrasting pattern elements (not shown in FIG. 3N) that may be applied to background 342 is selected to specifically have no rotational symmetry.

Returning to FIG. 3M, the presence of background 335 obviates the need for clear borders of finite width between tiles 334, whilst nevertheless demarcating the same border by virtue of the contrast between tiles 334. This saves critical space on vectorized marker 332 by allowing the overall pattern to be fashioned in greater density. This in turn allows a larger portion of the pattern to be viewable by the tracker of the system, for example, trackers 508 and 610 of FIGS. 5 and 6 respectively, which may be, in one embodiment, non-stereo optical trackers. A larger number of tiles 334 viewable by the tracker at any one time assures that contrasting pattern elements 333 may be identified and located with great certainty and accuracy. To the degree that close-packed tiled background 335 is identifiable by the tracker, and because expected positions 336 of present or absent contrasting pattern elements 333 relative to the borders of tiles 334 are known to the controller of the system, close-packed tiled background 335 also allows contrasting pattern elements 333 to be correctly identified and differentiated from any system noise. Over and above the benefits of close-packed tiled background 335 all the aspects and benefits described at the hand of FIGS. 7-10 below may also apply to the embodiment of FIG. 3M, in that contrasting pattern elements 333 may have specific mathematically describable curved sections as perimeters. The curved sections may constitute less than the entire perimeter and the curve may be, for example, without limitation, conic sections. In yet further embodiments the curves may be mathematically describable curves other than conic sections. Contrasting pattern elements 333 may be round dots having color contrast with respect to tiles 334 on which they are disposed.

In operation, the tracker of the system (for example, trackers 508 and 610 of FIGS. 5 and 6 respectively) gathers image information of the surgical area, including image information of vectorized tracking marker 332. Close-packed tiled background 335 may be stored in memory as one of many possible close-packed tiled backgrounds in that memory, for example memory 217 of system 210 in FIG. 2. Along with close-packed background unit cell structure 335, expected positions 336 of contrasting pattern elements 333 (whether present or not), may be stored in memory 217, either as graphic positions or as mathematical formulae expressed relative to the easily identifiable borders of tiles 334. Unit cells of pattern 335 bear contrasting pattern elements 333 only at the known grid positions within unit cells 334.

Given that the borders of unit cells 334 are unequivocally identifiable in the image information, the system controller, for example central processor 214 of FIG. 2, only has to concern itself with contrast information at expected positions 336 and may disregard other contrast information within unit cell 334 as noise. With the pattern repeated across the surface of tracking marker 334, the system as a whole benefits from the statistical addition of contrast information. To the extent that a portion of pattern 335 may be obscured at times, the repetition of the pattern ensures that some portion of pattern 335 is always in view of the tracker and information about pattern 335 and contrasting pattern elements 333 may always be included by tracker 504 in the image information of the surgical site.

Figure 3P:
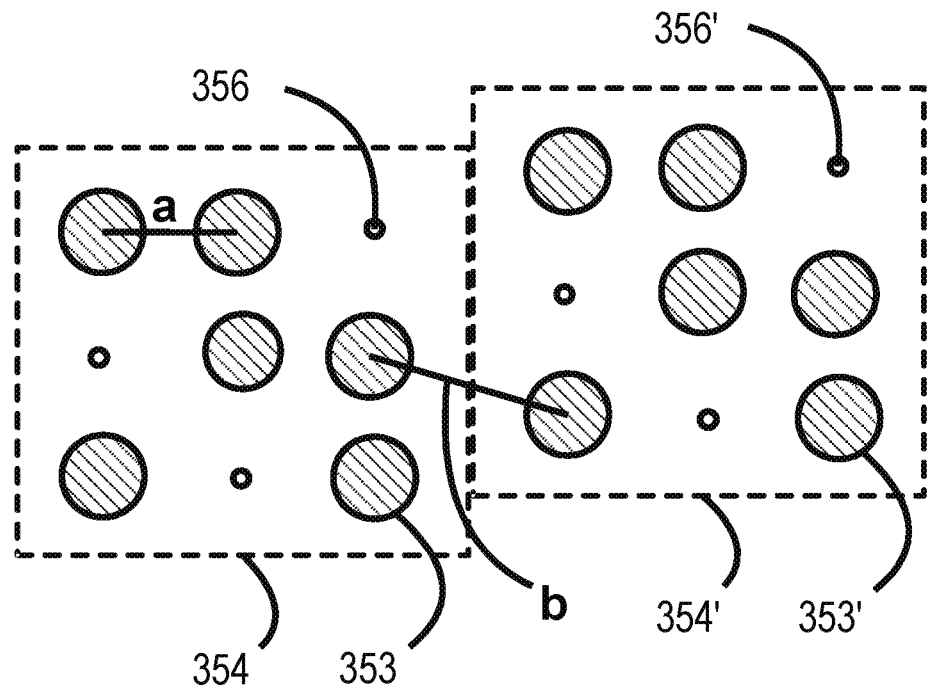

FIG. 3P shows another embodiment in which no patterned background is employed. The background is un-patterned and non-demarcating means have to be employed to identify a unit cell of the pattern. In the present specification the term "undemarcated pattern" is used to refer to a pattern such as that in FIG. 3P that is not confined by any border that demarcates the extent of a unit cell of the pattern. An undemarcated pattern therefore is a pattern that has to be identified solely on the basis of the spatial juxtaposition of its constituent elements. In other words, undemarcated patterns have to be identified solely on the basis of the mutual arrangement of their constituent elements with respect to one another. Means other than a border have to be employed to recognize unit cells of undemarcated patterns. For the sake of clarity, the pattern in FIG. 3P is shown in two dimensions, even though the vectorized marker on which it is established may have a three-dimensional surface, such as for example, marker 322 of, FIG. 3L. The undemarcated pattern in FIG. 3P is also shown enlarged.

In one non-limiting example implementation, shown in FIG. 3P, the center-to-center distances of pattern elements (for example circular dots 353) in unit cell 354 may be restricted to a limited set of predetermined distances derived from the pattern of unit cell 354. The limited set of predetermined distances may be, for example, a set of distances derived geometrically from the center-to-center distance a between two closest neighbor elements 353 within the pattern. All possible locations 356 that may be occupied by dots in pattern unit cell 354, whether actually so occupied or not, may be geometrically derived from the nearest neighbor center-to-center distance a. To differentiate dots 353 in unit cell 354 from dots 353' belonging to another unit cell, for example unit cell 354', dots 353' belonging to unit cell 354' need merely be, as shown in FIG. 3P, separated from selected dot 353 by distances b not in the limited set of predetermined distances. Occupiable location 356 of unit cell 354 may be differentiated from occupiable locations 356' of unit cell 354' by the same method. In this arrangement, the need for a contrast in background color between adjacent unit cells is obviated. No demarcation boundary between unit cell 353 and unit cell 354' is required at all. The software in the controller of the system need merely determine the distances between dots in order to ascertain which dots belong in one unit cell and which belong in a potentially confusing nearby unit cell. A given pattern in a first unit cell may be employed to derive a neighboring pattern and unit cell by, for example, displacing the derived pattern from the given one parallel to a line (for example a) between nearest neighbor occupiable locations by a distance that is not identical to or a multiple of the center-to center distance a. The two patterns may additionally be mutually displaced perpendicular to that line by a distance that is not identical to or a multiple of the center-to-center distance a.

In yet further embodiments, other graphic or geometric methods may be employed to differentiate uniquely between different units cells of a dot pattern on vectorized tracking markers. Methods for separating such patterns and identifying pattern elements belonging uniquely to a particular pattern are well-established in the general field of image and pattern recognition, and need not be further elucidated here. These embodiments obviate the need for any contrast in background color between adjacent unit cells and unit cells are recognized by the tracker of the system purely on the basis of patterns of elements in the unit cell. While, in some embodiments, there may be a single unit cell of a pattern on a tracking marker, other embodiments may employ tracking markers that have a plurality of unit cells of the pattern and even unit cells of more than one pattern.

In some embodiments, different unit cells 354 and 354' may contain differing patterns in that different combinations of occupiable locations are occupied in the different unit cells. In other embodiments, all unit cells contain the same pattern. The system may treat clusters of unit cells as a single pattern. As in the examples of FIGS. 3K, 3L, and 3M, patterns within unit cell cells 354 and 354' may be rotationally asymmetric. No rotation of extent smaller than 360 degrees may cause such rotationally asymmetric patterns to repeat. As in the embodiments described above, the pattern elements represented by solid circular elements 353 and 353' of FIG. 3P, are contrasting areas which may have perimeters other than circular. The perimeters may comprise mathematically describable curved sections. The curved sections may constitute less than the entire perimeter and the curves may be, for example, without limitation, conic sections. In yet further embodiments the curves may be mathematically describable curves other than conic sections. The benefits of employing curved sections are discussed in more depth below.

Figure 3Q:
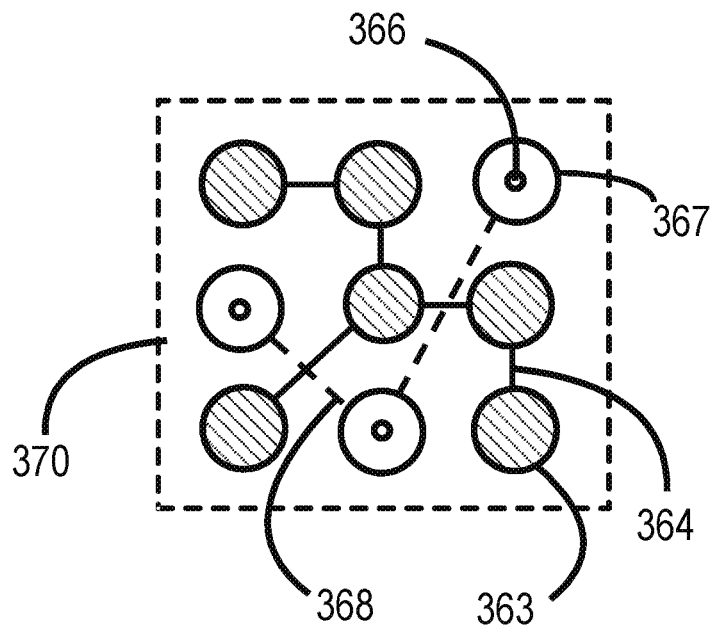

In yet further embodiments, for example the embodiment shown in FIG. 3Q, a tracking marker may bear first pattern 364 comprising pattern elements 363. Pattern 364 is indicated with solid lines in FIG. 3Q. To this extent, the tracking marker may be a tracking marker identical to the one bearing pattern 354 of FIG. 3P. However, whereas occupiable locations 356 of unit cell 354 in FIG. 3P do not bear any pattern elements, corresponding occupiable locations 366 in FIG. 3Q bear pattern elements 367 which, collectively, constitute identifiably unique second pattern 368. The term "identifiably unique" is employed in the present specification to describe a pattern that is distinct from patterns on any other tags employed with the system and may be uniquely identified with a particular tracking marker for the purposes of identifying the marker, both when it is used alone and when used in conjunction with other pattern-bearing tracking markers. Pattern 368 is indicated using broken lines in FIG. 3Q. In FIG. 3Q, elements 367 are differentiated from elements 363 on the basis of shape, but in general any other means or combination of means of differentiation may be employed, including without limitation, color, solidity (empty versus solid shapes of the same outline), differing geometric shapes, differing mathematical descriptions of their perimeters, and the like. First pattern 364 may be employed to ascertain the three-dimensional location and orientation of the marker bearing the two patterns, whereas the identifiably unique second pattern 368 may be employed to uniquely identify the tag. In some implementations, one of the two patterns, for example pattern 368, may be employed to uniquely identify the marker, while patterns 368 and 364 together, constituting joint pattern 370, may be employed to determine the three-dimensional location and orientation of the marker bearing the two patterns 364 and 368.

Figure 5:
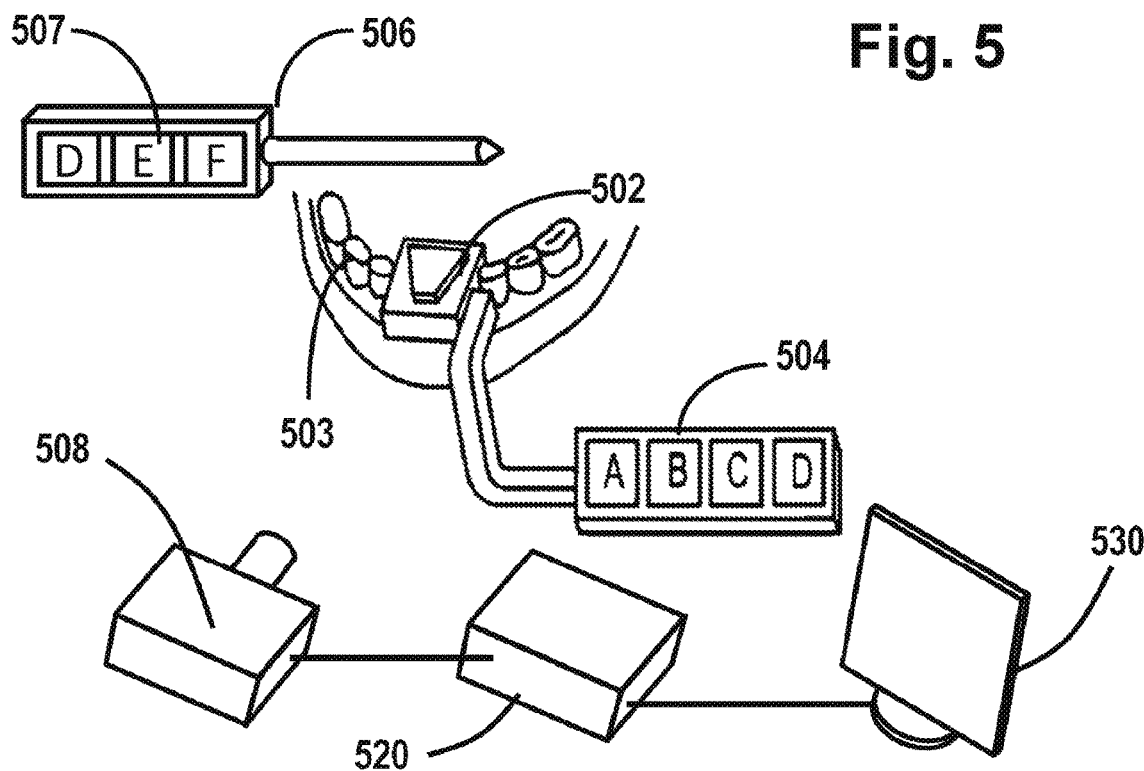
FIG. 5 is a drawing of a dental passive vectorized fiducial key with a tracking pole and a dental drill according to one embodiment of the present invention.
Figure 6:
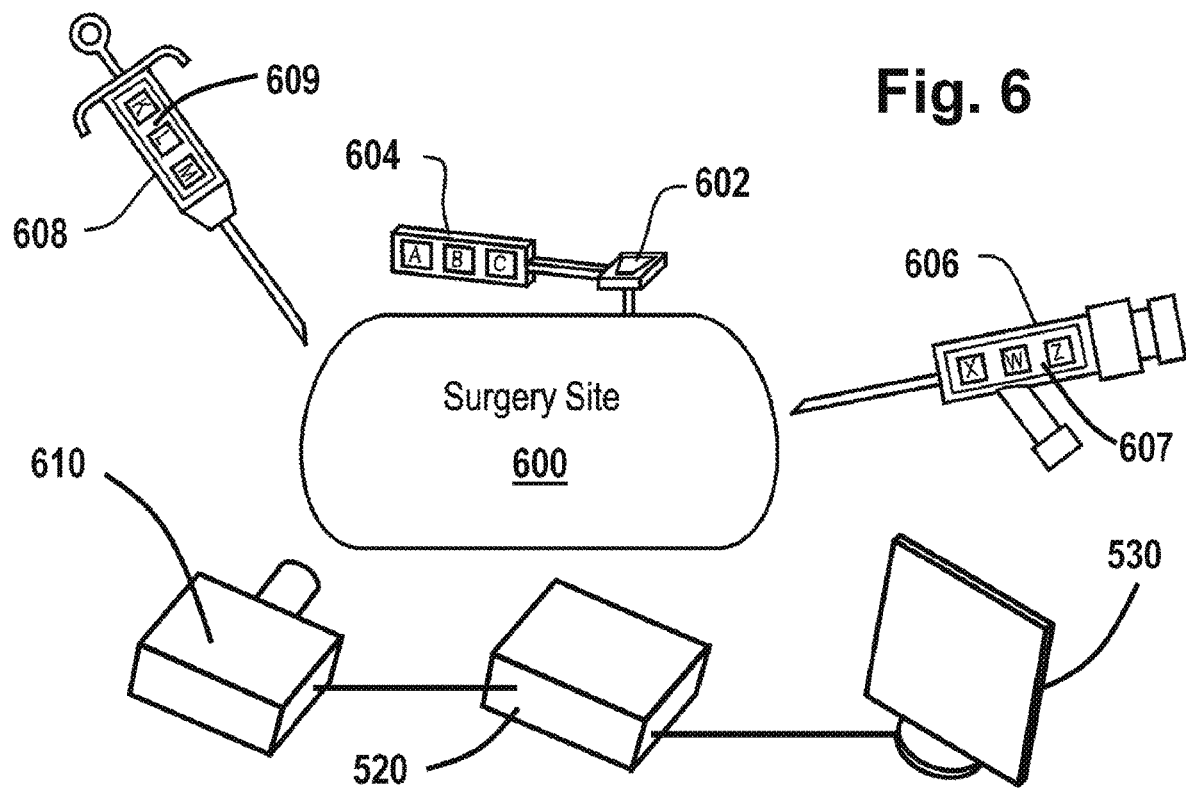
FIG. 6 is a drawing of an endoscopic surgical site showing the passive vectorized fiducial key, endoscope, and biopsy needle according to another embodiment of the invention.

As long as elements 363 and 367 are mutually discernible by the controller and tracker of the system together, for example controller 520 of FIGS. 5 and 6 and tracker 508 of FIG. 5 or tracker 610 of FIG. 6, collective pattern 370 formed by patterns 364 and 368 together retains its asymmetric nature if one of pattern 364 or pattern 368 is rotationally asymmetric. This allows the unique determination of the location and orientation of the marker, but has the added benefit of having more elements available than the implementation of FIG. 3P. This provides greater accuracy in the determination of the location and orientation of the marker. Given that there is practical merit in not making the markers large, this approach also has the benefit of not wasting any precious space between elements.

The combined pattern 370 formed by patterns 364 and 368 together may be considered to be a single pattern comprising first 364 and second 368 mutually discernible subsets of elements, second subset 368 of elements 367 employed to uniquely identify the marker and first subset 364 of elements 363 being rotationally asymmetric. This renders combined pattern 370 rotationally asymmetric and provides a large number of elements (363 and 367 together) to serve as basis of a more accurate determination of location and orientation of the marker without sacrificing space on the marker.

The marker may be described as bearing a rotationally asymmetrical pattern (364 and 368 together) comprising first plurality 364 of first pattern elements 363 and second plurality 368 of second pattern elements 367, first elements 363 and second elements 367 being mutually discernible. The rotationally asymmetric pattern may be geometrically close packed and its rotational asymmetry may be exclusively due to the mutual discernibility of elements 363 and 367. To improve accuracy in the determination of the orientation of the marker, patterns 354 and 368 may be repeated on the marker.

Figure 3R:
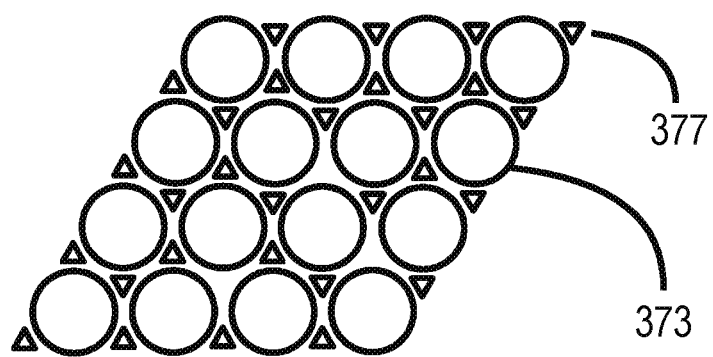

In FIG. 3Q, two circular elements are employed; one (363) being solid and the other (367) being of empty circular structure. However, in a more general case, the mutually discernible elements need not be of equal size. This is important in close packed structures, where the interstitial space is limited. By selecting the two mutually discernible elements to be of significantly different sizes, the one set may be interstitially arranged with respect to the other. FIG. 3R provides an example of such an arrangement. Practitioners in the field will recognize the pattern formed by circular elements 373 as being a classic close-packed structure. Given that elements 373 are circular in this example, they will leave interstitial areas between the elements. Significantly smaller triangular elements 377 may occupy the spaces in a second pattern. While the pattern of elements 373 has a 60 degree rotational symmetry, the fact that some triangular elements 373 are absent destroys the rotational symmetry and makes possible a completely unique determination of location and orientation of any marker bearing the pattern. The centers of both elements 373 and elements 377 may be determined with great accuracy, given that their perimeters are mathematically well-defined. In more general implementations other element shapes may be employed.

In yet further examples more than two different element shapes may be employed in more than two corresponding patterns. To ensure that the orientation is uniquely determined, only the resultant overall pattern needs to be rotationally asymmetrical. This may in some examples be achieved by combining patterns that individually have rotational symmetry, but lack any rotational symmetry when combined.

In a further embodiment of the system utilizing the invention, a surgical instrument or implement, herein termed a "hand piece" (see FIGS. 5 and 6), may also have a particular configuration that may be located and tracked in the coordinate system and may have suitable tracking markers as described herein. A boundary condition may be set up to indicate a potential collision with virtual material, so that when the hand piece is sensed to approach the boundary condition an indication may appear on a screen, or an alarm sound. Further, target boundary conditions may be set up to indicate the desired surgical area, so that when the trajectory of the hand piece is trending outside the target area an indication may appear on screen or an alarm sound indicating that the hand piece is deviating from its desired path.

An alternative embodiment of some hardware components is shown in FIGS. 3G-I. Vectorized fiducial key 10' has connection elements with suitable connecting portions to allow tracking pole 11' to position tracking marker 12' relative to the surgical site. Conceptually, fiducial key 10' serves as an anchor for pole 11' and tracking marker 12' in much the same way as the earlier embodiment, although it has a distinct shape. The software of the monitoring system is pre-programmed with the configuration of each particularly identified fiducial key, tracking pole, and tracking marker, so that the location calculations are only changed according to the changed configuration parameters.

The materials of the hardware components may vary according to regulatory requirements and practical considerations. Generally, the key or fiducial component is made of generally radio opaque material such that it does not produce noise for the scan, yet creates recognizable contrast on the scanned image so that any identifying pattern associated with it may be recognized. In addition, because it is generally located on the patient, the material should be lightweight and suitable for connection to an apparatus on the patient. For example, in the dental surgery example, the materials of the fiducial key must be suitable for connection to a plastic splint and suitable for connection to a tracking pole. In the surgical example the materials of the fiducial key may be suitable for attachment to the skin or other particular tissue of a patient.

The vectorized tracking markers may be clearly identified by employing, for example without limitation, high contrast pattern engraving. The materials of the tracking markers are chosen to be capable of resisting damage in autoclave processes and are compatible with rigid, repeatable, and quick connection to a connector structure. The tracking markers and associated tracking poles have the ability to be accommodated at different locations for different surgery locations, and, like the fiducial keys, they should also be relatively lightweight as they will often be resting on or against the patient. The tracking poles must similarly be compatible with autoclave processes and have connectors of a form shared among tracking poles.

The tracker employed in tracking the fiducial keys, tracking poles and tracking markers should be capable of tracking with suitable accuracy objects of a size of the order of 1.5 square centimeters. While the tracker is generally connected by wire to a computing device to read the sensory input, it may optionally have wireless connectivity to transmit the sensory data to a computing device. The tracker may be a non-stereo optical tracker.

In embodiments that additionally employ a trackable piece of instrumentation, such as a hand piece, vectorized tracking markers attached to such a trackable piece of instrumentation may also be light-weight; capable of operating in a 3 object array with 90 degrees relationship; optionally having a high contrast pattern engraving and a rigid, quick mounting mechanism to a standard hand piece.

Figure 4A:
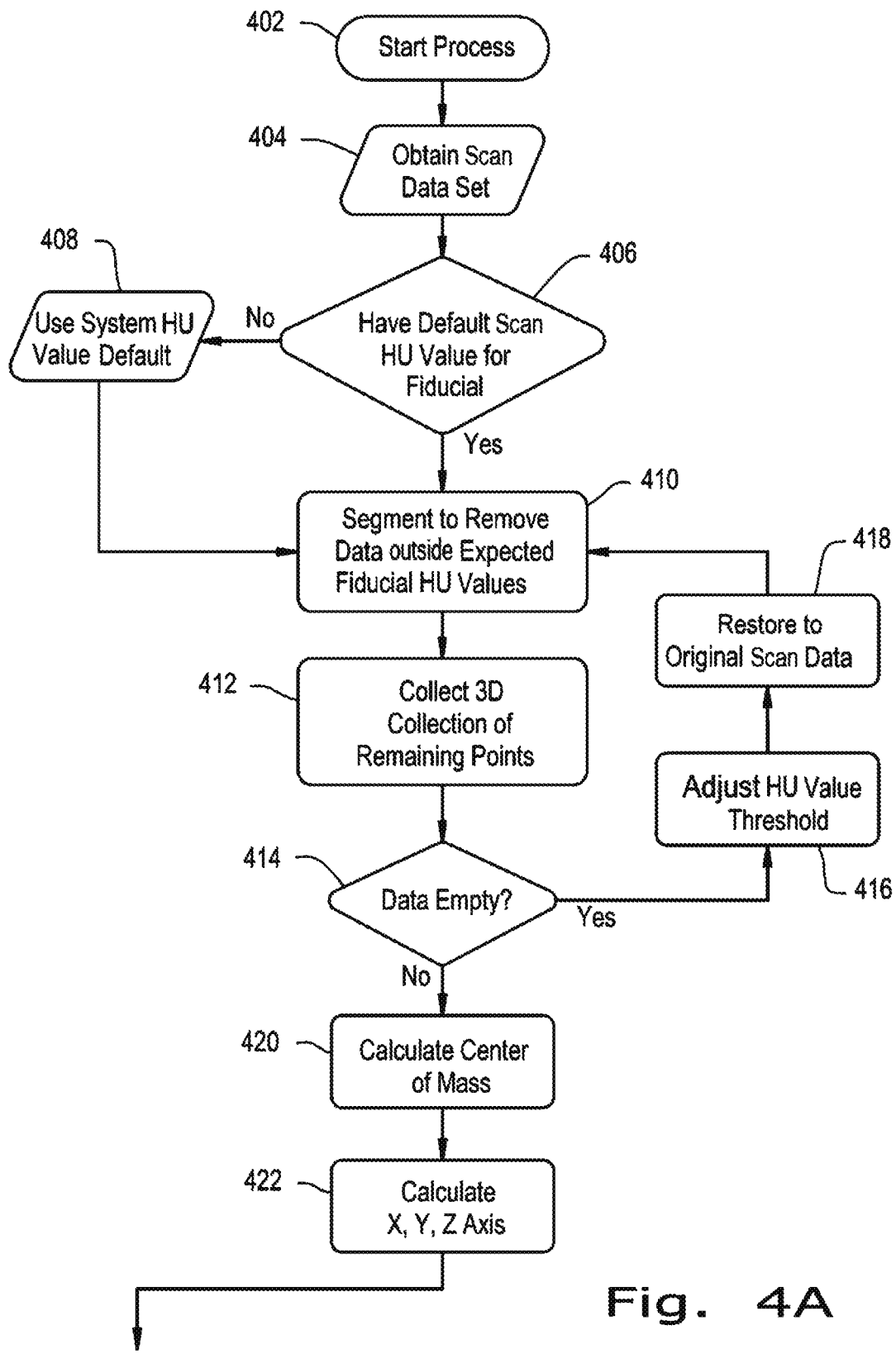
FIGS. 4A-C is a flow chart diagram illustrating one embodiment of the registering method of the present invention.
Figure 4B:
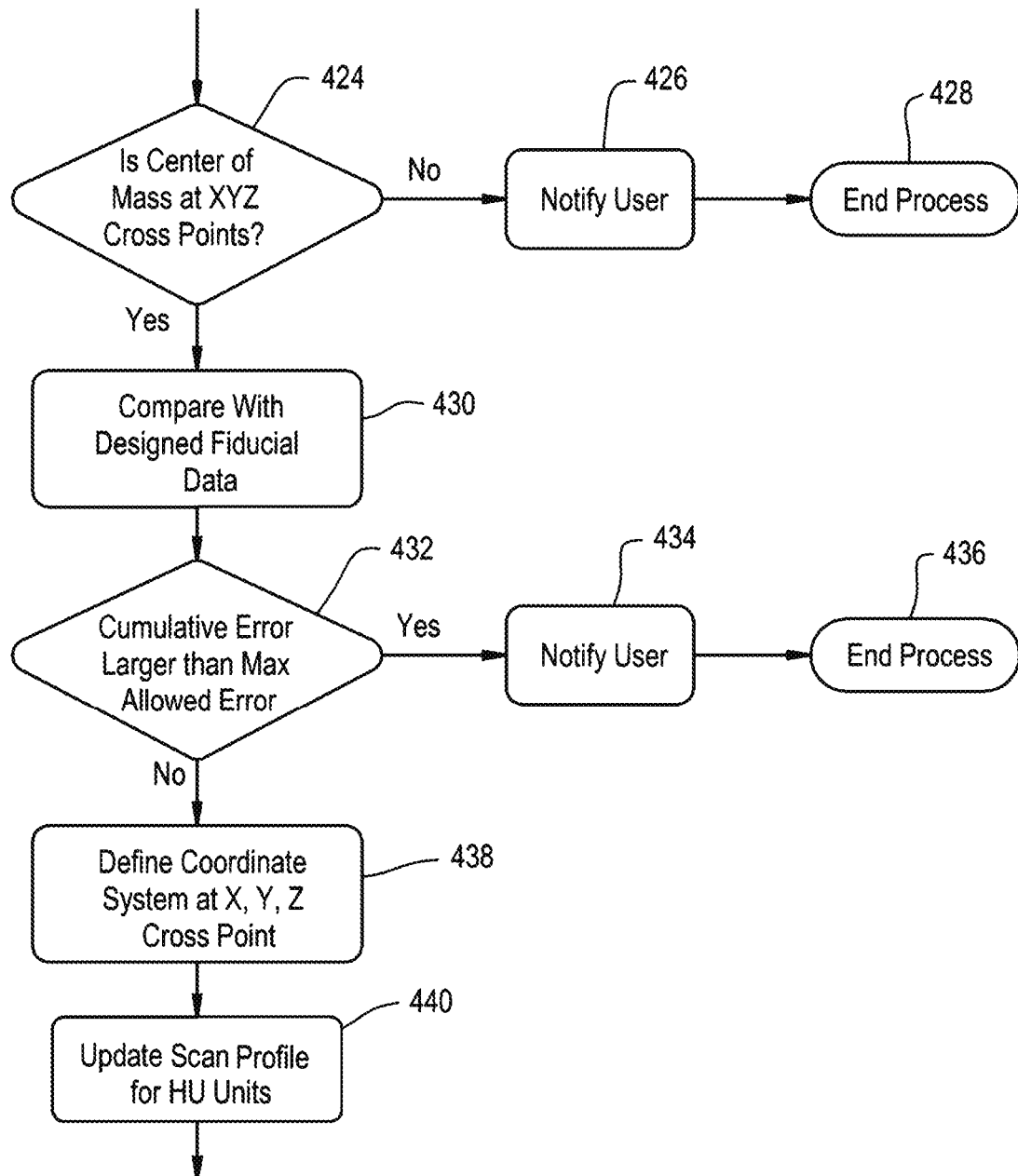
Figure 4C:
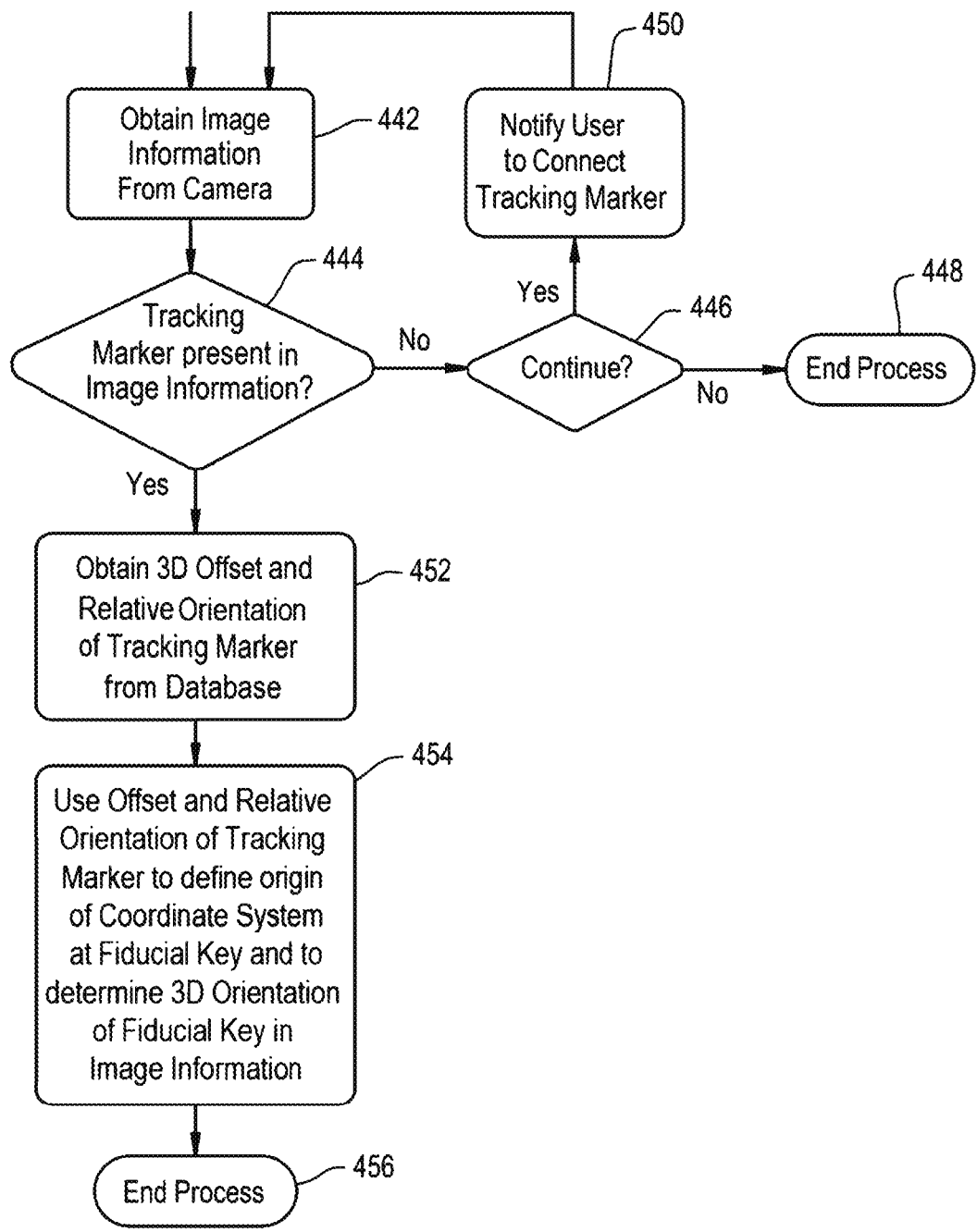

In another aspect there is presented an automatic registration method for tracking surgical activity, as illustrated in FIGS. 4A-C. FIG. 4A and FIG. 4B together present, without limitation, a flowchart of one method for determining the three-dimensional location and orientation of the fiducial reference from scan data. FIG. 4C presents a flow chart of a method for confirming the presence of a suitable tracking marker in image information obtained by the tracker and determining the three-dimensional location and orientation of the fiducial reference based on the image information.

Once the process starts [402], as described in FIGS. 4A and 4B, the system obtains [404] a scan data set from, for example, a CT scanner and checks [at 406] for a default CT scan Hounsfield unit (HU) value for the vectorized fiducial which may or may not have been provided with the scan based on a knowledge of the fiducial and the particular scanner model, and if such a threshold value is not present, then a generalized predetermined default value is employed [408]. Next the data is processed by removing [at 410] scan segments with Hounsfield data values outside expected values associated with the fiducial key values, following the collection [at 412] of the remaining points. If the data is empty [at 414], the CT value threshold is adjusted [at 416], the original value restored [at 418], and the segmenting processing scan segments continues [at 410]. Otherwise, with the existing data a center of mass is calculated [at 420], along with calculating [at 422] the X, Y, and Z axes. If the center of mass is not at the cross point of the XYZ axes [at 424], then the user is notified [at 426] and the process stopped [at 428]. If the center of mass is at the XYZ cross point then the data points are compared [430] with the designed fiducial data. If the cumulative error is larger than the maximum allowed error [at 432] then the user is notified [at 434] and the process ends [at 436]. If not, then the coordinate system is defined [at 438] at the XYZ cross point, and the scan profile is updated for the HU units [at 440].

Turning now to FIG. 4C, image information is obtained [442] from the tracker, being a suitable camera or other sensor. The image information is two-dimensional and is not required to be a stereo image pair. The image information may be sourced from a single imaging device in the tracker, or may be sourced from multiple imaging devices in the tracker. It bears pointing out that the presence of multiple imaging devices in a tracker does not automatically imply stereo imaging. The image information is analyzed [444] to determine whether a vectorized tracking marker is present in the image information. If not, then the user is queried [446] as to whether the process should continue or not. If not, then the process is ended [448]. If the process is to continue, then the user may be notified [450] that no tracking marker has been found in the image information, and the process returns to obtaining image information [442]. If a tracking marker has been found based on the image information, or one has been attached by the user upon the above notification [at 450], the offset and relative orientation of the tracking marker to the fiducial reference is obtained [452] from a suitable database. The term "database" is used in this specification to describe any source, amount or arrangement of such information, whether organized into a formal multi-element or multi-dimensional database or not. Such a database may be stored, for example, in system memory 217, fixed disk 244, or in external memory through network interface 248. A single data set comprising offset value and relative orientation may suffice in a simple implementation of this embodiment of the invention and may be provided, for example, by the user or may be within a memory unit of the controller or in a separate database or memory.

The offset and relative orientation of the tracking marker is used to define the origin of a coordinate system at the fiducial reference and to determine [454] the three-dimensional orientation of the fiducial reference based on the image information and the registration process ends [456]. In order to monitor the location and orientation of the fiducial reference in real time, the process may be looped back from step [454] to obtain new image information from the camera [at step 442]. A suitable query point may be included to allow the user to terminate the process. Detailed methods for determining orientations and locations of pre-determined shapes or marked tracking markers from image data are known to practitioners of the art and will not be dwelt upon here. The coordinate system so derived is then used for tracking the motion of any items bearing vectorized tracking markers in the proximity of the surgical site. Other registration systems are also contemplated, for example using current other sensory data rather than the predetermined offset, or having a fiducial with a transmission capacity.

Figure 4D:
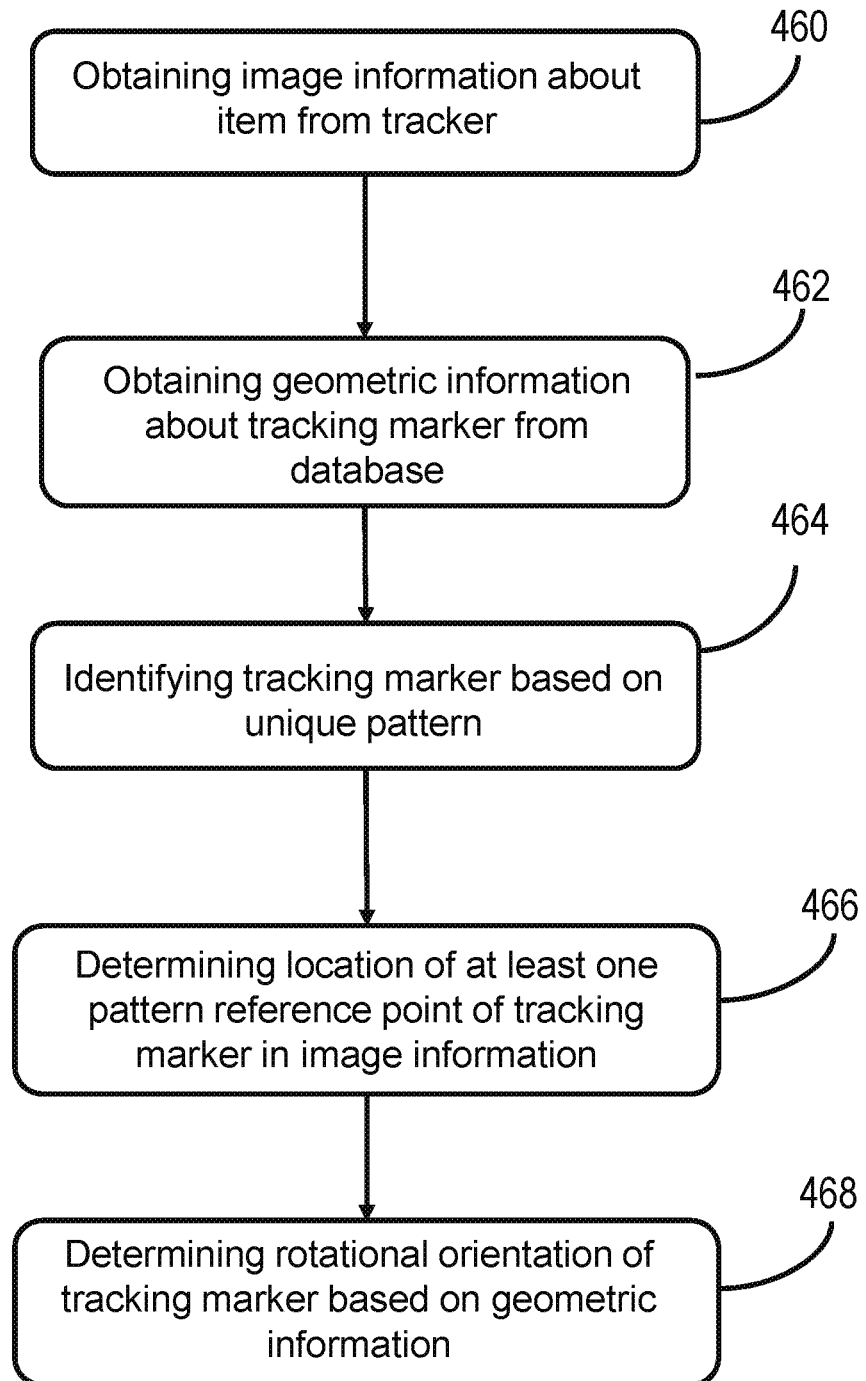
FIG. 4D is a flow chart diagram illustrating one embodiment of a method for tracking an item bearing at least one passive vectorized tracking marker.

In a further aspect, described at the hand of FIG. 4D, a method is provided for tracking an item bearing at least one vectorized tracking marker having an identifiably unique rotationally asymmetric pattern of contrasting elements disposed on a close-packed tiled background, the method comprising: providing the handheld implement bearing a passive vectorized tracking marker permanently integrated with the implement; obtaining [460] image information about the item from a non-stereo optical tracker; obtaining [462] from a database geometric information about the at least one tracking marker; identifying [464] the at least one vectorized tracking marker on the basis of the unique pattern; determining [466] within the image information the location of at least one pattern reference point of the at least one tracking marker based on the geometric information, and determining [468] within the image information the rotational orientation of the at least one vectorized tracking marker based on the geometric information. The close-packed tiled background may comprise tiles of at least two mutually contrasting colors; the tiles may have known shapes with borders, the shapes having been previously stored in the database; tiles sharing a border may have contrasting colors; and the geometric information may comprise information about the locations of contrasting pattern elements on the close-packed tiled background relative to the borders. The shapes may all be, without limitation, one of triangles, squares, rectangles, parallelograms, hexagons, and slanted hexagons. In other embodiments the tiles of the close-packed background may have differing shapes.

In some embodiments, the at least one vectorized tracking marker may be permanently integrated with the item, which may be an implement such as, for example without limitation, a dental drill or biopsy needle. In further embodiments the tracking marker may in particular be monolithically integrated with the item or implement.

The determining the location of the at least one pattern reference point of the at least one vectorized tracking marker may comprise identifying the borders in the image information and confirming one of the absence and the presence of contrasting pattern elements at expected positions relative to the borders. The contrasting pattern elements may be round dots having color contrast with respect to tiles on which they are disposed. The confirming may comprise calculating the expected positions relative to the borders based on the geometric information from the database.

Figure 4E:
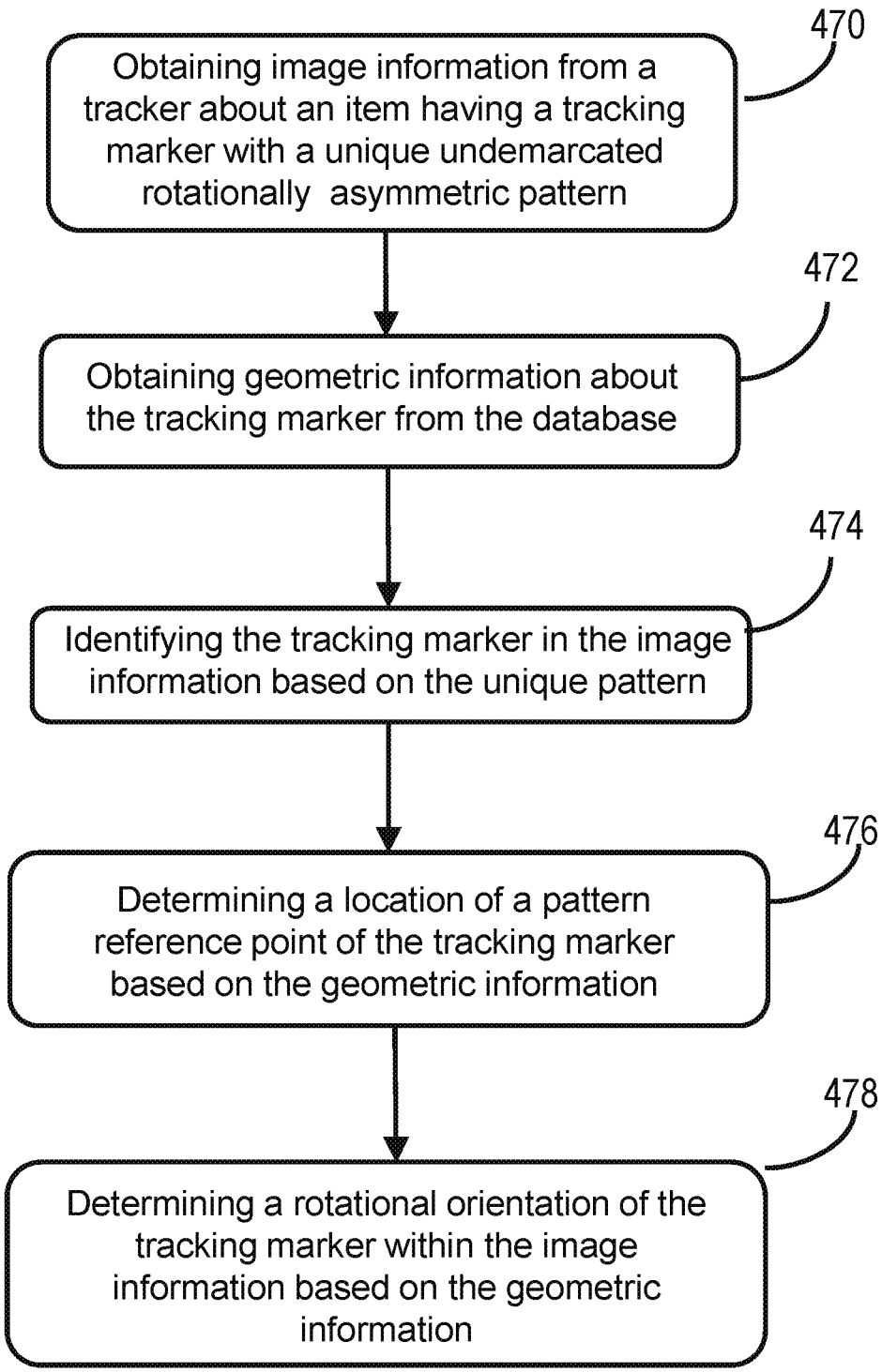
FIG. 4E is a flow chart diagram illustrating another embodiment of a method for tracking an item bearing at least one passive vectorized tracking marker with an undemarcated pattern.

In a further aspect, described at the hand of FIG. 4E and corresponding to the tracking marker of FIG. 3P, a method is provided for tracking an item bearing at least one vectorized tracking marker, for example, marker 322 of FIG. 3L, having an identifiably unique undemarcated rotationally asymmetric pattern disposed on a the tracking marker, the method comprising: (a) obtaining [470] image information about the item from a non-stereo optical tracker; (b) obtaining [472] from a database geometric information about the at least one tracking marker; (c) identifying [474] the at least one tracking marker on the basis of the unique pattern; (d) determining [476] within the image information the location of at least one pattern reference point of the at least one tracking marker based on the geometric information, and (e) determining [478] within the image information the rotational orientation of the at least one vectorized tracking marker based on the geometric information.

The determining the location of the at least one pattern reference point of the at least one vectorized tracking marker may comprise differentiating between different unit cells of undemarcated rotationally asymmetric patterns in the image information and confirming one of the absence and the presence of contrasting pattern elements at occupiable locations within the pattern. The contrasting pattern elements may be round dots having color contrast with respect to the tracking marker on which they are disposed. The confirming may comprise calculating the occupiable locations on the tracking marker based on the geometric information from the database. The confirming may further comprise detecting a color contrast between the pattern elements and the at least one tracking marker on which they are disposed. The determining the location of the at least one pattern reference point may further comprise fitting a mathematical curve to the perimeter of at least one of the contrasting pattern elements.

One example of an embodiment of the invention is shown in FIG. 5. In addition to passive vectorized fiducial key 502 mounted at a predetermined tooth and having a rigidly mounted passive vectorized tracking marker 504, an additional instrument or implement 506, for example a hand piece which may be a dental drill or scalpel, may be observed by a camera 508 serving as tracker of the monitoring system. Implement 506 may bear a vectorized tracking marker 507 allowing it to be tracked by tracker 508. Tracker 508 may in some embodiments be, in particular, a non-stereo tracker. Tracker 508 supplies image information of a field of view of tracker 508 to controller 520, which displays derived information on a display system or monitor 530. Controller 520 may be based on, for example, processor 214 and memory 217 of computer 210 of FIG. 2 and monitor 530 may have with controller 520 the structural relation that display screen 224 has with central processor 214 in FIG. 2.

Another example of an embodiment of the invention is shown in FIG. 6. Surgery site 600, for example a human stomach or chest, may have fiducial key 602 fixed to a predetermined position to support tracking marker 604. Other apparatus with suitable tracking markers may be in use in the process of the surgery at surgery site 600. By way of non-limiting example, endoscope 606 may have a further passive vectorized tracking marker 607, and biopsy needle 608 may also be present at surgery site 600 bearing passive vectorized tracking marker 609. Sensor 610, serving as tracker for the system, may be for example a camera, infrared sensing device, or RADAR. In particular, the tracker may be a two-dimensional imaging tracker that produces a two-dimensional image of surgery site 600 for use as image information for the purposes of embodiments of the invention, including two-dimensional image information of any vectorized tracking markers in the field of view of the tracker. Sensor 610 may be, for example, a non-stereo optical camera. In other embodiments, sensor 610 may be a stereo camera. Surgery site 600, endoscope 606, biopsy needle 608, fiducial key 602 and vectorized tracking markers 604, 607 and 609 may all be in the field of view of tracker 610. Sensor 610 supplies image information of a field of view of sensor 610 to controller 520 which displays derived information on a display system or monitor 530.

Figure 7:
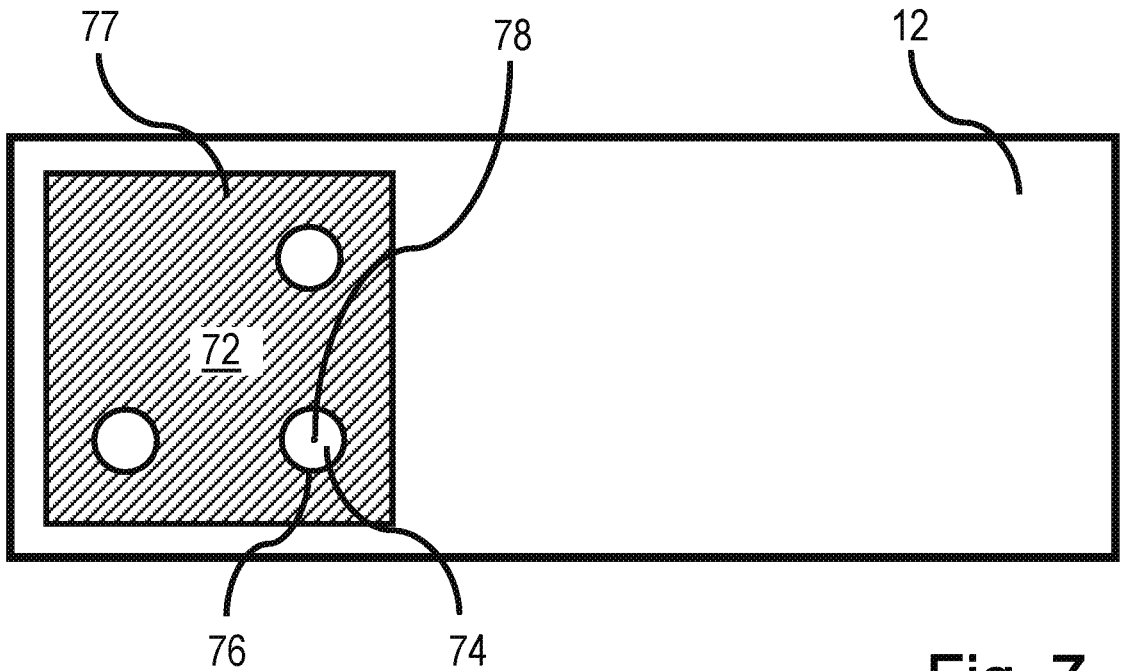
FIG. 7 is a drawing of a passive vectorized tracking marker bearing a pattern tag according to an embodiment of the present invention.

A further aspect of the invention is described at the hand of FIG. 7, which shows in more detail passive vectorized tracking marker 12 of FIGS. 3A and 3B. As stated heretofore, tracking marker 12 may have a particular identifying pattern. In this further aspect of the invention the matter of the particular pattern, shown generally at 72, on tracking marker 12 is addressed in more detail. In a first embodiment shown in FIG. 7, pattern 72 comprises a plurality of contrasting portions 74. Pattern 72 is further characterized by being rotationally asymmetrical. As a result, an image of pattern 72 inherently identifies the rotational orientation about an axis perpendicular to the plane of pattern 72 of vectorized tracking marker 12. Pattern 72 is further characterized by having at least one contrasting portion 74 that has a perimeter comprising a mathematically describable curved section. In FIG. 7 the simplest case of circular perimeter 76 is shown, which comprises the entire perimeter. In other embodiments the curved section may constitute less than the entire perimeter and the curve may be, for example, without limitation, a conic section. In yet further embodiments the curve may be a mathematically describable curve other than a conic section.

The basis or grounds of the contrast is limited only in that the contrast has to be discernible by the tracker employed in the surgical site monitoring system of the present invention.

For example without limitation, the contrast with surrounding areas on vectorized tracking marker 12 may be by virtue of contrasting portion 74 being a cutout, by virtue of the contrasting portion 74 being a darker or lighter greytone, by virtue of the contrasting portion 74 being a different hue or saturation, by virtue of contrasting portion 74 being a different color in any color space, by virtue of contrasting portion 74 being a different brightness in an infrared image, or any other basis of image contrast.

Pattern 72 may be implemented on separate pattern tag 77 that is attached or pasted, temporarily or permanently, to tracking marker 12. Conversely, pattern tag 77 may be in itself a tracking marker, such as, for example tracking marker 12, so that the tracking marker itself bears pattern 72. Pattern tag 77 may be planar. Pattern tag 77 may be flexible to allow it to return to planarity (a planar situation) after being flexibly deformed. The materials of pattern tag 77 may be, for example without limitation, a polymer or a paper or a mix of both paper and polymer. In other embodiments tag 77 may be non-flexibly deformable while remaining dimensionally stable. An individual tracking marker may comprise a plurality of pattern tags, each with a pattern of its own, as will be described below.

The presence of the mathematically describable curved section provides three distinct benefits. Firstly, it overcomes the inherent problem of straight-edged shapes such as squares, rectangles, and parallelograms which exacerbate problems stemming from the finite number and size of pixels available in typical trackers, such as the tracker used in the several embodiments of the present invention. Due to the fact that the pixels have a finite size, the determination of the exact location of a straight line in an image is difficult to do to an accuracy of less than one pixel. A contrasting portion with a straight-line section to its perimeter would inherently suffer from this limitation. By employing a mathematically describable curved section as perimeter 76 of contrasting portion 74 the location of perimeter 76 may inherently be determined more accurately. We do not dwell here upon the methods of determining contrast boundaries in digital images, as the concepts and methods are well described in the art and well known to practitioners of the art.

Secondly, in addition to the aforementioned more accurate determination of the location of the perimeter, the mathematically describable nature of the curve of perimeter 76 allows a single very accurate contrasting portion reference point 78 to be determined once an image of pattern 72 is available, showing its contrasting portion 74 and perimeter 76. By way of the circular example of FIG. 7, a useful choice for a contrasting portion reference point 78 may be the center of the circle described by perimeter 76, which in this case is the center of contrasting portion 74. However, in a more general case, a point other than the center of the circle may be employed as reference to suit the application.

Thirdly, with the mathematical description of a section of perimeter 76 of contrasting portion 74 known, the rotation of pattern 72 about further axes may be determined. To this end, the appearance of pattern 72 may be expressed in mathematical terms and stored in a database of any kind, including without limitation a digital database. The tracker of the monitoring system may obtain image information about pattern 72 on a vectorized tracking marker 12. By analyzing the image information mathematically using a suitable controller, for example processor 214 and memory 217 of computer 210 of FIG. 2, and comparing with the stored information about the mathematical description of the pattern, the three-dimensional orientation of vectorized tracking marker 12 may be determined. If tracking marker 12 has a large enough three-dimensional extent, then suitable patterns of contrasting portions may also be applied to further surfaces of tracking marker 12 to assist in determining the three-dimensional orientation of tracking marker 12.

Pattern 72 may be selected to be a unique pattern. This allows pattern tag 77 or tracking marker 12 to be uniquely identified within the field of view of the tracker. Thus a variety of items, objects, instruments or implements may be tagged with tracking markers bearing pattern tags, or with just pattern tags, thereby to uniquely identify and track such items, objects, instruments or implements and determine their orientations.

Having described this general aspect of the invention at the hand of contrasting portions with simple circular shapes, we turn to other embodiments employing contrasting portions employing other shapes. In other embodiments the curve may be, for example any other form of conic section, such as an ellipse or a parabola and may extend all the way around the contrasting portion. In the case of an ellipse, the contrasting portion reference point may be chosen, for example, to lie along the major semi-axis or minor semi-axis of the ellipse. In particular, a useful choice for contrasting portion reference point may be one of the foci of the ellipse. Another useful choice for contrasting portion reference point may be one of the vertices of the ellipse. In this respect it is to be noted that all that is required is a section of an ellipse, long enough for accurate mathematic description, thereby to allow the determination of the various axes and the foci. The contrasting portion therefore does not have to be a complete ellipse. Herein lies the benefit of the curve being mathematically describable. If a parabola is chosen, a useful choice for contrasting portion reference point may be the focus of the parabola, the vertex of the parabola or the point where the axis of symmetry of the parabola crosses the directrix of that parabola.

In yet further embodiments of the invention a mathematically describable curve other than a conic section may be used to describe at least a section of the perimeter of the contrasting portion. Such curves may well be more complex than conic sections and may require careful consideration as regards a suitable contrasting portion reference point. In yet further embodiments of the invention, the contrasting portion may be a mix of the aforementioned conic sections and other shapes. One example is a semicircle, which, despite having only part of its perimeter described by a circle, nevertheless allows all of the benefits of the mathematically described circle.

In yet further embodiments of the invention the pattern may comprise a plurality of contrasting portions of which more than one contrasting portion has a perimeter having a mathematically describable curved section. A pattern reference point may in such a case be a point expressed relative to the resulting plurality of contrasting portion reference points derived from the more than one contrasting portion. For example without limitation, each of the three contrasting portions of pattern tag 77 in FIG. 7 is a circle and each has its center as contrasting portion reference point. In such a case, the pattern reference point may be, for example, given by a point exactly at the middle of the line joining the centers of the two unnumbered contrasting portions. Any other useful point may be selected for this purpose, including the contrasting portion reference point 78 or any of the corners of pattern tag 77.

Figure 8:
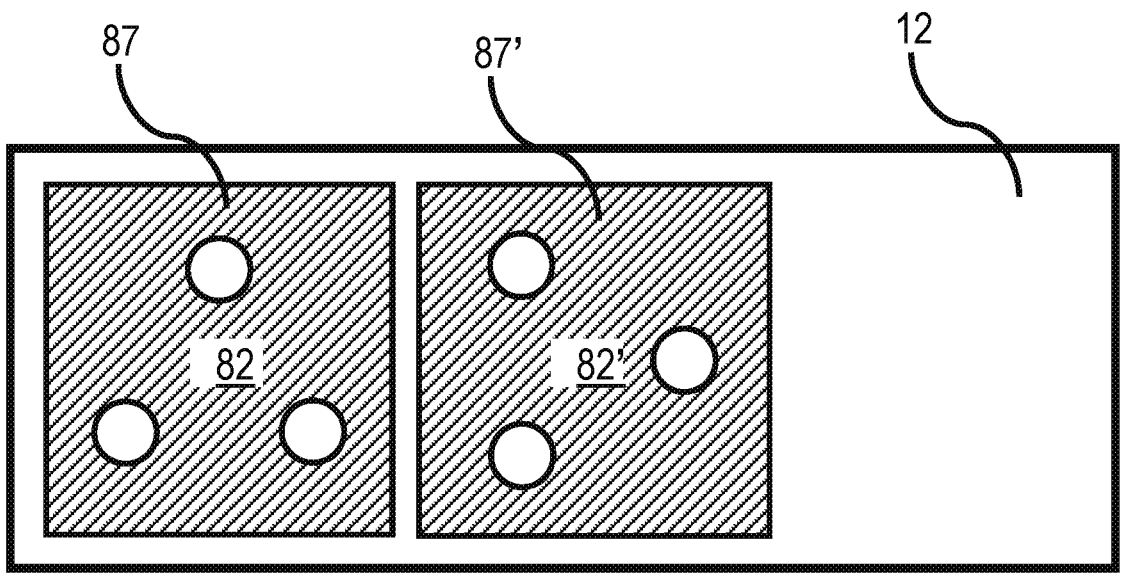
FIG. 8 is a drawing of a passive vectorized tracking marker bearing two pattern tags according to another embodiment of the present invention.

In a further implementation shown in FIG. 8, passive vectorized tracking marker 12 may comprise more than one pattern tag, for example pattern tag 87 and pattern tag 87', with each pattern tag 87 and 87' individually having a pattern shown generally at 82 and 82' respectively and each having rotational symmetry, while the combination of patterns 82 and 82' is rotationally asymmetrical. In this particular implementation the two tags are identical, but, in a general case, are located on tracking marker rotated with respect to each other. This has the benefit of requiring only one kind of patterned tag. It reduces costs and also lowers the management burden during practical use, as only one kind of tag needs to be kept at hand for in, for example, surgery. In another embodiment, two pattern tags 87 and 87' may be arranged next to each other on tracking marker 12 in identical orientations. This still provides a resulting pattern that is rotationally asymmetric. In FIG. 8 two pattern tags 87 and 87' are shown as being attached in coplanar fashion. In other embodiments they are not limited to being coplanar.

Figure 9:
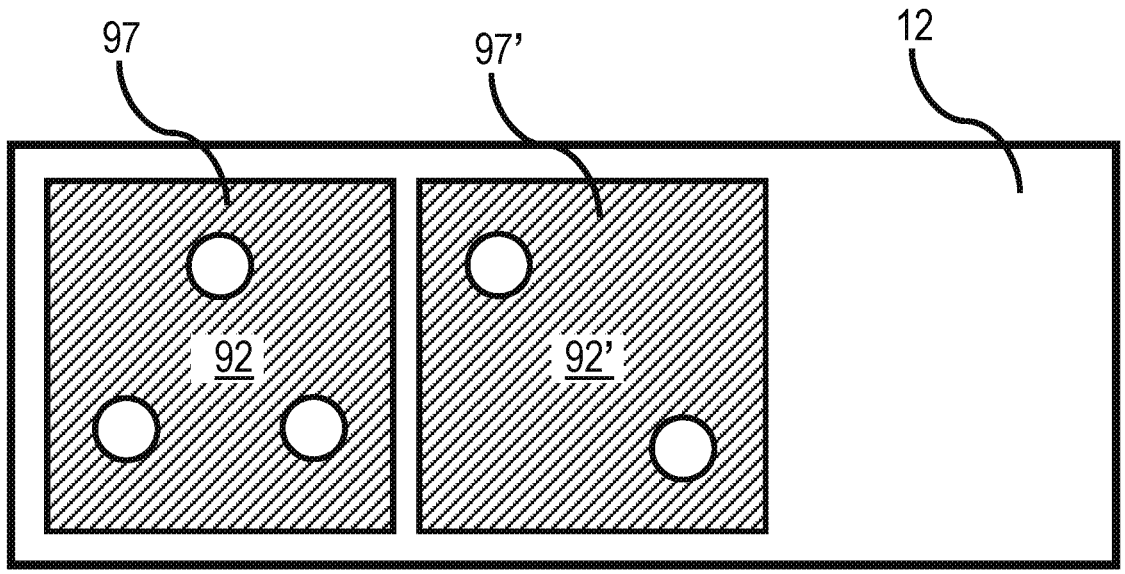
FIG. 9 is a drawing of a passive vectorized tracking marker bearing two pattern tags according to a further embodiment of the present invention.

In a further implementation shown in FIG. 9 two pattern tags 97 and 97' are employed and both have some form of rotational symmetry. Pattern tag 97 has pattern 92 with rotational symmetry of 120 degrees while pattern tag 97' has pattern 92' that differs from pattern 92 and has a rotational symmetry of 180 degrees. Two pattern tags 97 and 97' together, however, provide rotational asymmetry.

Figure 10:
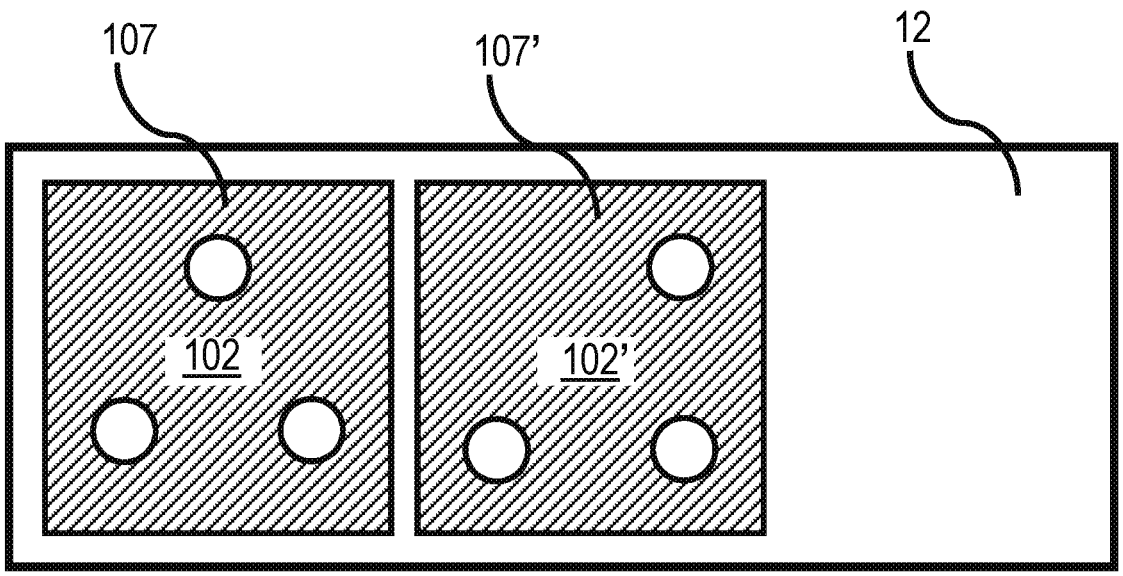
FIG. 10 is a drawing of a passive vectorized tracking marker bearing two pattern tags according to yet a further embodiment of the present invention.
Figure 11:
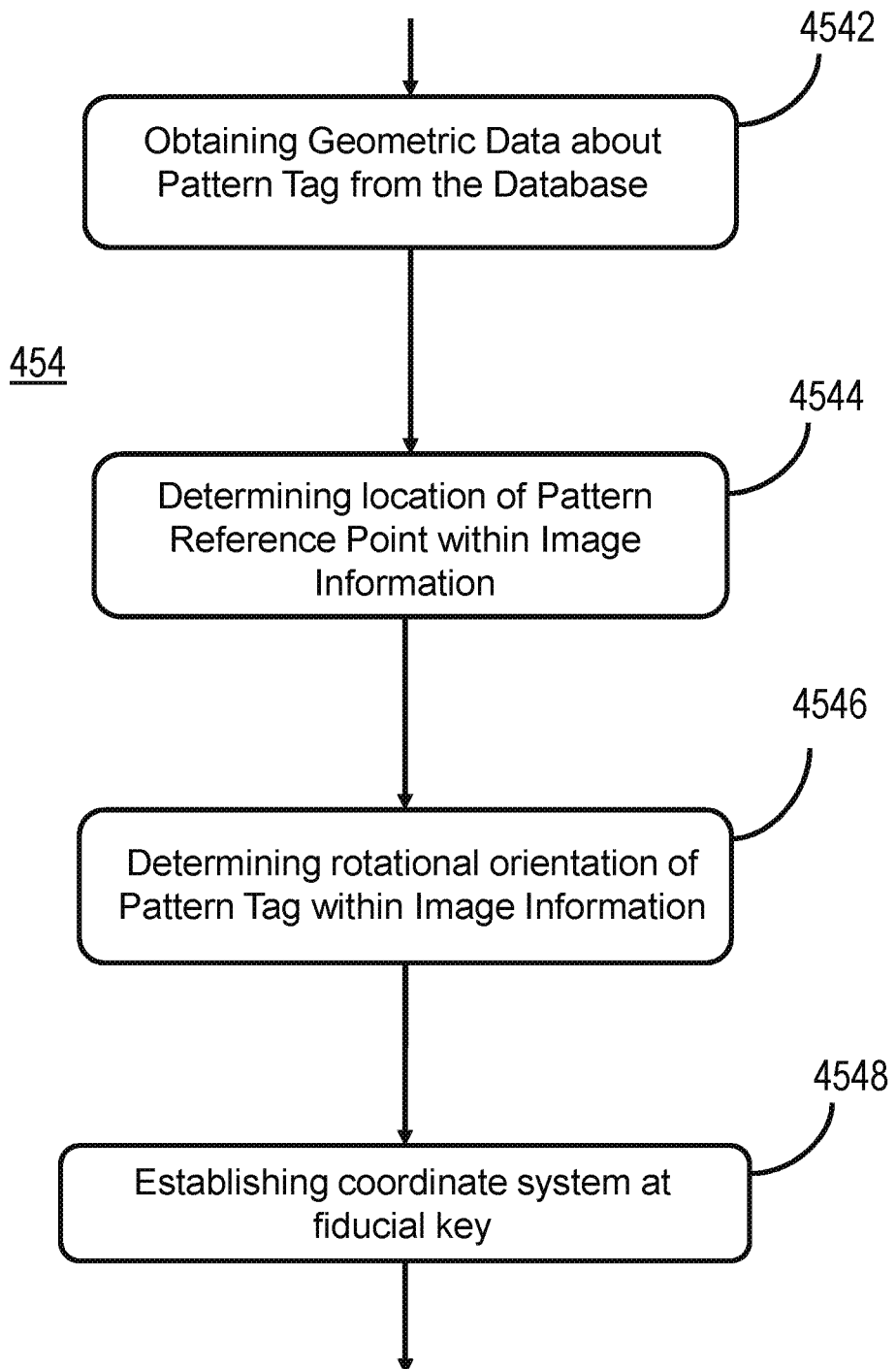
FIG. 11 is a drawing of a flow chart for a method of establishing a coordinate system at a passive vectorized fiducial key according to an embodiment of the present invention.

In FIG. 10 is presented yet a further implementation based on pattern 102 of pattern tag 107 having rotational symmetry and pattern 102' of pattern tag 107' being rotationally asymmetrical. Joint patterns 102 and 102' constitute a rotationally asymmetrical pattern.

In FIGS. 7-10 very simple patterns have been used as examples. The patterns may be chosen to be more complex and thereby more unique. This allows the pattern tags to be uniquely identified within the field of view of the tracker. Thus a variety of items, objects, instruments or implements may be tagged pattern tags, thereby to uniquely identify and track such items, objects, instruments or implements and determine their orientations. The sets of two pattern tags of FIGS. 8-10 may in each embodiment of the invention constitute a single tracking marker.

Patterns 82, 82', 92, 92', 102, 102' of FIGS. 8-10 may be implemented on a separate pattern tags that are attached or pasted, temporarily or permanently, to passive tracking marker 12. Conversely, pairs of pattern tags (87, 87'), (97, 97'), and (107, 107'), may be in themselves be tracking markers, such as, for example tracking marker 12, so that the tracking markers themselves bear patterns (82, 82'), (92, 92'), and (102, 102') respectively. Pattern tags may be planar. Pattern tags may be flexible to allow them to return to planarity after being flexibly deformed. The materials of pattern tags may be, for example without limitation, a polymer or a paper or a mix of both paper and polymer. In other embodiments tags may be non-flexibly deformable while remaining dimensionally stable.

The automatic registration method for tracking surgical activity already described at the hand of FIGS. 4A-C may employ the passive vectorized tracking marker of FIGS. 7-10 bearing the pattern tags and or patterns described at the hand of FIGS. 7-10. In the method of FIG. 4A the offset and relative orientation of the tracking marker to the fiducial reference is obtained from a suitable database in method step [452]. If the tracking marker, pattern tags and patterns of FIGS. 7-10 are employed, then the database in question is pre-supplied with information concerning tracking marker 12, pattern tags 77, 87, 87', 97, 97', 107, 107', patterns 72, 82, 82', 92, 92', 102, 102' and the contrasting portions, for example contrasting portion 74, of the pattern tags. The information comprises, in particular, the mathematical descriptions of curved sections of the perimeters of the contrasting portions of the pattern tags, for example perimeter 76. It may also comprise the locations of contrasting portion reference points, for example contrasting portion reference point 78, and pattern reference points for pattern tags that are be employed. The term "geometric information" is employed in the present specification to describe this collection of information regarding the shapes, sizes, perimeters, curved perimeter sections and the like of the contrasting portions of the pattern tags, along with the information on the patterns on the various pattern tags attached to the tracking markers and the associated locations of contrasting portion reference points and pattern reference points. The geometric information specifically comprises a mathematical description of at least a section of the perimeter of at least one contrasting portion on any given pattern tag. The geometric information may also include the known spatial and orientation relationship between the pattern tags and the tracking markers.

The automatic registration method for tracking surgical activity as per the present embodiment employing the pattern tags (for example pattern tag 77) as described herein comprises the steps [402] to [456] of FIGS. 4A-C. In step [444] of FIG. 4C, tracking marker 12 has already been identified on the basis of its unique pattern as per FIGS. 7-10. Step [454] of FIG. 4C will now be described in more detail at the hand of FIG. 11. The using [454] the offset and relative orientation of passive vectorized tracking marker 12 to define an origin of a coordinate system at fiducial key 10 and to determine the three-dimensional orientation of fiducial key 10 in image information, as shown in FIG. 4C, comprises the following steps in FIG. 11. The process starts with the controller, for example processor 214 and memory 217 of computer 210 of FIG. 2, obtaining [at 4542] from the database geometric information about at least one pattern tag (for example pattern tag 77) associated with the tracking marker 12, the controller determining [at 4544] within the image information the location of at least one of the pattern reference points of the at least one pattern tag 77 based on the geometric information, and the controller determining [at 4546] within the image information the rotational orientation of the at least one pattern tag (for example pattern tag 77) based on the geometric information. With the relationship of the pattern reference point to tracking marker pre-established within the geometrical information, and the offset and relative orientation of vectorized tracking marker 12 with respect to fiducial key 10 known (see step [452] in FIG. 4C), a coordinate system is established [at 4548] at fiducial key 10.

The rotationally asymmetrical tracking marker arrangements described here may be applied to other fields of general machine vision and product tracking beyond the field of surgery. More specifically, while vectorized tracking marker 12 has been described in terms of being attached to fiducial key 10 by tracking pole 11 (see for example FIG. 3B), the patterned tracking markers of the present invention may be applied in other fields without the use of fiducials and tracking poles, in which case they are useful in determining the physical spatial orientation of items bearing the patterned tracking markers. By way of example, a flexible pattern tag may be applied to a cylindrical surface of an object, such as a can in the food industry. With the pattern reference point known and with the mathematical description of the pattern known, the position of the can and the curvature of the pattern tag may respectively be determined from image information obtained using a suitable tracker.

Figure 12:
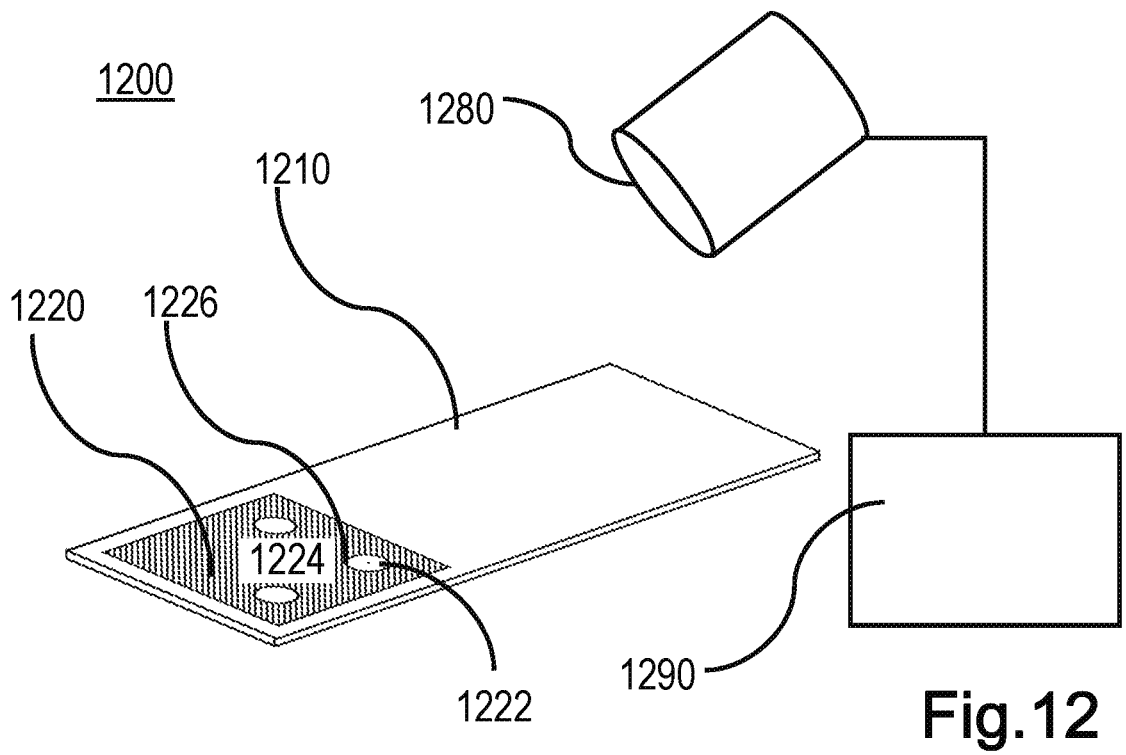
FIG. 12 is a drawing of a three-dimensional position and orientation tracking system according to an embodiment of the present invention.

In a further embodiment of the present invention, shown schematically in FIG. 12, a three-dimensional position and orientation tracking system, shown generally at 1200, comprises at least one passive vectorized pattern tag 1220 attached to item 1210, pattern tag 1220 comprising a plurality of contrasting portions 1222. System 1200 further comprises tracker 1280 configured for obtaining image information about the at least one pattern tag 1220; a database comprising geometric information describing pattern 1224 on the at least one pattern tag 1220; and controller 1290, for example processor 214 and memory 217 of computer 210 of FIG. 2. Controller 1290 is configured for receiving and processing the image information from tracker 1280; accessing the database to retrieve geometric information about the at least one pattern tag 1220; and comparing the image information with the geometric information. The plurality of contrasting portions 1222 are arranged in rotationally asymmetric pattern 1224 and at least one of the plurality of contrasting portions 1222 has perimeter 1226 comprising a mathematically describable curved section. Perimeter 1226 of the at least one contrasting portion 1222 may comprise a conic section including, for example without limitation, an ellipse or a circle. The at least one pattern tag 1220 may be flexible. The at least one passive vectorized pattern tag 1220 may be substantially planar.

Figure 13:
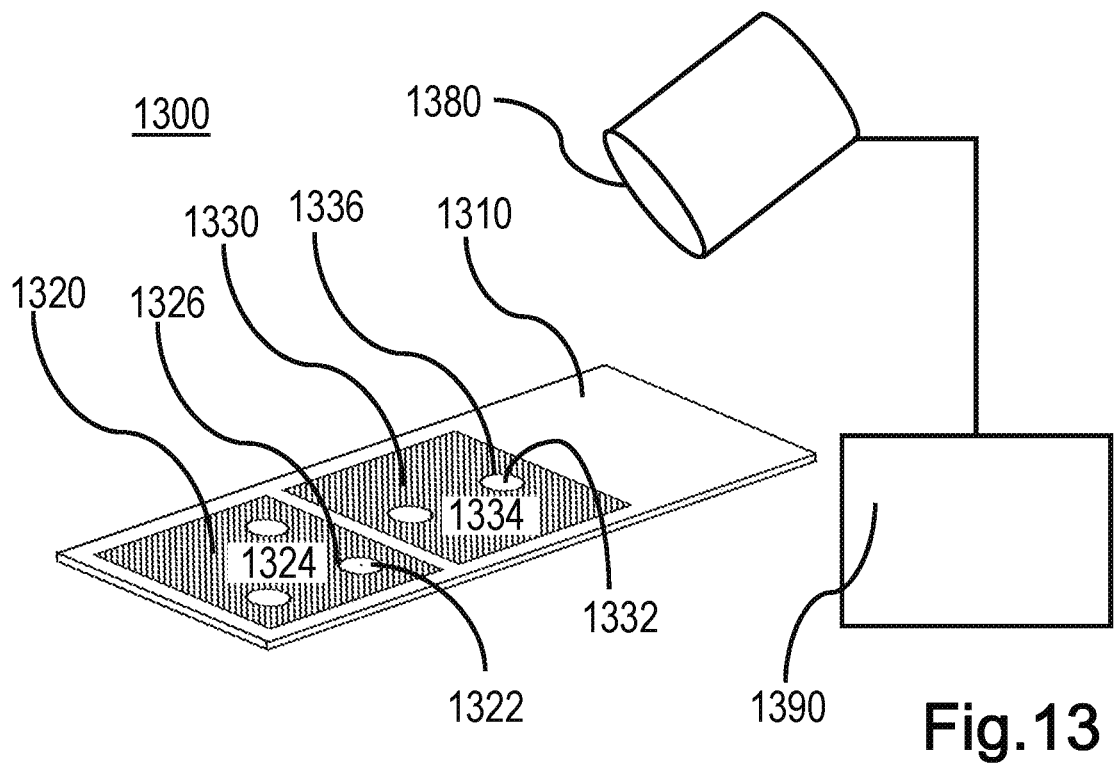
FIG. 13 is a drawing of a three-dimensional position and orientation tracking system according to another embodiment of the present invention.

In another embodiment of the present invention, shown schematically in FIG. 13, the three-dimensional position and orientation tracking system, shown generally at 1300, may comprise at least two pattern tags attached to item 1310, a first of the at least two pattern tags, shown in FIG. 13 as pattern tag 1320, comprising a first plurality of contrasting portions 1322 and a second of the at least two pattern tags, shown in FIG. 13 as pattern tag 1330, comprising at least one contrasting portion 1332; tracker 1380 configured for obtaining image information about the at least two pattern tags 1320 and 1330, a database comprising pattern tag information describing the appearance of the at least two pattern tags; and controller 1390, for example processor 214 and memory 217 of computer 210 of FIG. 2. Controller 1390 is configured for receiving and processing the image information from tracker 1380; accessing the database to retrieve geometric information about at least two pattern tags 1320 and 1330; and comparing the image information with the geometric information. At least one of the first and second pattern tags, taken to be 1330 in FIG. 13, has one or more contrasting portions 1332 arranged in rotationally symmetric pattern 1334; contrasting portions 1322 and 1332 of respectively first and second pattern tags 1320 and 1330 together constitute a rotationally asymmetric pattern; and at least one contrasting portion 1322, 1332 respectively of each of the at least two pattern tags 1320, 1330 has perimeter 1326, 1336, comprising a mathematically describable curved section.

In respect of the two embodiments exemplified in FIGS. 12 and 13 simple patterns have been used as examples. The patterns may be chosen to be more complex and thereby more unique. This allows the pattern tags to be uniquely identified within the field of view of the tracker. Thus a variety of items, objects, instruments or implements may be tagged with pattern tags, thereby to uniquely identify and track such items, objects, instruments or implements and determine their orientations.

Figure 14:
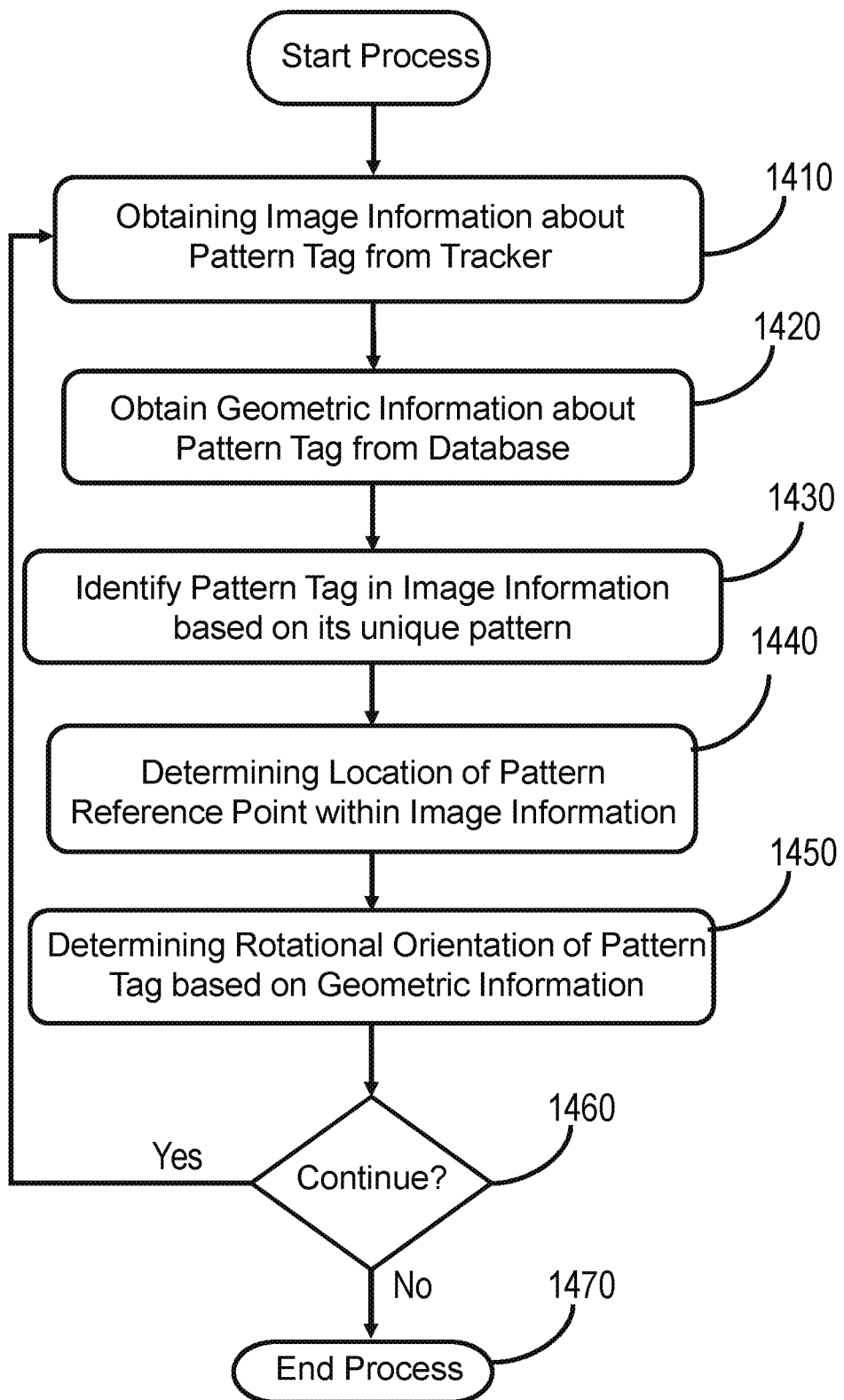
FIG. 14 is a drawing of a flow chart describing a further method for tracking an item bearing a passive vectorized pattern tag.

In a further aspect of the invention, described at the hand of the flow chart in FIG. 14, a method is provided for tracking an item bearing at least one passive vectorized pattern tag, for example pattern tag 1220, 1320, or 1330 of FIGS. 12 and 13. The method comprises suitable controller 1290, 1390 (comprising for example processor 214 and memory 217 of computer 210 of FIG. 2) obtaining [at 1410] from a suitable tracker, for example tracker 1280 of FIG. 12 or tracker 1380 of FIG. 13, image information about the at least one passive vectorized pattern tag. The method further comprises controller 1290 or 1390 obtaining [at 1420] from a suitable database geometric information about the at least one passive vectorized pattern tag (for example pattern tag 77), the controller identifying [at 1430] the at least one passive vectorized pattern tag on the basis of its unique pattern, and the controller determining [at 1440] within the image information the location of at least one pattern reference point of the at least one passive vectorized pattern tag based on the geometric information, the geometric information specifically comprising a mathematical description of at least a section of perimeter 1226, 1326, 1336 of at least one contrasting portion 1222, 1322, 1332 of the at least one passive vectorized pattern tag. The method further comprises the controller determining [at 1450] within the image information the rotational orientation of the at least one passive vectorized pattern tag based on the geometric information. Having located the at least one pattern reference point and having determined the rotational orientation of the at least one passive vectorized pattern tag, the user is queried [at 1460] as to whether the process should continue or not. If not, then the process is ended [at 1470]. If the process is to continue, then the process returns to obtaining refreshed image information [at 1410].

Figure 15:
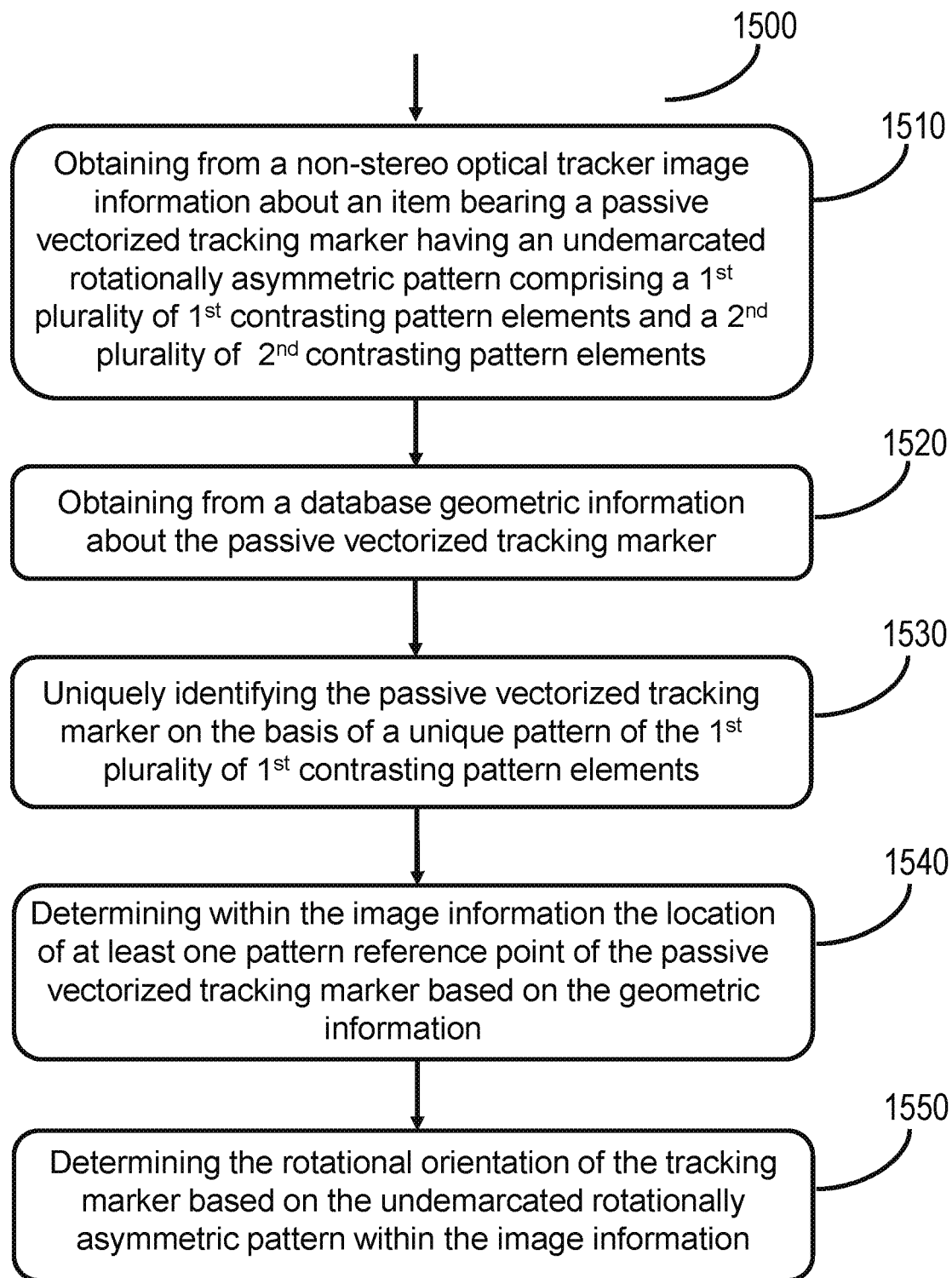
FIG. 15 is a drawing of a flow chart describing a method for tracking an item bearing a passive vectorized pattern tag having a pattern comprising two mutually discernible kinds of pattern elements.

In a further aspect of the invention, described at the hand of the flow chart of FIG. 15, method [1500] is provided for tracking in three dimensions an item bearing at least one passive vectorized tracking marker having disposed on the tracking marker an undemarcated rotationally asymmetric pattern comprising a first plurality of first contrasting pattern elements and a second plurality of second contrasting pattern elements; the method comprising: obtaining [1510] image information about the item from a non-stereo optical tracker; obtaining [1520] from a database geometric information about the at least one tracking marker; uniquely identifying [1530] the at least one passive vectorized tracking marker on the basis of a unique pattern of the first plurality of first contrasting pattern elements; determining [1540] within the image information the location of at least one pattern reference point of the at least one passive vectorized tracking marker based on the geometric information, and determining [1550] the rotational orientation of the at least one tracking marker based on the undemarcated rotationally asymmetric pattern within the image information.

The obtaining geometric information [1520] may comprise obtaining information about the first plurality of first contrasting pattern elements and the second plurality of second contrasting pattern elements within the asymmetric pattern; and obtaining information about the locations of pattern elements within the first and second pluralities of pattern elements.

The determining the location [1540] of the at least one pattern reference point of the at least one passive vectorized tracking marker may comprise differentiating between first and second pattern elements in the image information. The determining the location [1540] of the at least one pattern reference point may further comprise fitting a mathematical curve to the perimeter of at least one of the contrasting pattern elements. The uniquely identifying [1530] may comprise detecting a contrast between the pattern elements and the at least one passive vectorized tracking marker on which the pattern elements are disposed.

Figure 16:
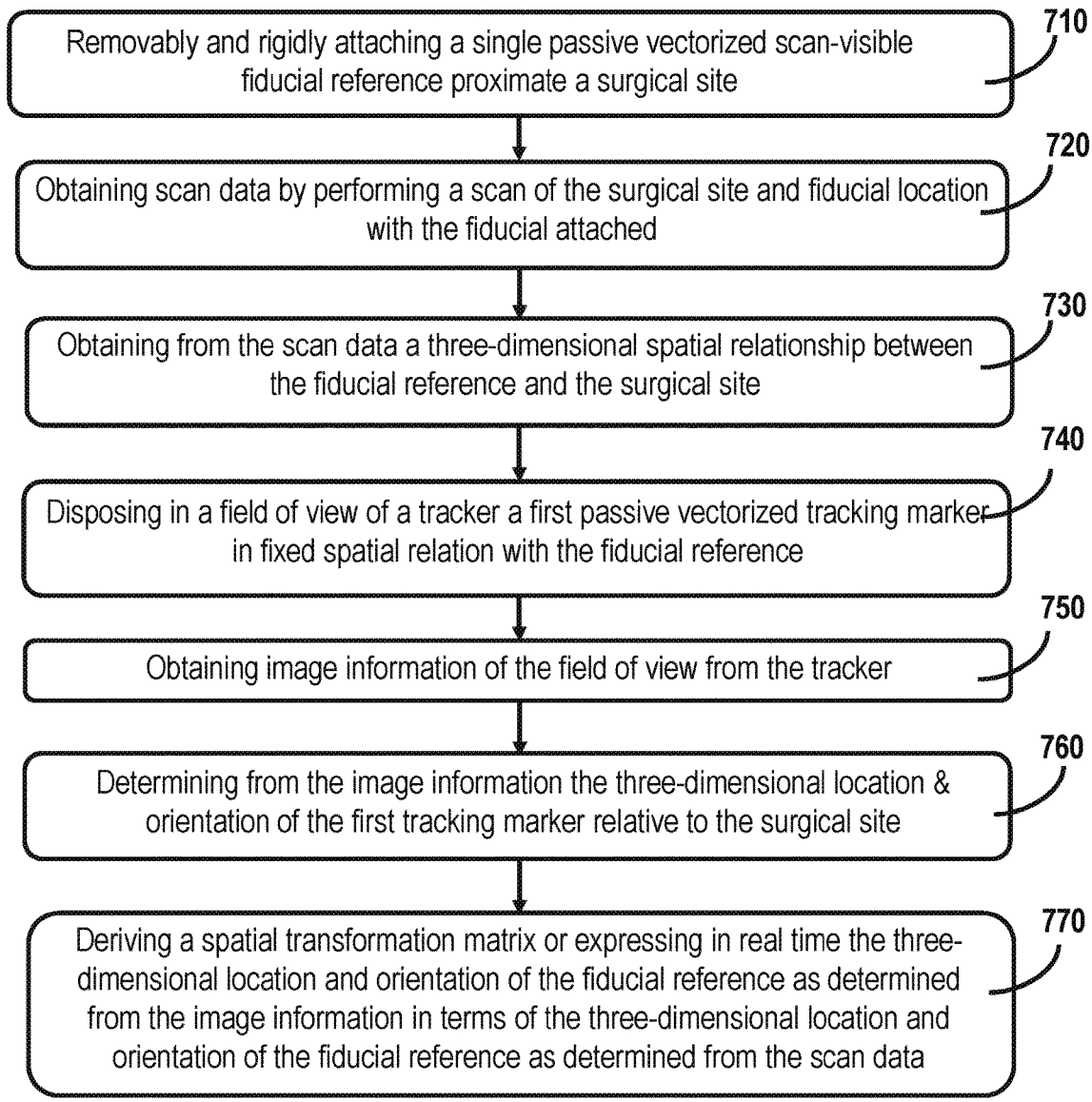
FIG. 16 shows a flow chart for a method for relating in real time a three-dimensional location and orientation of surgical site on a patient to the location and orientation of the surgical site in a scan of the surgical site.

In another aspect of the present invention there is provided a method, described with reference to FIG. 5 and the flow chart in FIG. 16, for relating in real time the three-dimensional location and orientation of surgical site 550 on a patient to the location and orientation of the surgical site in a scan of surgical site 550, the method comprising removably and rigidly attaching [710] single passive scan-visible vectorized fiducial reference 502 to a fiducial location on the patient proximate surgical site 550; performing the scan with single fiducial reference 502 attached to the fiducial location to obtain [720] scan data; obtaining [730] the three-dimensional location and orientation of fiducial reference 502 from the scan data; obtaining [750] real time image information of surgical site 550 (using tracker 508); determining [760] in real time the three-dimensional location and orientation of single fiducial reference 502 from the image information; and deriving [770] a spatial transformation matrix or expressing in real time the three-dimensional location and orientation of fiducial reference 502 as determined from the image information in terms of the three-dimensional location and orientation of single fiducial reference 502 as determined from the scan data.

Obtaining [750] of real time image information from surgical site 550 may comprise rigidly and removably attaching to fiducial reference 502 first passive vectorized tracking marker 504 in a fixed three-dimensional spatial relationship with fiducial reference 502, therewith disposing [740] tracking marker 504 in a field of view of tracker 508. First tracking marker 504 may be configured for having its location and its orientation determined based on the image information. Attaching first tracking marker 504 to single fiducial reference 502 may comprise rigidly and removably attaching first tracking marker 504 to fiducial reference 502 by means of a tracking pole. In this regard, see for example tracking pole 11 of FIG. 3B used to attach vectorized tracking marker 12 to fiducial reference 10. Attaching first tracking marker 504 to single fiducial reference 502 may comprise rigidly and removably attaching to fiducial reference 502 the tracking pole in a fixed three-dimensional spatial relationship with fiducial reference 502, and the tracking pole may have a distinctly identifiable three-dimensional shape that allows its location and orientation to be uniquely determined from the image information.

Figure 17:
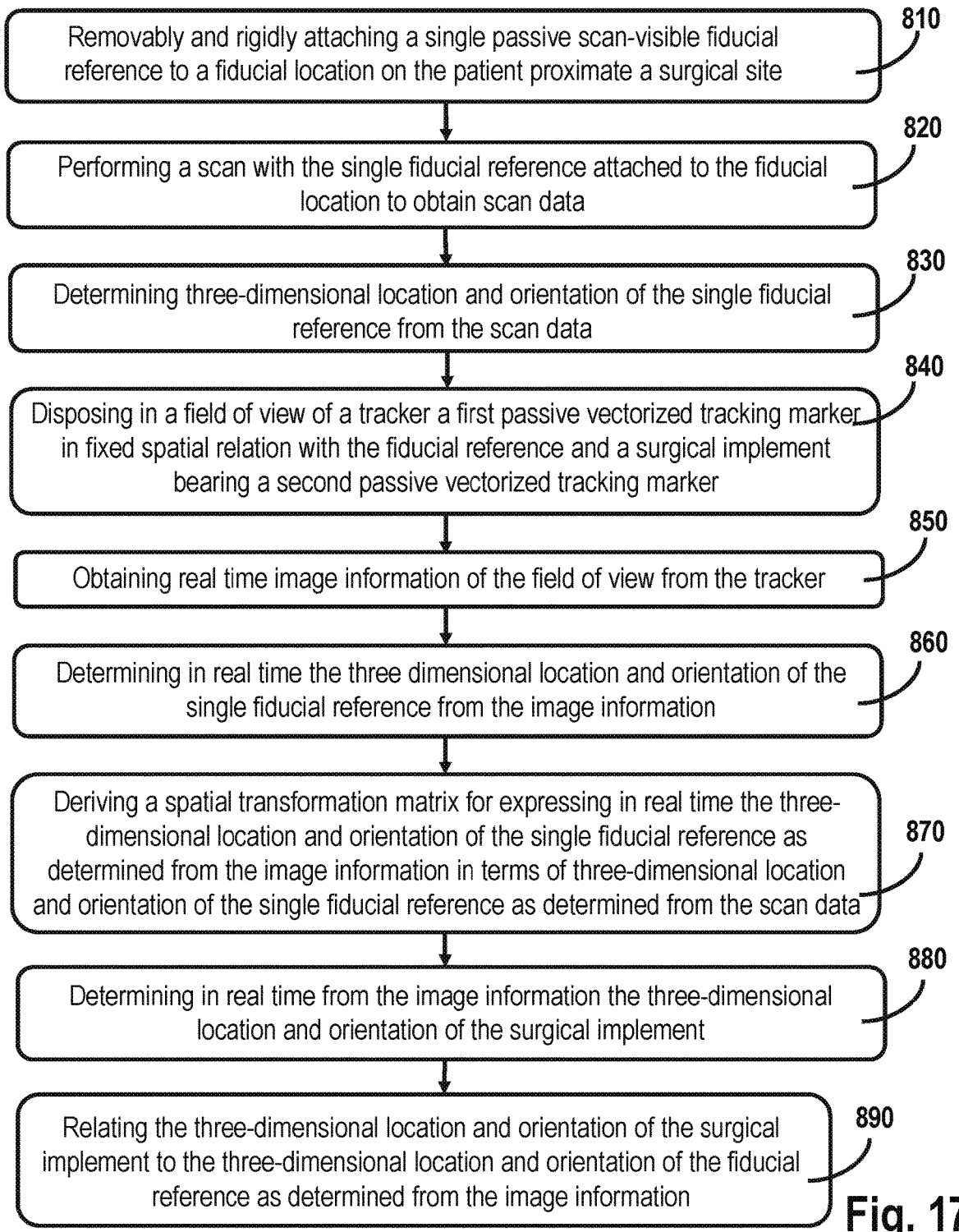
FIG. 17 is a flow chart of a method for real time monitoring of the position of a surgical implement in relation to a surgical site according to the present invention.

In yet a further aspect of the invention, explained at the hand of the flow chart of FIG. 17, there is provided a method for real time monitoring the position of an object, for example implement 506 in FIG. 5, in relation to surgical site 550 of a patient, the method comprising removably and rigidly attaching [810] single passive scan-visible fiducial reference 502 to a fiducial location on the patient proximate surgical site 550; performing [820] a scan with single fiducial reference 502 attached to the fiducial location to obtain scan data; determining [830] the three-dimensional location and orientation of single fiducial reference 502 from the scan data; obtaining [850] real time image information of surgical site 550 (using tracker 508); determining [860] in real time the three-dimensional location and orientation of single fiducial reference 502 from the image information; deriving [870] a spatial transformation matrix for expressing in real time the three-dimensional location and orientation of single fiducial reference 502 as determined from the image information in terms of the three-dimensional location and orientation of single fiducial reference 502 as determined from the scan data; determining [880] in real time the three-dimensional location and orientation of implement 506 from the image information; and relating [890] the three-dimensional location and orientation of implement 506 to the three-dimensional location and orientation of the fiducial reference 502 as determined from the image information.

Obtaining [850] of real time image information from surgical site 550 may comprise rigidly and removably attaching to fiducial reference 502 a first passive vectorized tracking marker 504 in a fixed three-dimensional spatial relationship with fiducial reference 502, therewith disposing [840] tracking marker 504 in a field of view of tracker 508. First tracking marker 504 may be configured for having its location and its orientation determined based on the image information. Attaching first tracking marker 504 to single fiducial reference 502 may comprise rigidly and removably attaching first tracking marker 504 to the fiducial reference 502 by means of a tracking pole. In this regard, see for example tracking pole 11 of FIG. 3B used to attach vectorized tracking marker 12 to fiducial reference 10. Attaching first tracking marker 504 to single fiducial reference 502 may comprise rigidly and removably attaching to fiducial reference 502 the tracking pole in a fixed three-dimensional spatial relationship with fiducial reference 502, and the tracking pole may have a distinctly identifiable three-dimensional shape that allows its location and orientation to be uniquely determined from the image information.

In some circumstances during surgery, surgical implements are changed or modified. An example is when one drill bit is exchanged for another. It would be advantageous if the surgical navigation system could determine the characteristics of a drill bit inserted in the handpiece during the surgery. Specifying this manually to a software interface is inconvenient, interrupts workflow, and is error prone, while mechanically measuring the drill bit interrupts workflow and risks compromising the sterile part. Prior art optical methods require placing the surgical tool into a measuring device or in a known position against a target or reference.

Figure 18A:
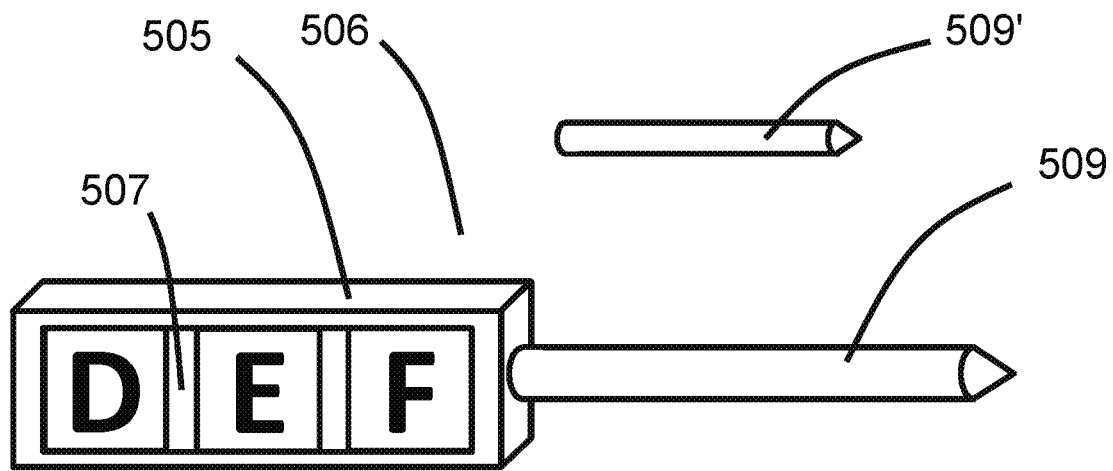
FIGS. 18A and 18B are more detailed drawings of an element of FIG. 5.
Figure 18B:
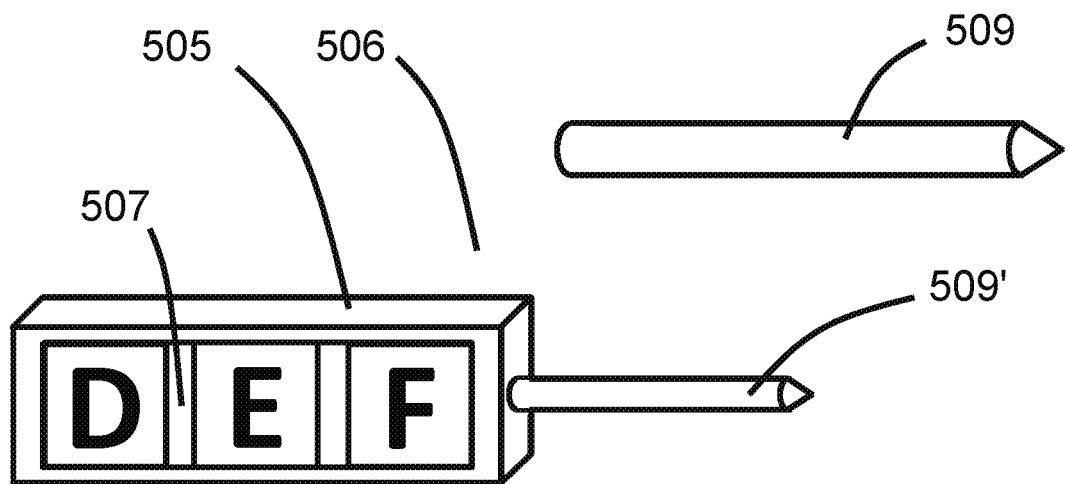

In a further aspect of the invention addressing this issue, surgical implement 506 of FIG. 5, shown in more detail in FIGS. 18A and 18B, may comprise invariant portion 505 and interchangeable portion 509. For example, without limitation, implement 506 may be dental drill 506 comprising drill body 505 as invariant portion and interchangeable drill bit 509 as interchangeable portion. In alternative embodiments, implement 506 may be a scalpel and interchangeable portion 509 may be a scalpel blade. Drill bit 509 may, for example, be interchanged with drill bit 509', which may, for example, have a different length and/or diameter. In other embodiments, interchangeable portions 509 and 509' may be portions with different functions. The collective characteristic of all the interchangeable portions is that they are at least one of shapewise and dimensionally uniquely identifiable from the image information supplied by tracker 508 of FIG. 5. FIG. 18A schematically shows interchangeable portion 509 mounted in invariant portion 505, and FIG. 18B schematically shows interchangeable portion 509' mounted in invariant portion 505. Invariant portion 505 is configured to allow interchangeable portions, for example interchangeable portions 509 and 509', to be seated spatially consistently in invariant portion 505.

Tracker 508 of FIG. 5 has sufficiently high imaging resolution to resolve in the imaging information the dimensions and shapes of interchangeable portions 509 and 509' in order for controller 520 to uniquely identify interchangeable portions 509 and 509'. To this end, the database of the monitoring system further comprises a data set or database describing at least one of the dimensions, the shapes, and the configurations of all interchangeable portions of implement 506 available for use with the system. The database may be stored, for example, in system memory 217, fixed disk 244, or in external memory through network interface 248. The dimensions and shape of invariant portions, for example invariant portion 505 of FIGS. 18A and 18B, may also be stored in the database, so that the interchangeable portions, for example interchangeable portions 509, 509' of FIGS. 18A and 18B, may be uniquely identifiable from the image information.

In other embodiments, tracker 508 of FIG. 5 may have two imagers obtaining two separate perspectives of the field of view of tracker 508 and interchangeable portions 509, 509' in that field of view. This allows the working tip of interchangeable portions 509, 509' to be determined in three dimensions. From this may then be derived the length of interchangeable portion 509, 509' so that the particular portion may then be identified from the database based on a unique length. In yet a further embodiment, the tip of interchangeable portion 509, 509' located and oriented in this way may be related to the known and tracked three-dimensional location and orientation of tracking marker 507 on invariant portion 505 of implement 506. This relationship having been established, the three-dimensional location and orientation of the working tip of interchangeable portion 509, 509' may then be calculated in real time based on the tracked three-dimensional location and orientation of tracking marker 507.

Figure 19:
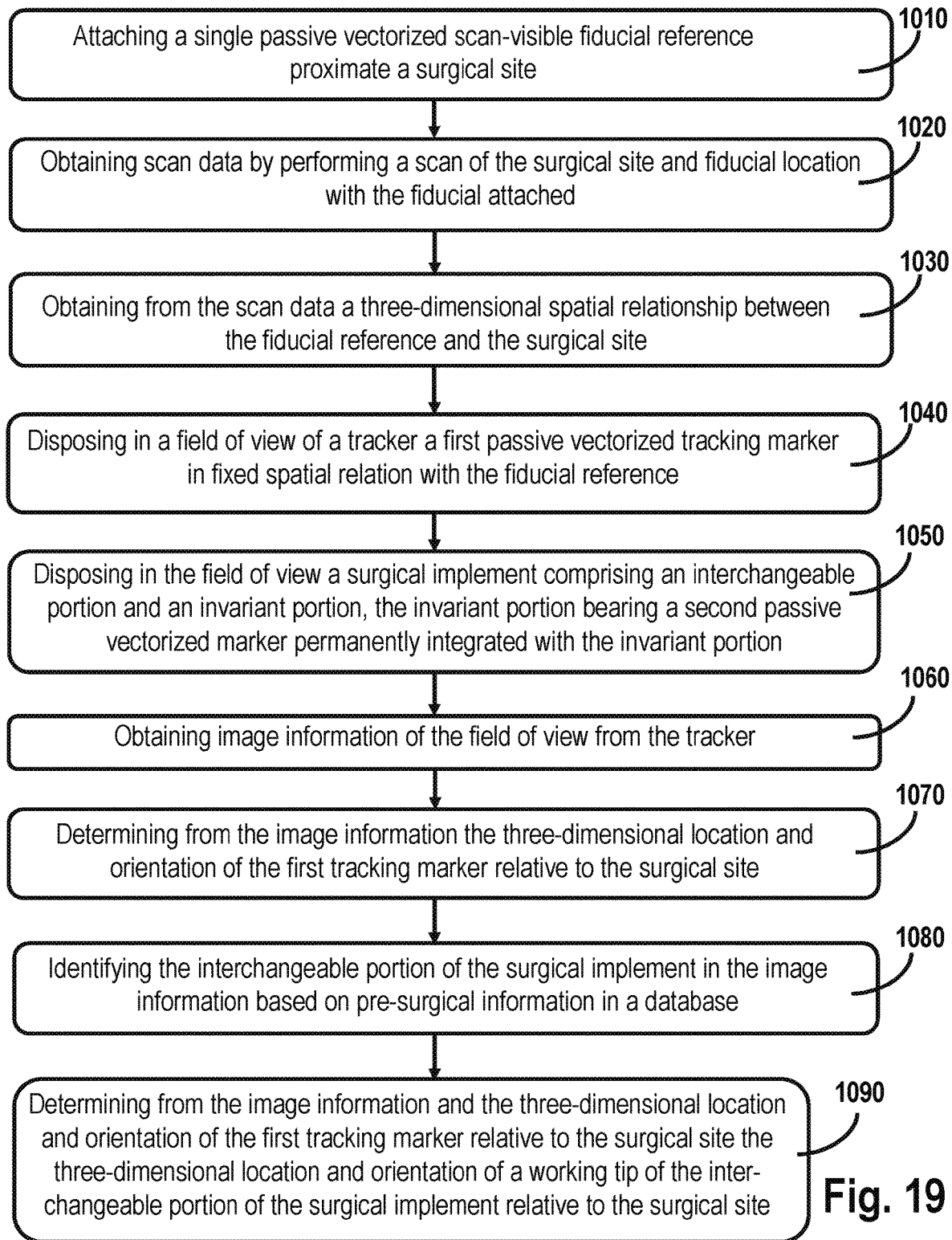
FIG. 19 is a flow chart of a method for monitoring changes in a surgical implement according to the present invention.

In a further aspect of the invention, described at the hand of FIG. 5 and FIG. 19, a method is provided for monitoring changes in a surgical implement 506 in three dimensions relative to surgical site 550, the method comprising, attaching [1010] single passive vectorized scan-visible fiducial reference 502 at a fiducial location proximate surgical site 550; obtaining [1020] scan data by performing a scan of surgical site 550 and fiducial location with fiducial 502 attached; obtaining [1030] from the scan data a 3D spatial relationship between fiducial reference 502 and surgical site 550; disposing [1040] in a field of view of optical tracker 508 first passive vectorized tracking marker 504 in fixed spatial relation with fiducial reference 502; disposing [1050] in the field of view surgical implement 506 comprising interchangeable portion 509, 509' and invariant portion 505, invariant portion 505 bearing second passive vectorized marker 507 permanently integrated with invariant portion 505; obtaining [1060] image information of the field of view from tracker 508; determining [1070] from the image information the 3D location & orientation of first tracking marker 504 relative to surgical site 550; identifying [1080] interchangeable portion 509, 509' of surgical implement 506 in the image information; determining [1090] from the image information and from the 3D location and orientation of first tracking marker 504 relative to surgical site 550 the 3D location and orientation of a working tip of interchangeable portion 509, 509' of surgical implement 506 relative to surgical site 550. Determining [1090] of the location and orientation of a working tip of interchangeable portion 509, 509' relative to the surgical site 550 may further comprise identifying the second tracking marker 507 in the image information and determining the three-dimensional location and orientation of second tracking marker 507 to which invariant portion 505 is attached.

In one embodiment of the method, identifying [1080] interchangeable portion 509, 509' of surgical implement 506 in image information is based on pre-surgical information in a database. In other embodiments of the method, identifying [1080] interchangeable portion 509, 509' of surgical implement 506 in image information comprises determining the three-dimensional location of the working tip of interchangeable portion 509, 509' and determining the length of interchangeable portion 509, 509' from the three-dimensional location of the working tip and the three-dimensional location and orientation of second tracking marker 507 and invariant portion 505 attached to second tracking marker 507. Determining the three-dimensional location of a working tip of interchangeable portion 509, 509' comprises triangulating the three-dimensional location of the working tip based on two separate perspectives of interchangeable portions 509, 509' in the field of view of tracker 508.

Figure 20:
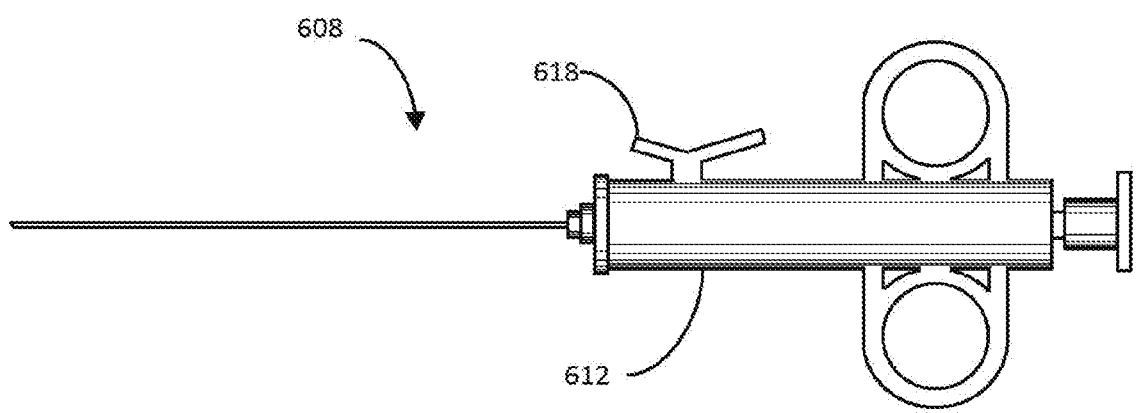
FIG. 20 is a drawing of a biopsy needle showing an embodiment of a monolithically integrated vectorized passive tracking marker.

In FIG. 6, we have seen one embodiment of a tracking marker used to track biopsy needle 608. FIG. 20 shows another embodiment of a vectorized tracking marker of, for example, biopsy needle 608. In this embodiment, vectorized tracking marker 618 is monolithically integrated with a rigid positioning and orienting portion of biopsy needle 608. In the present specification the phrase "monolithically integrated" is used to describe items that are fashioned together from one piece of material; this to be contrasted with a situation where the items are joined together after manufacture, either detachably or through a non-integral coupling. In this particular example, a suitable rigid positioning and orienting portion of biopsy needle 608 is handle 612. Handle 612 may, for example be molded, cast, machined or otherwise fashioned from one monolithic piece of material and vectorized tracking marker 618 is fashioned, formed or made from the same monolithic piece of material. Vectorized tracking marker 618 may be formed during the same process as that within which rigid handle portion 612 of biopsy needle 608 is made.

In other embodiments, the three-dimensional passive tracking marker may be integrated with the rigid positioning and orienting portion of biopsy needle 608 such that it is permanently integrated, but not specifically monolithically integrated. By way of non-limiting example, the marker may be attached using epoxy cement, thereby permanently fixing its position and orientation on the rigid portion positioning and orienting portion of biopsy needle 608.

Handle 612 itself may in some embodiments comprise two or more sections, but, when assembled, the two or more sections create a rigid whole that dictates where and how the working end of the apparatus, in this case the point of biopsy needle 608, is positioned and oriented in three dimensions relative to handle 612. To the extent that vectorized tracking marker 618 is monolithically integrated with a rigid part of handle 612 of biopsy needle 608, and the position and orientation of monolithically integrated tracking marker 618 relative to the point of biopsy needle 608 is fixed and known, knowledge of the three-dimensional position and orientation of tracking marker 618 within the field of view of tracker 610 provides the user with the location and orientation of the point of biopsy needle 608. In such an embodiment, based on for example two halves of handle 612 of biopsy needle 608, the relevant rigid positioning and orienting portion of biopsy needle 608 is the half of handle 612 with which vectorized tracking marker 618 is monolithically integrated.

The monolithic integration of three-dimensional vectorized tracking markers with a rigid positioning and orienting portion of an instrument is not limited to surgical devices. It may be applied to any medical instrument having a suitable rigid positioning and orienting portion and, indeed, to any apparatus having a suitable rigid positioning and orienting portion. In this respect, dental drill 506, shown in FIG. 5 and in FIGS. 18A and 18B, may similarly be manufactured with a vectorized tracking marker, for example tracking marker 507, permanently affixed to a rigid positioning and orienting portion of dental drill 506. A suitable rigid positioning and orienting portion of dental drill 506 may be, for example, invariant portion 505 of FIGS. 18A and 18B.

As with tracking markers described elsewhere in this disclosure, vectorized tracking marker 618 may be shaped in three dimensions so as to allow its orientation to be determined from a two-dimensional image of biopsy needle 608 within the field of view of tracker 610. In further embodiments, monolithically integrated tracking marker 618 may have a monolithically integrated marking so as to allow its orientation to be determined from a two-dimensional image of biopsy needle 608 within the field of view of tracker 610. In further embodiments, the vectorized tracking marker may be both shaped and marked to allow its orientation, its location, or both to be determined.

In yet further embodiments, positioning and orienting markings may be scribed, engraved, stamped, embossed or otherwise formed on tracking marker 618. Useful markings for determining the location and orientation of vectorized tracking marker 618 may comprise a plurality of contrasting portions arranged in a rotationally asymmetric pattern. At least one of the contrasting portions may have a perimeter that has a mathematically describable curved section. The perimeter of the contrasting portion may comprise a conic section, including for example an ellipse or a circle. The markings may be monolithically integrated with the tracking marker. In other embodiments the markings may be scribed, engraved, stamped, embossed or otherwise formed on tracking marker 618. Geometric information about the asymmetric pattern may be stored in a database. A suitable controller, for example processor 214 and memory 217 of computer 210 of FIG. 2, may be used to compare the image information obtained from tracker 610 with the geometric information about vectorized tracking marker 618 in order to determine the three-dimensional location and orientation of vectorized tracking marker 618 and its associated biopsy needle 608.

The markings may be borne on tracking markers that have a three-dimensional shaped surface. The tracking system may be implemented in a surgical monitoring system in which the markings are on pattern tags attached to tracking markers, or the pattern tags may themselves tracking markers. In other embodiments, the contrasting portions may be implemented as contrasting pattern elements on a close-packed tiled background of tiles of at least two mutually contrasting colors.

In a further aspect of the invention a method for making a three dimensionally trackable rigid positioning and orienting portion of a handheld apparatus comprises monolithically forming a three-dimensional passive tracking marker integral with the rigid positioning and orienting portion of the apparatus. The method may further comprise monolithically forming positioning and orienting markings integral with the tracking marker to render it vectorized. The method may further comprise scribing, engraving, stamping, embossing or otherwise forming positioning and orienting markings on the three-dimensional tracking marker.

Figure 21:
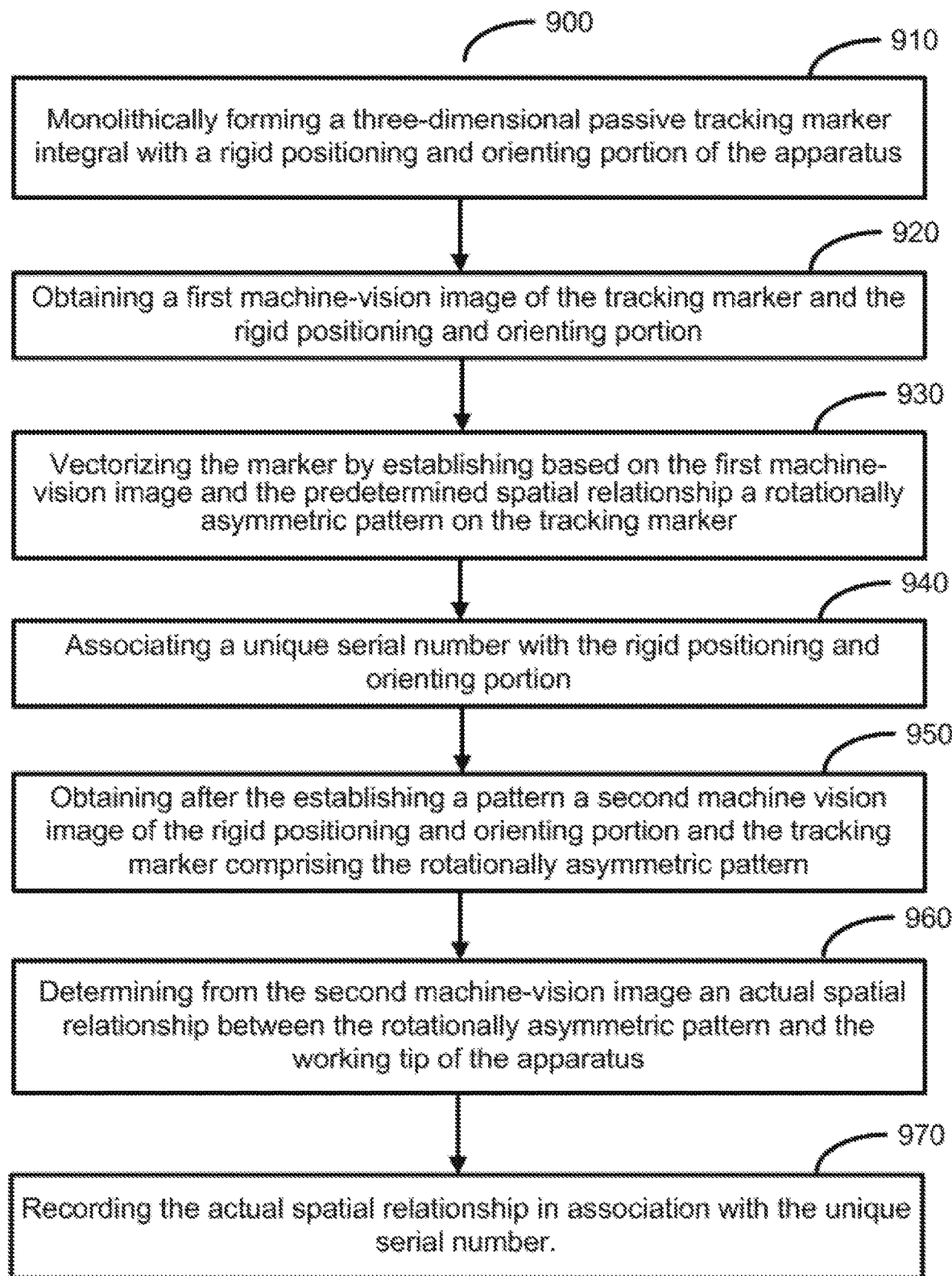
FIG. 21 shows a flow chart of a method for making a three-dimensionally trackable apparatus.

As described at the hand of FIG. 21, method [900] for making a three-dimensionally trackable apparatus having a working tip is provided, the method comprising monolithically forming [910] a three-dimensional passive tracking marker integral with a rigid positioning and orienting portion of the apparatus, the rigid positioning and orienting portion having a predetermined spatial relationship with respect to the working tip; obtaining [920] a first machine-vision image of the tracking marker and the rigid positioning and orienting portion; and vectorizing [930] the marker by establishing based on the first machine-vision image and the predetermined spatial relationship a rotationally asymmetric pattern on the tracking marker. In other embodiments, the three-dimensional passive tracking marker may be integrated with the rigid positioning and orienting portion of the apparatus such that it is permanently integrated, but not specifically monolithically integrated. By way of non-limiting example, the marker may be attached using epoxy cement, thereby permanently fixing its position and orientation on the rigid positioning and orienting portion of the apparatus. The apparatus may be, for example, a handheld implement. Establishing [930] a rotationally asymmetric pattern may comprise establishing a plurality of contrasting portions. The method may further comprise associating [940] a unique serial number with the rigid positioning and orienting portion; obtaining [950] after the establishing a pattern a second machine vision image of the rigid positioning and orienting portion and the tracking marker comprising the rotationally asymmetric pattern; determining [960] from the second machine-vision image an actual spatial relationship between the rotationally asymmetric pattern and the working tip; and recording [970] the actual spatial relationship in association with the unique serial number. Recording may comprise affixing a contactlessly interrogatable microchip to the at least one portion; and programming the actual spatial relationship into the microchip. The recording may comprise recording the spatial relationship in a database. The microchip may have a memory and the database may be stored in the memory of the microchip.

The microchip may be, for example without limitation, an RFID (Radio Frequency Identification) microchip, or, more specifically, a Near Field Communication (NFC) microchip, or it may be interrogatable by magnetic induction means. The interrogative coupling with the microchip may be via suitable circuitry for capacitive coupling, inductive coupling, radiative coupling (also known as "backscatter") or battery assisted RF communication. Passive microchip circuits may be employed, the power being provided by the interrogating device employed to access the data on the chip.

Establishing a plurality of contrasting portions may comprise establishing at least one contrasting portion having a mathematically describable perimeter. The establishing a rotationally asymmetric pattern may comprise one of scribing, engraving, stamping, and embossing contrasting portions onto the tracking marker.

In the foregoing descriptions of various embodiments, the asymmetric pattern on a tracking marker or a unique shape of the tracking marker may be used as a basis on which to identify a fiducial or a tracking marker in the field of view of a tracker of the system. In further embodiments, an identifying marking, distinct from any asymmetric pattern, may be disposed on the tracking markers of the system, each such identifying marking being unique. The unique identifying markings may be employed to differentiate within the system among different tracking markers bearing identical asymmetric patterns for the purposes of tracking. In one non-limiting example, the system may comprise tracking markers of different shapes selected to meet the needs of a particular surgical process, each of the tracking markers bearing the identical asymmetric pattern for purposes of tracking, but each tracking marker having a unique identifying marking. The marking may be any one of, or any combination of, a symbol, a digit, a letter, and a pattern, or pluralities of the same.

The industrial significance and benefit of the implements, systems and methods described in this disclosure reside in the fact that the permanently integrated tracking markers are spatially calibrated with respect to any operating tip of the implement in use. The operating tips may be operating tips of interchangeable portions of the implements such as, for example without limitation, drill bits. To this end, the tracking markers are integrated with the invariant portions of the implements disclosed here. In the case of the present implements, the spatial calibration of the markers with respect to the operating tips is done during manufacture of the implements. The markers may be, as already explained, specifically monolithically integrated with the invariant portions of the implements disclosed. This is to be contrasted with prior art implements in which tracking markers, if employed at all, are calibrated before each occasion the implement is employed. The reason for this is that there is a significant risk that markers not permanently attached may move between periods of use or even during use. The merit of monolithic integration of the markers with the invariant portions of implements resides in the fact that the monolithic integration ensures with 100% certainty that that there will be no change in the spatial relationship between a working tip of the implement either during use or between sessions of use. The benefit of not having to re-calibrate resides in the fact that extensive amounts of costly time may be saved. Conversely, having to recalibrate a key implement during surgery is a major operational problem that can have disastrous medical consequences if not performed 100% correctly.

While this invention has been described as having an exemplary design, the present invention may be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains.

What is claimed is:

1. A method for tracking a handheld implement bearing a passive vectorized tracking marker permanently integrated with the implement, the marker having an identifiably unique rotationally asymmetric pattern of contrasting elements disposed on the marker, the method comprising:
    providing the handheld implement bearing a passive vectorized tracking marker permanently integrated with the implement;
    obtaining image information about the implement from a non-stereo optical tracker;
    obtaining from a database geometric information about the tracking marker;
    identifying the passive vectorized tracking marker on the basis of the unique pattern;
    determining within the image information the location of at least one pattern reference point of the passive vectorized tracking marker based on the geometric information, and
    determining within the image information a rotational orientation of the passive vectorized tracking marker based on the geometric information.

2. The method of claim 1, wherein obtaining from a database geometric information comprises obtaining information about the locations of contrasting pattern elements within the at least one pattern.

3. The method of claim 1, wherein the providing the handheld implement comprises providing a handheld implement bearing a passive vectorized tracking marker monolithically integrated with the implement.

4. The method of claim 1, wherein the determining the location of the at least one pattern reference point of the passive vectorized tracking marker comprises differentiating between different unit cells of rotationally asymmetric patterns in the image information and confirming one of the absence and the presence of contrasting pattern elements at occupiable locations within the unit cells.

5. The method of claim 4, wherein the confirming comprises detecting a color contrast between the pattern elements and the at least one passive vectorized tracking marker on which they are disposed.

6. The method of claim 4, wherein the confirming comprises calculating the occupiable locations on the passive vectorized tracking marker based on the geometric information from the database.

7. The method of claim 4, wherein the differentiating is based on a center-to-center distance between two closest neighbor pattern elements within the at least one rotationally asymmetric pattern.

8. The method of claim 4, wherein the differentiating between different unit cells of rotationally asymmetric patterns comprises differentiating between different unit cells of rotationally asymmetric patterns.

9. The method of claim 1, wherein the determining the location of the at least one pattern reference point further comprises fitting a mathematical curve to a perimeter of at least one of the contrasting pattern elements.

10. A method for monitoring changes in a handheld surgical implement in three dimensions relative to a surgical site, the method comprising:
    attaching a single passive vectorized scan-visible fiducial reference at a fiducial location proximate the surgical site;
    obtaining scan data by performing a scan of the surgical site and the fiducial location with the fiducial reference attached;
    obtaining from the scan data a three-dimensional spatial relationship between the fiducial reference and the surgical site;
    disposing in a field of view of a tracker a first passive vectorized tracking marker in fixed spatial relation with the fiducial reference;
    disposing in the field of view of the tracker the surgical implement comprising an interchangeable portion and an invariant portion, the invariant portion bearing a second passive vectorized marker permanently integrated with the invariant portion;
    obtaining image information of the field of view from the tracker;
    determining from the image information a three-dimensional location and orientation of the first tracking marker relative to the surgical site;
    identifying the interchangeable portion of the surgical implement in the image information; and
    determining from the image information and from the three-dimensional location and orientation of the first tracking marker relative to the surgical site a three-dimensional location and orientation of a working tip of the interchangeable portion of the surgical implement relative to the surgical site.

11. The method of claim 10, wherein disposing in the field of view of the tracker the surgical implement comprises disposing in the field of view of the tracker a surgical implement comprising an invariant portion bearing a second passive vectorized marker monolithically integrated with the invariant portion.

12. The method of claim 10, wherein determining of the location and orientation of a working tip of the interchangeable portion relative to the surgical site comprises determining from the image information the three-dimensional location and orientation of the second tracking marker attached to the invariant portion.

13. The method of claim 10, wherein identifying the interchangeable portion of the surgical implement in the image information is based on pre-surgical information in a database.

14. The method of claim 10, wherein identifying the interchangeable portion of the surgical implement in the image information comprises determining the three dimensional location of the working tip of the interchangeable portion and determining the length of the interchangeable portion from the three-dimensional location of the working tip and the three-dimensional location and orientation of the second tracking marker.

15. The method of claim 10, wherein determining the three dimensional location of a working tip of the interchangeable portion comprises triangulating the three dimensional location of the working tip based on two separate perspectives of the interchangeable portion in the field of view of the tracker.

16. A method for making a three-dimensionally trackable apparatus having a working tip, the method comprising:
   permanently integrating a three-dimensional passive tracking marker with a rigid positioning and orienting portion of the apparatus, the rigid positioning and orienting portion having a determinable spatial relationship with respect to the working tip;
   obtaining a first machine-vision image of a mutually integral tracking marker and at least one portion;
   vectorizing the tracking marker by establishing based on the first machine-vision image and the predetermined spatial relationship a rotationally asymmetric pattern on the tracking marker.

17. The method of claim 16, wherein the establishing a rotationally asymmetric pattern comprises establishing a plurality of contrasting portions.

18. The method of claim 16, wherein the establishing a plurality of contrasting portions comprises establishing at least one contrasting portion having a mathematically describable perimeter.

19. The method of claim 16, wherein the establishing a rotationally asymmetric pattern comprises one of scribing, engraving, stamping, and embossing the contrasting portions.

20. The method of claim 16, wherein the permanently integrating comprises monolithically forming a three-dimensional passive tracking marker integral with the rigid positioning and orienting portion of the apparatus.

21. The method of claim 16, further comprising:
   associating a unique serial number with the rigid positioning and orienting portion;
   obtaining after the establishing a pattern a second machine vision image of the rigid positioning and orienting portion and the tracking marker comprising the rotationally asymmetric pattern;
   determining from the second machine-vision image an actual spatial relationship between the rotationally asymmetric pattern and the working tip; and
   recording the actual spatial relationship in association with the unique serial number.

22. The method of claim 21, wherein the recording comprises:
   affixing a contactlessly interrogatable microchip to the rigid positioning and orienting portion; and
   programming the actual spatial relationship into the microchip.

* * * * *